(12) United States Patent
Pandit et al.

(10) Patent No.: US 8,734,848 B2
(45) Date of Patent: May 27, 2014

(54) HOLLOW BIODEGRADABLE NANOSPHERES AND NANOSHELLS FOR DELIVERY OF THERAPEUTIC AND/OR IMAGING MOLECULES

(71) Applicant: National University of Ireland, Galway (NUIG), Galway (IE)

(72) Inventors: Abhay Pandit, Galway (IE); Gildas Rethore, Nantes (FR); Hemantkumar Naik, Yellapur (IN); Yvonne Lang, Sligo Town (IE); David Finn, Oranmore (IE)

(73) Assignee: National University of Ireland, Galway (NUIG), Galway (IE)

( * ) Notice: Subject to any disclaimer, the term of this patent is extended or adjusted under 35 U.S.C. 154(b) by 0 days.

(21) Appl. No.: 14/014,131

(22) Filed: Aug. 29, 2013

(65) Prior Publication Data

US 2014/0004251 A1    Jan. 2, 2014

Related U.S. Application Data

(60) Division of application No. 12/886,492, filed on Sep. 20, 2010, which is a continuation-in-part of application No. PCT/EP2009/053258, filed on Mar. 19, 2009.

(30) Foreign Application Priority Data

Mar. 20, 2008 (IE) .................................... 2008/0211

(51) Int. Cl.
*A61K 9/14* (2006.01)

(52) U.S. Cl.
USPC ........................................................ 424/489

(58) Field of Classification Search
None
See application file for complete search history.

(56) References Cited

U.S. PATENT DOCUMENTS 6,720,007 B2 * 4/2004 Walt et al. ..................... 424/489

* cited by examiner

*Primary Examiner* — Paul Dickinson
(74) *Attorney, Agent, or Firm* — Foley & Lardner LLP; Antoinette F. Konski

(57) ABSTRACT

A polymeric hollow nanoshell or nanosphere for release of an agent is described, wherein the hollow nanosphere comprises at least one biodegradable polymer, characterised in that the polymer is cross-linked. The biodegradable mono-disperse nanospheres described are suitable for use as carriers of biomolecules, therapeutic agents and/or imaging agents.

14 Claims, 40 Drawing Sheets

(A)

(B)

(C)

(A)　　　　　　　　　　(B)

(A)

(B)

(C)

(D)

(E)

(F)

(A)

(B)

(C)

HOLLOW BIODEGRADABLE NANOSPHERES AND NANOSHELLS FOR DELIVERY OF THERAPEUTIC AND/OR IMAGING MOLECULES

CROSS REFERENCE TO RELATED APPLICATIONS

This application is a divisional of U.S. application Ser. No. 12/886,492, filed Sep. 20, 2010, which is a continuation-in-part of International Application No. PCT/EP2009/053258, filed Mar. 19, 2009, which in turn claims priority to Irish Application No. 2008/0211, filed Mar. 20, 2008, the contents of each of which are hereby incorporated by reference in their entireties.

FIELD OF THE INVENTION

The present invention relates to biodegradable mono-dispersed nanospheres and nanoshells for use as carriers of biomolecules, therapeutic agents and/or imaging agents or for use in other nanoshell and nanosphere applications. In particular, the invention relates to biodegradable nanospheres and nanoshells which may be modified to target drug or agent delivery to a specific site.

BACKGROUND OF THE INVENTION

There is a significant clinical need for novel methods of detection and treatment of gene disorders and diseases, such as cancer, that offer improved sensitivity, specificity, and cost-effectiveness. The object of any gene or drug therapy is to safely deliver therapeutic agents inside the cell. It has been more than 12 years since the first gene therapy trial, and to date, after much intense research and more than 600 clinical trials, no gene therapy has been approved. The main hurdle to overcome in this field is the lack of efficient, specific and safe nucleic acid (DNA, miRNA or sRNA) delivery systems. For successful delivery, the therapeutic agent or imaging agent/nucleic acid should be delivered to the target tissue or cell type. Once delivered to the local target site, the agent should be able to enter the cell for imaging or repair. The delivery device should be smaller than the size of the target cell in order to achieve entry into the cell. Chan et al., *Nano Lett.;* 6(4), 662-668 (2006) have reported the effect of the size of a delivery device on cell penetration. According to the research, a device which is nano-meters in size could enter a cell whose size is higher than micrometers.

In recent years, polymeric micelles have been the object of growing scientific attention. Polymeric micelles have emerged as a potential carrier for biomolecules for several reasons. They can solubilise biomolecules in their inner core, they offer attractive characteristics in spatial dimensions (>100 nm) for cell entry and they have the capacity to evade scavenging by the mononuclear phagocyte system. Advantageously, micelle forming polymers usually contain block co-polymers, which are found in sequences of hydrophobic blocks of the copolymer comprised of poly(caprolactone), poly(d,l-lactide) or poly(propylene) with a hydrophilic block of poly(ethylene glycol) PEG segments. With such polymers, it is possible to design a system that does not precipitate out of solution, is stable and contains a large number of distinct microscopic domains. These domains usually possess hydrophobic cores and highly hydrated hydrophilic shells or coronas. Current micellar systems however are only responsive to a limited extent to their biological environment and cannot be functionalized for specific delivery to a target cell.

Recently, nanoparticles are thought to have potential as novel probes for both diagnostic (e.g. imaging) and therapeutic purposes (e.g. drug delivery). In particular, specialized nanoparticle systems known as nanoshells, have shown promise in delivering genes to cells. However, these nanoshells are generally made of non-biodegradable materials, for example, synthetic polymers such as polyallylamine hydrochloride or inorganic material such as gold or silica, which have long-term biocompatibility concerns.

A number of other techniques have been investigated to direct therapeutics and diagnostic agents to tumours. These have included targeting of tumour cell surface molecules, targeting regions of activated endothelium, utilizing the dense and leaky vasculature associated with tumours and taking advantage of the enhanced metabolic and proteolytic activities associated with tumours. Antibody labelling has been used to achieve cell-selective targeting of therapeutic and diagnostic agents. A number of approaches have been taken for antibody-targeting of therapeutic agents. These have included direct conjugation of antibodies to drugs such as interferon alpha, tumour necrosis factor and saporin. Antibody conjugation has also been used for tumour-targeting of radioisotopes for radioimmunotherapy and radioimmunodetection. Currently, there is a commercial product for detection of prostate cancer (ProstaScint) that is an antibody against prostate-specific membrane antigen conjugated to a scintigraphic target.

International Patent Publication No. WO 01/64164 describes labelled nanocapsules comprising DNA within surfactant micelles and encapsulated within a biocompatible hydrophilic polymer.

Virus particles have been developed that display single chain antibodies on their surface, allowing specific targeting of a wide variety of cell types. In order to target regions of activated endothelium, immunoliposomes have been made with antibodies to E-selectin on their surfaces. Recently tumours have been imaged using protease-activated near infrared fluorescent probes.

Over the past several years, there has been increasing interest in combining emerging optical technologies with the development of novel exogenous contrast agents, designed to probe the molecular specific signatures of cancer and to improve the detection limits and the clinical effectiveness of optical imaging.

Sokolov et al (*Cancer Research* 63, 1999-2004 (2003)) recently demonstrated the use of gold colloid conjugated to antibodies to the epidermal growth factor receptor (EGFR) as scattering contrast agents for biomolecular optical imaging of cervical cancer cells and tissue specimens. In addition, multiple groups including Bruchez et al. (*Science* 281, 2013-2016 (1998)) and Akerman et al. (*Proc. Natl. Acad. Sci. U.S.A.,* 99, 12617-12621 (2002)) have disclosed optical imaging applications of nanocrystal bioconjugates. More recently, interest has developed in the creation of nanotechnology-based platform technologies, which couple molecular specific early detection strategies with appropriate therapeutic intervention and monitoring capabilities.

Nedeljkovic and Patel (*Appl. Phys. Lett.,* 58, 2461-63, (1991)) disclosed silver-coated silver bromide particles that are produced by intense UV irradiation of a mixture of silver bromide, silver, sodium dodecylsulfate (SDS) and ethylenediaminetetraacetic acid (EDTA). The Neideljkovic particles range in size from approximately 10 to 40 nm and are irregularly shaped as determined by transmission electron microscopy. Predictably, the spectra obtained from these particle preparations are extremely broad.

U.S. Pat. No. 5,023,139 discloses theoretical calculations indicating that metal-coated, semiconducting, nanometer-sized particles should exhibit third-order non-linear optical susceptibility relative to uncoated dielectric nanoparticles. This is due to local field enhancement. In those embodiments that do in fact propose a metal outer shell, there is an additional requirement as to the specific medium in which they must be used in order to properly function. Shell sizes have, in general, been relatively large, usually of the order of about 5 µm. In drug delivery applications, a smaller particle diameter is important for prolonged blood circulation and enhanced drug targeting to specific body sites.

U.S. Pat. No. 6,479,146 describes a process for preparing coated particles and hollow shells by coating colloidal particles with alternating layers of oppositely charged nanoparticles and polyelectrolytes, and optionally removing the colloidal cores. The process involves the preparation of hollow silica microspheres via layer-by-layer shell assembly on 640 nm diameter polystyrene latex particles, followed by pyrolysis at 500° C. to decompose the polystyrene core. The same assembly procedure was also used to prepare silica-containing shells on 3 µm diameter melamine-formaldehyde particles, followed by acid dissolution of the core.

International Publication No. WO 2005/044224 describes a drug delivery system based on polymer nanoshells. In certain embodiments, the polymeric nanoshells comprise one or more polymeric shells around a hollow core. In other embodiments, nanoshells are described which are useful for the delivery of agents such as, for example, various diagnostic and therapeutic agents. The nanoshells disclosed are preferably composed of biocompatible organic polymers which are most preferably biodegradable as well. The shell layers can comprise materials such as gelatin, chitosan, dextrate sulphate, carboxymethyl cellulose, sodium alginate, poly(styrene sulfonate) (PSS), poly(lysine), poly(acrylic acid), poly (dimethyldiallyl ammonium chloride) (PDDA) and poly (allylamine hydrochloride) (PAH). However, the shells described are composed of an electrostatic interaction multilayer-based membrane. Thus negative and positive charges are required on the particle, the electrostatic nature of the surface induces interactions with proteins and lipoproteins during the blood circulation. Such non-specific interaction can decrease the nanoparticle lifetime.

Hu et al (Polymer, Vol. 46, Issue 26, 2005 pg. 12703-12710) describe formation of hollow polymeric nanospheres based on a core-template-free route, and the effects of polymerization concentration, shell cross-linking, pH, salt concentration and temperature on the size and stability of hollow polymeric nanospheres. The hollow structure of polymeric nanospheres is spontaneously formed by polymerization of acrylic acid monomers inside the chitosan-acrylic acid assemblies. The size of the hollow nanospheres can be manipulated by changing pH, salt concentration and temperature.

Li et al (Colloid & Polymer Science, Vol. 286, 6-7, pg. 819-825) describe biodegradable chitosan hollow microspheres where are prepared using uniform sulfonated polystyrene (PS) particles as templates. The chitosan was adsorbed onto the surface of the sulfonated polystyrene templates through the electrostatic interaction between the sulfonic acid groups on the templates and the amino groups on the chitosan and crosslinked using glutaraldehyde. The controlled release behavior of the chitosan hollow microspheres was also primarily investigated after template removal.

The limited success of current pharmaceutical therapies is due to the absence of an innovative drug delivery system which can increase the safety and efficacy levels but also improve the overall performance of the therapeutic molecule. Stability and degradability control are two critical aspects that must be developed to facilitate delivery. Controlling these parameters simultaneously is a greater challenge, and most of the current vectors such as liposomes, microparticles and microemulsions do not support this, thus limiting their applications. Moreover, another major disadvantage of synthetic vectors is their low in vivo efficiency. This is a consequence of their poor targeting ability and their short lifetime due to the presence of surface positive charge or the inherently low stability of their shells (liposomes). These factors lead to the degradation of the supramolecular structure and removal by macrophages before the vector arrives at the target cell. To circumvent these problems, hollow spheres appear to be a promising strategy. Recent interest in hollow spherical structures can be attributed to their unusual properties (chemical, mechanical and optical) which suggest a wide range of applications. These structures have potential utility in encapsulation and controlled release of various biomolecules such as genes, peptides and drugs in clinical applications. Control of the structural characteristics of the hollow carrier such as shell thickness, surface charge, pore size and mechanical strength is essential to achieving the aim of realising an ideal encapsulation system.

Clearly, there is a need therefore to develop the next generation of hollow nanospheres that are more robust, biocompatible and are responsive to their environment, thus triggering the smart release of the biomolecule after delivery to the target. It is desirable that these polymeric systems would be biocompatible, capable of carrying a high payload, capable of acting as a reservoir and could be programmed to respond to temperature and the like and be modified to target drug delivery to a specific site.

It is thus an object of the present invention to provide improved biodegradable hollow mono-dispersed nanospheres which are adaptable to target specific sites for use as carriers of and to allow targeted and controlled delivery of biomolecules and therapeutic agents and the like or for use in other nanosphere applications.

It is a further object of the invention to provide biodegradable nanoshells which are adaptable to target specific sites, thereby allowing targeted and controlled delivery of biomolecules and therapeutic agents and the like.

SUMMARY OF THE INVENTION

Accordingly, the invention provides a polymeric hollow nanosphere for release of an agent, wherein said nanosphere comprises at least one biodegradable polymer, characterised in that said at least one polymer is cross-linked. Thus, the nanospheres of the invention comprises at least one biodegradable polymer which is crosslinked with a crosslinking agent.

In particular, the invention provides hollow biodegradable nanospheres which are specifically designed to allow for higher pay load capacity and which can act as a local reservoir with a controlled release profile and provide a sustained delivery of the therapeutic agent to the target site over time. These hollow nanospheres with a higher pay load capacity can target drug or agent delivery to a specific site.

Cross-linking preferably arises from covalent linkages between the polymer and the cross-linking agent.

In one aspect there is provided a polymeric hollow nanosphere for release of an agent,
wherein said hollow nanosphere comprises at least one natural or synthetic biodegradable polymer, selected from the group consisting of: collagen, elastin, chitosan, hyaluronan, alginate, polyesters, PEG-based polymers, dendritic or hyperbranched polymers and combinations thereof, wherein said at least one natural or synthetic biodegradable polymer is cross-linked by a cross-linking agent selected from at least one of the group consisting of a dendrimer, hyper-branched dendritic polymer and a linear polymeric system;

characterised in that the molar ratio of reactive —COOH or —NH$_2$ groups in said cross-linker to reactive groups —COOH or —NH$_2$ in said polymer is in the range 50:1 to 1:50.

The invention thus relates to the design of hollow biodegradable nanospheres which are specifically designed to allow for higher pay load capacity and which can act as a local reservoir with a controlled release profile and provide a sustained delivery of the therapeutic agent to the target site over time. These hollow nanospheres with a higher pay load capacity can target drug or agent delivery to a specific site.

The skilled person will appreciate that the ratio of cross-linking agent to polymer can be varied to tailor the physical properties of the nanosphere. The choice of cross-linking agent selected for cross-linking the polymeric nanosphere will also affect the physical properties of the nanosphere.

In all embodiment described herein, by the phrase "the ratio of cross-linker to polymer" it is meant that the ratio of reactive —COOH or —NH$_2$ groups in said dendrimer cross-linker to reactive groups —COOH or —NH$_2$ in said polymer. This ratio is a molar ratio.

For all disclosed embodiments it is preferred, the molar ratio of reactive —COOH or —NH$_2$ groups in said dendrimer cross-linker to reactive groups —COOH or —NH$_2$ in said polymer is in the range of 10:1 to 1:10 and more particularly preferred 5:1 to 1:5. Preferably the invention provides a polymeric nanosphere wherein the molar ratio of cross-linker reactive groups to polymer reactive groups is in the range of 5:1 to 1:5. In the most preferred embodiment of the invention, the ratio of cross-linker to polymer is 1:2. The inventors have found that a ratio of 1:2 cross-linker to polymer produces well defined nanospheres. In another preferred embodiment, the ratio of cross-linker to polymer may be 1.5:2. This ratio is a molar ratio. This ratio is a molar ratio.

The biodegradable polymer may be selected from the group consisting of: collagen, elastin, chitosan, hyaluronan, alginate, polyamidoamine (PAMAM), poly-l-lysine (PLL), polyethyleneimine (PEI), polyglutamic acid (PGA), poly (ethylene glycol) methacrylate (PEGMA) and poly (propylene glycol) methacrylate (PPGMA), (meth) acrylic acid monomers (e.g. methacrylic acid and acrylic acid) or NHS monomers (e.g. acrylic acid N-hydroxysuccinimide ester) with multi-functional vinyl monomers (e.g. PEG dimethacrylate), and polycarboxylic acid-polyethylene glycol-polycarboxylic acid polymers such as APEGA, and combinations thereof. In a preferred embodiment peptides amphiphiles such as those well known in the art may be used. Peptide amphiphiles include poly(L-lysine), TMA[-Ala-TRIS[(Gly-Pro-Nleu)$_6$-OMe]$_3$]$_3$, Ala periphery [(β-Ala$_8$-Orn$_4$-Orn$_2$-Orn-NH—CH$_2$—CH$_2$—)$_2$, [(H-Gly-Pro$_5$)$_2$-Amp]$_2$-(Gly-Pro$_5$)$_2$-Amp-CONH$_2$, and Proline-rich MAPs.

In a preferred embodiment, the biodegradable polymer may comprise a combination of polymers selected from the group consisting of: chitosan and polyglutamic acid; PAMAM and hyaluronan; and chitosan and collagen.

Natural biodegradable polymers are preferred and include biodegradable polymers such as collagen, elastin, chitosan, hyaluronan or alginate and combinations thereof. The skilled person will appreciate that elastin includes elastin like polypeptide (ELP) or pre-elastin such as tropoelastin can also be used. Mixtures of at least two natural polymers are particularly preferred.

Preferred synthetic biodegradable polymer include polyesters, PEG-based polymers, dendritic or hyperbranched polymers and combinations thereof.

Preferably, the cross-linking agent is selected from the group consisting of dendrimers or dendritic polymeric systems, glutaraldehyde, carbodiimides, genepin, transglutaminase, sulfonates, including methyl sulfonate and trifluoromethyl sulfonate, and malemide. Glutaraldehyde is less preferred as it is toxic. The skilled person will appreciate that cross linking promoters can be used to induce/assist crosslinking. However, dendrimers or dendritic polymeric systems are the most preferred cross-linking agents for the natural polymeric hollow nanospheres of the invention.

The most suitable cross-linking agents include dendrimers or dendritic polymeric systems. Dendrimers are spherical, highly branched polymers having specific functionalised surface chemistries. Dendritic polymeric systems include dendritic architectures such as dendrimers, dendronized, hyperbranched and brush-polymers. The area of dendritic molecules can be roughly divided into the low molecular weight and the high molecular weight species. Dendrimers of different generations can be used according to the needs of the particular application. For example, dendrimer or dendritic polymeric systems of different generations, e.g, $G_1$-$G_{10}$ or half generations may be used.

Preferably, the dendrimer is a PPEGP based dendrimer. The dendrimer can comprise a tricarboxylic acid monomer core (such as an aconitic acid core) and polyol branching monomer (such as PEG). Thus, the dendrimer may suitably comprise an aconitic acid (core) and PEG (surface) based dendrimer such as aconitic acid-polyethylene glycol-aconitic acid based dendrimer (APEGA). More preferably, the dendrimer may comprise a pre-activated carboxylic acid functionalised polyether dendrimer, such as a pre-activated carboxylic acid functionalised APEGA dendrimer.

The degradation products of the nanospheres according to the invention are biocompatible and absorbable. Natural polymers typically degrade in the body to into low molecular weight peptides, oligosaccharides and very low molecular weight hyaloronan.

Advantageously, the rate of degradation and thus lifetime, of the nanosphere can be tailored by cross-linking the polymer matrix with different cross-linkers (co-polymers) and by modulating the cross-linking ratio. More strongly cross-linked hollow nanospheres will be more resistant to degradation and will take longer to degrade than less cross-linked hollow nanospheres. The skilled person will appreciate that the ratio of cross-linking agent to polymer can be varied to tailor the physical properties of the nanoshell. The choice of cross-linking agent selected for cross-linking the polymeric nanoshell or nanosphere will also affect the physical properties of the nanoshell. The skilled person will appreciate that the ratio of cross-linker to polymer can be selected according to the desired end properties of the nanosphere, for example degree of biodegradability, rigidity, and biological properties.

Furthermore, the nanoshells and nanospheres of the invention illustrate that cross-linking of the polymers forming the nanosphere improves the stability and mechanical integrity of the nanosphere. Furthermore, the degree of cross-linking can affect various physical properties of the nanosphere such as the permeability of the sphere wall, the rate of degradation of the sphere, and the rate of release of agents encapsulated within the sphere, for example.

Dendrimers or dendritic polymeric systems are the preferred cross-linking agents for the natural polymeric hollow nanospheres of the invention.

The nanospheres as described herein are superior to existing nanospheres insofar as they can be developed with a neutral surface charge ratio. Neutral surfaces are preferred over ionic surfaces since non-specific interactions are decreased and thus the nanosphere lifetime is augmented. Furthermore, covalent surface linkages are preferred over ionic surfaces since nanospheres comprising covalent surfaces mean that the nanospheres of the present invention can be used at neutral pH or in physiological serum.

The dendrimer may be selected from the group consisting of polyamidoamine (PAMAM), polypropyleneimine (PPI), polyarylether (PAE), polyethyleneimine (PEI), poly-l-lysine (PLL), polyacrylic acid-(polyethylene glycol)-polycarboxylic acid (PPEGP); polycarboxylic acid-(polyethylene glycol)-polycarboxylic acid (PPEGP); or from poly(ethylene glycol)methacrylate (PEGMA) and poly(propylene glycol) methacrylate (PPGMA) mixtures, in ratios ranging from 70:30 to 25:75.

The dendritic polymeric systems synthesized from the combinations of the latter two polymers with tailored functional groups (carboxylic or NHS groups) can be designed and synthesized via the controlled/living free radical copolymerisations (ATRP or RAFT) of conventional (meth) acrylic acid monomers (e.g. methacrylic acid and acrylic acid) or NHS monomers (e.g. acrylic acid N-hydroxysuccinimide ester) with multi-functional vinyl monomers (e.g. PEG dimethacrylate). These resultant carboxylic or NHS functionalized dendritic polymeric systems can be conjugated or cross-linked with peptides, proteins and chitosan via their amine functional groups, for the tethering of drug/growth factors.

Peptide-based dendrimers such as poly(L-lysine), TMA[-Ala-TRIS[(Gly-Pro-Nleu)$_6$-OMe]$_3$]$_3$ improve the exposure of the functionalities to the surrounding environment and mimic the architectures of biological structures which have naturally evolved to facilitate specific bio-interactions. They also exhibit desirable biological activities and facilitate the synthesis of highly controlled constructs of consistent size, architecture and composition. Multi-antigenic peptides form a dendrimeric structure with various exposed functionalities. Nanostructured peptide dendrimers based on different amino acids, including lysine, exhibit promising vaccine, antiviral and antibacterial properties. Exploiting the inherent property of several surfactant-like peptides which undergo self-assembly enables the formation of nanotubes and nanovesicles having an average diameter of 30-50 nm with a helical twist.

In a particularly preferred embodiment, there is provided a polymeric hollow nanosphere for release of an agent, wherein said nanosphere comprises at least one natural biodegradable polymer, selected from the group consisting of: collagen, elastin, chitosan, hyaluronan and alginate, wherein said at least one polymer is cross-linked by a cross-linker agent selected from the group consisting of: a dendrimer or a dendritic polymeric system selected from the group consisting of: aconitic acid-polyethylene glycol-aconitic acid based dendrimer (APEGA), polyamidoamine (PAMAM), polypropyleneimine (PPI), polyarylether (PAE), polyethyleneimine (PEI), poly-l-lysine (PLL), polyacrylic acid-(polyethylene glycol)-polycarboxylic acid (PPEGP); polycarboxylic acid-(polyethylene glycol)-polycarboxylic acid (PPEGP); or from poly(ethylene glycol)methacrylate (PEGMA) and poly(propyleneglycol) methacrylate (PPGMA) mixtures, in ratios ranging from 70:30 to 25:75 characterised in that the molar ratio of reactive —COOH or —NH$_2$ groups in said dendrimer cross-linker to reactive groups —COOH or —NH$_2$ in said polymer is in the range 50:1 to 1:50. More preferably, the molar ratio of reactive —COOH or —NH$_2$ groups in said dendrimer cross-linker to reactive groups —COOH or —NH$_2$ in said polymer is in the range 5:1 to 1:5.

The polymeric coating of the nanosphere may be cross-linked with dendrimer using EDC/NHS coupling. The use of a dendrimer using EDC/NHS coupling makes more functional groups available for surface modification of the shells such as for tethering imaging agents or specific site receptors, for example. A pre-activated carboxylic acid functionalised polyether dendrimer, such as a pre-activated carboxylic acid functionalised APEGA dendrimer can also be used, since such dendrimers are activated for facilitating polymer cross-linking without the need for use of carbodiimide chemistry. Aconitic acid-polyethylene glycol-aconitic acid based dendrimer (APEGA) is particularly preferred.

Biodegradable dendrimers such as poly(glycerol-succinic acid) dendrimer (PGLSA), poly(2,2-bis(hydroxymethyl)propionic acid) provide biodegradable crosslinking polymer without production of toxic residues and allow programming of cross-linked spaces in the polymer in question. This is advantageous over use of EDC/NHS coupling, since this can often result in production of zero-length cross links within the polymer.

In accordance with the present invention, nanospheres of specific sizes are prepared for their absorbance by specific cells in the body. The invention provides mono-dispersed biodegradable polymer based nanospheres of a range of dimensions.

The nanospheres of the invention may be sized in the range 1 nm to 5000 nm. Preferably, the nanosphere has a size in the range from 10 nm to 50 nm, more preferable 50 nm to 100 nm, more preferable still from 100 nm to 200 nm, from 200 nm to 500 nm, more preferably from 0.1 to 5 µm (100 nm to 5000 nm). Further preferably, the nanosphere has a size in the range of 0.1 to 2 µm (100 nm to 2000 nm). The size of the nanosphere is of particular importance for controlled delivery of agents to target cells in the body. The nanosphere will be smaller in size than the target cell, which has an average size of 50 µm.

In a preferred embodiment, the polymeric chitosan nanospheres of the present invention can be cross-linked directly with carboxylic acid functionalised dendritic polymeric systems or with NHS-functionalised dendrimers or dendritic polymeric systems. The polystyrene core template can be removed from the nanosphere template by dissolution using THF. The preferred chitosan nanospheres can be fabricated and functionalized according to the methodology described herein.

Preferably, the nanospheres according to the present invention provide for controlled release of an agent at a target site. Further preferably, the nanospheres of the present invention provide for controlled, targeted delivery of an agent or agents to a site.

The controlled delivery is one of the most important goals for synthetic gene delivery. It has been proved that moieties such as polysaccharides, antibodies and peptides, for example increase the targeting of specific cells (e.g. mannose to macrophages; galactose to hepatocytes; folic acid to cystic fibrosis cells, etc.).

The polymeric nanospheres according to the invention comprise a hollow cavity. The hollow cavity within the shell can be used to encapsulate agents that require delivery to a target cell. The agent may be selected from the group consisting of biomolecules, therapeutic agents or imaging agents.

Suitable agents include but are not limited to pDNA, polyplexes, growth factors, peptides, viral and non-viral vectors (pDNA), doxorubicin, genes, hormones, enzymes, FITC, tryptophan, rhodamine, 4',6-diamidino-2-phenylindole (DAPI) and TOPRO3, for example. Other agents include fluorescein and it's derivatives, red dyes, green dyes such as AlexaFlor; and fluorescent proteins such as GFP/eGFP, YFP, and chemicals, APIs, drugs and pro-drugs.

Encapsulation of the therapeutic agent protects it from the outside environment, thereby, increasing the half-life of the agent. Encapsulation also protects the therapeutic agent from non-specific site interaction during penetration. Thus, the biomolecule is protected during the journey of the device to the target site.

In one embodiment the nanospheres according to the invention can be used for molecular imaging by impregnating the shells with imaging agents. Accordingly, the nanosphere according to the invention may further comprise an imaging agent. The imaging agent may be encapsulated in the shell. In an alternative embodiment an imaging agent may be attached to the exterior surface of the nanosphere. The imaging agent may be selected from the group consisting of FITC, tryptophan, rhodamine, 4',6-diamidino-2-phenylindole (DAPI) and TOPRO3. Other agents include fluorescein and it's derivatives, red dyes, green dyes such as AlexaFlor; and fluorescent proteinssuch as GFP/eGFP, YFP, and chemicals, APIs, drugs and pro-drugs.

In an alternative embodiment, the nanosphere according to the invention may further comprise a homing mechanism. The presence of a homing mechanism facilitates targeted delivery of an agent by the nanosphere. The homing mechanism may be selected from the group consisting of a saccharide including lactose, galactose and manose; folic acid, an antibody fragment or a peptide sequence.

In a further embodiment of the current invention the surface of the polymer shell may be tagged with a fluorescent marker for traceability and a homing mechanism for delivery to specific target sites. The functional groups on the outer surface of the nanosphere may be suitably labelled by treating said nanospheres with fluorescein isothiocyanate (FITC), 8-anilino-1-naphthalenesulfonic acid (ANS) or any other fluorophores, for example.

Dendrimeric cross-linking systems (of the type described herein) can be used to conjugate the imaging, therapeutic and homing tags. Dendrimeric systems are used to increase the number of functional groups which can be used to conjugate any tags, imaging or therapeutic moieties. Excessive functional groups of the polymer shells can be modified with biocompatible molecules such as poly (ethylene glycol), to suppress the immunity of the device.

In one embodiment, the polymeric nanosphere according to the invention comprises one or more polymeric layers. The polymeric layers may comprise at least one polymer selected from the group consisting of polyglutamic acid, hyaluronan, alginate, PLGA, poly(caprolactone) and poly(d,l-lactide). The skilled person will appreciate that other suitable polymers could also be used. The invention therefore also provides multilayer polymeric nanospheres.

The invention also provides a process for the preparation of biodegradable hollow polymeric nanospheres comprising the steps of:
(i) providing a template comprising polymeric nanoparticles;
(ii) treating said polymeric nanoparticles with a functionalising group to produce functionalised nanoparticles;
(iii) treating said functionalised nanoparticles with a solution of one or more natural polymers, and agitating to form a polymeric coating on said nanoparticles
(iv) cross-linking said coating; and
(v) removing the template by treating said particles with a solvent.

In a particularly preferred embodiment, there is provided a process for the preparation of a natural or synthetic biodegradable polymeric hollow nanosphere comprising the steps of:
(i) providing a template comprising polymeric polystyrene beads, mesoporous silica or diatomaceous silica;
(ii) treating said template with a functionalising group to produce a functionalised template,
(iii) treating said functionalised template with a solution of one or more natural or synthetic biodegradable polymers selected from the group consisting of: collagen, elastin, chitosan, hyaluronan, alginate, polyesters, PEG-based polymers, dendritic or hyperbranched polymers, and combinations thereof, and agitating to form a polymeric coating on said template;
(iv) cross-linking said coating with a cross-linking agent selected from the group comprising a dendrimer, a hyper-branched dendritic polymer and linear polymeric system, and combinations thereof, wherein the molar ratio of reactive —COOH or —$NH_2$ groups in said dendrimer cross-linker to reactive groups —COOH or —$NH_2$ in said polymer is in the range 50:1 to 1:50; and
(v) removing the template by treating said template with a solvent.

Thus, the current invention provides for a method for producing a hollow nanosphere made of a biodegradable polymeric sphere. The use of a natural or synthetic biodegradable polymer will reduce the risk of chocking and compatibility issues. Natural biodegradable polymers disclosed herein are preferred.

The templates may comprise beads such as polystyrene beads, including substituted derivatives thereof, such as polystyrene sulfonated (PSS), carboxylated or aminated polystyrene beads; silica beads; polyester beads including polycaprolactone (PCL), polylactide (PLLA), polyethylene terephtalate (PET), polycarbonate, polybutyrate; polyamides including polyacrylamide (PAA), polyamidoamine (PAMAM); acrylic polymers including polyacrylate, polymethacrylate (PMA), polymethylmethacrylate; poly (ethylene glycol) methacrylate (PEGMA) and poly(propylene glycol)methacrylate (PPGMA), (meth)acrylic acid monomers (e.g. methacrylic acid and acrylic acid) or NHS monomers (e.g. acrylic acid N-hydroxysuccinimide ester), multi-functional vinyl monomers (e.g. PEG dimethacrylate) and cationic, anionic or amphiphilic polymers including PEI, PLL, PEG, PGA, PLGA, hyaluronan, chitosan and collagen; carbon nanotubes and metallic beads such as gold beads. The skilled person will appreciate that other suitable polymeric beads could also be used. In particular, the skilled person will appreciate that any suitable ionic particles or complexes can be used as a template to prepare the nanospheres according to the invention.

Preferably, the beads selected for use as templates in accordance with the present invention comprise beads of a size suitable for use in producing a desired size of nanospheres. Preferably, the beads templates comprise beads of a size in the range 0.05 to 5 μm.

In the preferred embodiment, the size of the nanospheres can be controlled by using polystyrene beads having a size in the range 0.05 to 5 μm as template, for example.

The skilled person will appreciate that using specific reaction conditions can produce specific sizes of nanosphere. For example, in the case of the polymerization of styrene, as described in the examples, the quantity of initiator (such as AIBN, BPO) or the solvent ratio (ethanol/water) used during polymerisation induces the production of beads having a size in the range from 0.05 to 5 μm in diameter.

In one embodiment, the template may be in the form of a dendrimer or dendritic polymeric system template. Dendrimers or dendritic polymeric systems are particularly suited to use as nanoshell and nanosphere templates, since dendrimers or dendritic polymeric systems of a wide range of sizes are accessible. For example, nanosphere size variations can be achieved by using dendrimers of different generations, e.g., $G_1$-$G_{10}$ or half generations thereof etc., as template. It will be appreciated that different shaped dendrimers or dendritic polymeric systems, e.g., spherical, globular or bowtie dendrimer templates may result in different shaped nanoshell and nanosphere.

Another advantage from use of dendrimer or dendritic polymeric system templates stems from the fact that the dendrimer or dendritic polymeric system template may have built in functionality. This is useful for facilitating polymer bonding around the dendrimer or dendritic polymeric system template.

The functionalising group may be selected from the group consisting of sulphate, a carboxyl and amine groups.

Preferably the functionalising group comprises sulphate. The term "functionalised nanospheres" as used herein means nanospheres whose surface has been modified by the attachment of a functional group. The meaning of the term "functional group" will be known to the person skilled in the art. The term "functional group" refers to specific groups of atoms which form part of molecules and which are responsible for the characteristic chemical behaviour of those molecules.

Preferably, the nanoparticles or polymeric nanosphere template may be selected from the group consisting of sulfonated polystyrene beads, polymethylmethacrylate beads, silica beads and functionalised dendrimers or dendritic polymeric bead type systems.

In a preferred embodiment, the polymeric nanoshell and nanospheres comprise sulfonated polystyrene beads. Sulfonated polystyrene beads can readily be produced on a large scale. They have a low reactivity in the process of formation of the nanospheres and can be readily removed following formation of the nanosphere.

The natural polymer for the polymeric solution may be selected from the group consisting of a protein, a polysaccharide, a cationic polymer, dendrimer and a polyacid.

Suitably, the polymeric solution comprises a polymer selected from the group consisting of collagen, gelatin, elastin, chitosan, hyaluronic acid, alginate, polyamidoamine (PAMAM), poly-l-lysine (PLL), polyethyleneimine (PEI), polyglutamic acid (PGA), poly (ethylene glycol) methacrylate (PEGMA) and poly (propylene glycol) methacrylate (PPGMA), (meth) acrylic acid monomers (e.g. methacrylic acid and acrylic acid) or NHS monomers (e.g. acrylic acid N-hydroxysuccinimide ester), multi-functional vinyl monomers (e.g. PEG dimethacrylate) and a polycarboxylic acid-polyethylene glycol-polycarboxylic acid (PPEGP) based dendrimer such as APEGA and combinations thereof. In a preferred embodiment, the APEGA dendrimer has pre-activated carboxylic acid surface functionality.

Suitably, the preferred polymeric solution comprises a natural biodegradable polymer selected from the group consisting of collagen, elastin, chitosan, hyaluronic acid and alginate.

In one aspect, the polymeric solution may comprise natural polymers in the form of a dendrimer polymer. The size of such dendrimers used as the material to build up the nanosphere layer can be varied according to need, since any particular number or combination of dendrimer generations or half generations can be used as the natural polymer substance. It will be appreciated that the size of dendrimer which may be required in this role will depend on a number of factors such as size of nanoshell and nanosphere etc.

In a preferred embodiment, the sulfonated polystyrene beads are suitably coated by dispersing them in a polymeric solution.

Different families of (multi)polymer based nanospheres may be produced in accordance with the present invention. The polymeric solution may further comprise a combination of two or more polymers. The use of a combination of two or more polymers allows the production of multi polymer nanospheres. The properties of such multi polymer nanospheres such as water solubility, surface charge ratio and porosity can be adjusted using a well defined combination of polymers.

Preferably the polymeric solution comprises a combination of polymers selected from the group consisting of chitosan/PGA; PAMAM/hyaluronan and chitosan/collagen. The skilled person will appreciate that other suitable combinations of polymers could also be used.

In a preferred embodiment of the process according to the invention, the polymeric coating is crosslinked using a ratio of cross-linker to polymer of 50:1.

In a preferred embodiment of the process according to the invention, the polymeric coating is crosslinked using a ratio of cross-linker to polymer of 1:2.

In an alternative embodiment of the process according to the invention, the polymeric coating is crosslinked using a ratio of cross-linker to polymer of 1.5:1.

Preferably, the polymeric coating is cross-linked with a cross-linker selected from the group consisting of dendrimers or dendritic polymeric systems, glutaraldehyde, carbodiimides, genepin, transglutaminase, sulfonates including methyl sulfonate or trifluoromethyl sulfonate, for example, and malemide.

Further preferably, the solid particles are cross-linked with a dendrimer or dendritic polymeric system. The dendrimer may be selected from the group consisting of polyamidoamine (PAMAM), polypropyleneimine, polyarylether and polyethyleneimine (PEI), poly-l-lysine (PLL), poly (ethylene glycol) methacrylate (PEGMA), poly (propylene glycol) methacrylate (PPGMA), polyacrylic acid and a polycarboxylic acid- polyethylene glycol-polycarboxylic acid based dendrimer such as APEGA, and combinations thereof. In a preferred embodiment, the APEGA dendrimer has pre-activated carboxylic acid surface functionality.

Thus in one particular embodiment, it is possible to use a dendrimer as a nanosphere template, as the nanoshell and nanosphere boundary or surface polymer and as crosslinker of said surface polymer to add mechanical strength and integrity to the nanosphere. It will be appreciated that the same or different types of dendrimer or dendritic polymeric systems and dendrimer generations can be used for each of these distinct roles.

Furthermore, the process according to the invention may further comprise the step of treating the polymer coated beads with a second polymeric solution comprising a polymer selected from the group consisting of polyglutamic acid, hyaluronic acid, alginate, PLGA, poly(caprolactone) and poly(d,l-lactide) to produce multilayer polymeric particles. The skilled person will appreciate that other suitable polymers could also be used.

The properties of such multi polymer nanoshells or nanospheres such as water solubility, surface charge ratio and porosity can be adjusted using a well defined combination of polymers.

Suitably, the process according to the invention further comprises removal of the templates by treating the particles with a solution suitable for dissolving the template. Typically acid solutions may be used to dissolve the template. THF is a preferred solvent for such dissolving solutions. For example, 1% acetic acid solution with THF:water (80:20 volume) may be used, prior to centrifugation to produce a nanosphere.

Preferably, the process according to the invention further comprises the step of encapsulating a biomolecule, therapeutic or imaging agent in the nanospheres. The nanospheres are sterilised prior to encapsulating the agent(s).

Preferably the therapeutic agent is encapsulated in said nanospheres by means of physical diffusion. The therapeutic agent is preferably encapsulated in the nanosphere by the dispersion of the nanospheres in a solution of specific therapeutic agent to allow diffusion of the therapeutic agent inside the cavity of the nanosphere.

Alternatively, the therapeutic agent is encapsulated in said nanospheres by means of emulsion. Molecular imaging agents may also be impregnated into the hollow cavity of the sphere by physical diffusion or emulsion.

Preferably, the process according to the invention further comprises the step of incorporating a homing mechanism on the nanosphere surface.

The invention provides a vehicle for delivering an agent to a site, comprising a nanosphere obtained by the process as described herein. The agent may be selected from the group consisting of biomolecules, therapeutic agents and imaging agents, for example.

The current invention therefore provides nanospheres for targeted delivery of an agent or agents to target cells.

DETAILED DESCRIPTION OF THE INVENTION

Figure 1:
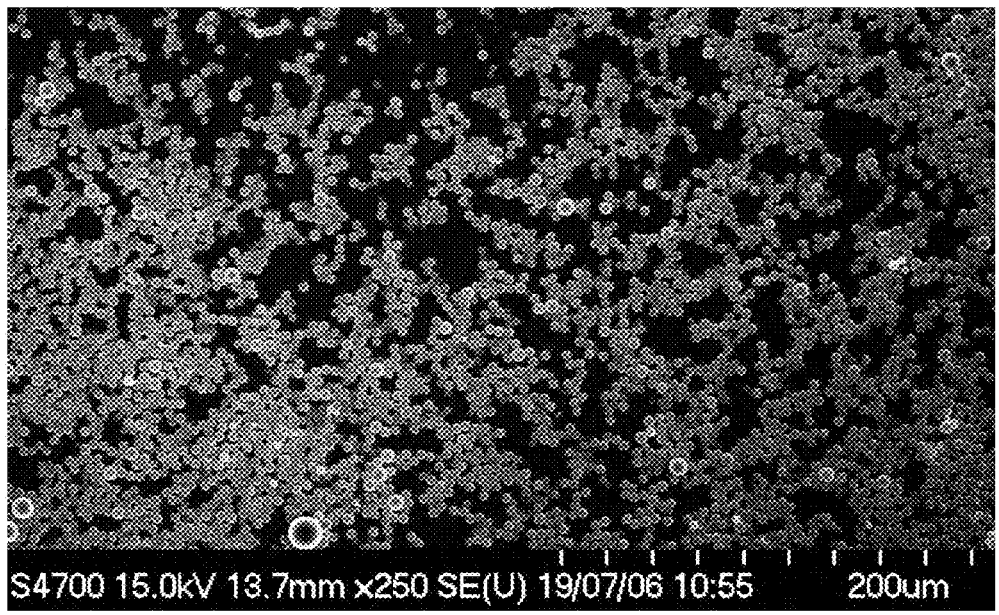
FIG. 1 shows an SEM of polystyrene nanoparticles.
Figure 2:
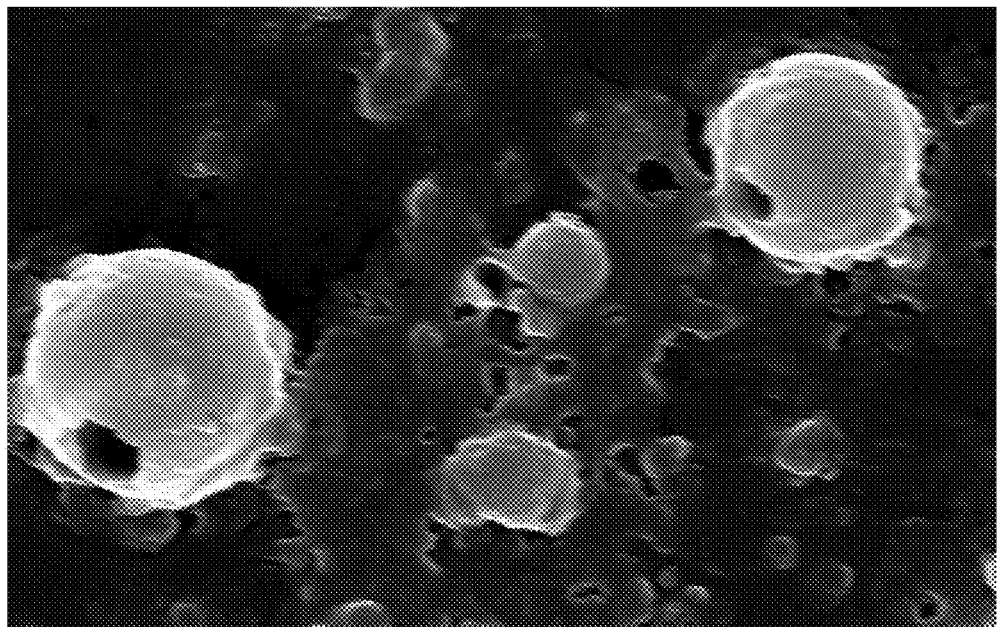
FIG. 2 shows an SEM of uncross-linked chitosan nanoshells.

The invention provides biodegradable mono-dispersed nanoshells and nanospheres and a process for the preparation of such nanoshells and nanospheres. In particular the nanospheres of the invention are suitable for use as vehicles to carry biomolecules, therapeutic agents and/or imaging agents to specific sites in the body. In order that the invention may be more readily understood, the following examples are given by way of illustration only.

Example

Materials and Methods

Styrene, poly(vinyl pyrrolidine) (Mw 36,000), absolute ethanol, methanol, azobis-(isobytyrontile) (AIBN), sulfuric acid ($H_2SO_4$), acetic acid (AcOH), tetrahydrofuran (THF), chloroform ($CHCl_3$), FITC, DMEM cell media, Hanks PBS, 3T3 fibroblast cell line, bovine serum albumin, penicillin and streptomycin, collagen I, polystyrene beads (Gentaur, PP-025-100), chitosan (low molecular weight, 90% of deacethylation), polyglutamic acid (PGA), plasmid DNA (pDNA), Gaussia Luciferase (GLuc, New England BioLabs) and PicoGreen® (Invitrogen, P11496).

Chitosan (1 L, 0.5% w/v in 1% AcOH) was purified by precipitation from a solution adjusted to pH 7 using NaOH (sodium hydroxide). The precipitated chitosan was filtered using a strainer, washed with distilled water and freeze-dried overnight. A solution at the desired concentration (0.5% w/v) was prepared in 1% AcOH.

Polystyrene (PS) beads 100 and 300 nm, phosphate buffered saline (PBS), 2-(N-morpholino)ethanesulfonic acid (MES), N-hydroxysuccinimide (NHS), trypsine EDTA, methylthiazolyldiphenyltetrazolium bromide (MTT), 1-ethyl-3-(3-dimethylaminopropyl) carbodiimide (EDC) and 2-methoxyethylamine (MEA). PS beads 510 and 1000 nm (GENTAUR, Brussels). PA series polyethylene glycol (PEG) (3400 Da) (Sunbright, NOF corporation, Japan), agar low viscosity resin kit (Agar Scientific Ltd, Essex, UK). K3E and 9NC vacutainers (BD, Dublin, Ireland), enzyme linked immunosorbent assay (ELISA) kit for human soluble P-selectin (sP-selectin), immunoassay (R&D Systems, Minneapolis, USA). Human C3a ELISA kit BD OptEIA_ from BD Biosciences-Pharmingen (San Jose, Calif., USA), fluorescein isothiocyanate (FITC), TO-PRO-3 iodide and bovine serum albumin (BSA) from Invitrogen (Dublin, Ireland). Endothelial cell growth medium-2 (EGM-2) and smooth muscle cell growth media (SmGM-2) (Lonza, England, UK), DNase free water, agarose, sodium bicarbonate, phosphate buffered saline (PBS), poly-D-glutamic acid (PGA), biocinchoninic acid assay (BCA) kit, sodium dodecyl sulfate (SDS), 30% acrylamide-bis and ammonium persulfate (Sigma-Aldrich, Ireland). Tetramethylethylenediamine (BIO-RAD (USA)) and PS beads of 500 and 1000 nm (GENTAUR, Brussels). Quant-iT™ PicoGreen® dsDNA kit, fluorescein isothiocyanate (FITC) and SimplyBlue™ (Invitrogen, Ireland), trinitrobenzene sulfonic acid (TNBSA) (Pierce, USA). Gaussia luciferase plasmid (GLP), green fluorescence protein (GFP) plasmid and gaussia luciferase assay kit (New England BioLabs (UK)) agar low viscosity resin kit (Agar Scientific (UK). $Ca^{2+}$-independent microbial transglutaminase (mTGase) (Activa®WM (Japan)), poly (2-dimethylaminoethylmethacrylate) (PDMAEMA)-block-poly ethylene glycol methyl ether methacrylate (PEGMEMA)/ethylene dimethacrylate (EDGMA), Amine terminated 4-arm Star PEG (GenKem Technology USA). branched PEI, sodium sulphate, Epichlorohydrin and Tween 20 (Sigma Aldrich Ireland).

Purification of mTGase $Ca^{2+}$-independent mTGase was purified as previously described. Briefly, the enzyme sample was dissolved in 20 mM sodium acetate buffer pH 5.8 at a concentration of 500 mg/ml and added to a glass column (1.5×30 cm) containing CM52 cation exchange resin (Whatman, UK) pre-equilibrated with the above buffer at a flow rate of 2 ml/min. The sample was washed with 2 column volumes of the same buffer and eluted by a gradient of 10 column volumes from 0 to 0.5 M NaCl. The samples were analyzed at 280 nm for protein and the pooled fractions were concentrated, dialysed into PBS and analyzed for enzyme activity using the transglutaminase colorimetric microassay kit (Covalab, UK) and purified guinea pig TGase (control) with known units of activity as standard (where 1 unit will catalyze the formation of 1 pmole of hydroxamate at pH 6.0 at 37° C. using L-glutamic acid γ-monohydroxamate as the standard).

Preparation of Monodisperse Polystyrene Nanoparticles

Styrene (20 ml) was purified by treating with 20 ml of 20% aqueous solution of sodium hydroxide at 10° C. The upper styrene layer was separated and washed with water (20 ml×5) and dried under anhydrous sodium sulphate. It was then dispersion polymerized in aqueous alcoholic medium. The medium used for the dispersion polymer is a mixture of 75 vol % absolute ethanol and 25 vol % water. Poly(vinyl pyrrolidine) (36000 Mw) (0.4-2 wt % on medium) was dissolved in the medium at room temperature. Styrene (10 wt % on medium) is added to the medium followed by azobis-(isobutyrontrile) (AIBN) (0.1-1.0 wt % on styrene). The reaction mass was stirred at 120 RPM speed at room temperature for 1 hour. Later the temperature of the reaction mixture is raised to 70° C. where it is maintained for 24 hours. The reaction mixture is diluted with double the amount of reaction mass with methanol and then centrifuged at 4000 RPM and at 8° C. temperature.

Sulfonation of Polystyrene Nanoparticles

The surface of the polystyrene particles was functionalized by sulfonating the particles. Sulfonation was carried out by treating the particles with sulphuric acid. As the polystyrene particles are hydrophobic and light-weight, they stay on the surface of the sulphuric acid medium. To get uniform sulfonation, the particles should be uniformly dispersed in the sulfonation medium. Hence, the particles (1.7 g) are first treated with 60 ml sulphuric acid and sonicated to ensure homogeneous dispersion. The particles at this time are dispersed in the medium. The temperature of the reaction mixture is raised to 40° C. It is maintained for 18 hours under stirring. The reaction mass is centrifuged many times at 6,000 to 7,000 RPM. The particles are washed with ethanol and centrifuged to get the sulfonated polystyrene particles.

Preparation of Nanoshells

The sulfonated nano-particles were dispersed in the medium (solvent) in which the natural polymer is soluble. In the present example, the particles (500 mg) were dispersed in 10 ml of 1% acetic acid solution in water. A solution of the desired natural polymer was prepared in 1% acetic acid solution at 0° C. 10 ml of the dispersed solution of the particles was then treated with 10 ml of the polymeric solution and agitated on a mechanical shaker for 24 hours at 0° C. Agitation ensures a good coating is obtained on the surface of the template, i.e. the sulfonated polystyrene bead. The mass was then centrifuged and the solid was washed with 1% acetic acid aqueous solution to remove the unreacted polymeric solution. The solid particles were separated and dispersed in 1% acetic acid solution 10 ml.

These particles can be either cross-linked at this step or later. Several coating steps can be carried out in a layer-by-layer process to obtain multi-layer particles. Crosslinking can occur before, after or during layering. The therapeutic can also be added before cross-linking.

To crosslink, the particles were treated with a 1% vol solution of Amine terminated 4-arm Star PEG in ethanol:water (80:20 by volume) at room temperature for 5 hours. A ratio of 1:1 cross-linker to polymer was used.

In a separate round-bottom flask, 77 mg (0.52 mmol, 1.7 eq) of polyglutamic acid were dissolved in 20 mL of 2-(N-morpholino)ethanesulfonic acid solution (MES, 0.05M, pH 5.5), followed by the addition of 26 mg (0.24 mmol, 0.8 eq) of N-Hydroxysuccinimide (NHS) and 40 µL (0.24 mmol, 0.8 eq) of N-Ethyl-N'-(3-dimethylaminopropyl)carbodiimide (EDC). The mixture was stirred for 5 minutes at room temperature, added to the suspension of chitosan-coated beads and agitated for 24 hours in a mechanical shaker.

To prepare the shell, the polystyrene core was removed by treating the particles in 10 ml of 1% acetic acid solution with 20 ml THF:water (80:20 by volume) for 24 hours at room temperature. The particles were washed with a 1% vol solution of acetic acid in a THF:water (60:40 by volume) solution several times. The mass was centrifuged and the shells were collected.

Alternatively, to prepare the shell, the polystyrene core was removed by treating the particles with THF. Briefly, the cross-linking mixture was diluted by a factor of three with THF and centrifuged four times at 3000 G. The collected pellets were then washed 3-4 times with THF, centrifuged and dried under vacuum.

Fabrication of Hollow Spheres

Hollow spheres were fabricated using a template based method. Briefly, the fabrication method includes three processes: coating (described above), cross-linking and dissolution of the core to obtain the hollow sphere. The sulfonated beads were dispersed in the medium (solvent) in which the natural polymer is soluble. In the present example, the beads (500mg) were dispersed in 10 ml of 1% acetic acid solution in water. A solution of the desired natural polymer was prepared in 1% acetic acid solution at 0° C. Coated beads were then cross-linked using microbial transglutaminase (mTGase). Finally, PS beads were dissolved using THF to obtain the hollow spheres.

Hollow spheres were fabricated as follows: Briefly, a 0.5 wt % solution of polymer in 1% (v/v) acetic acid was added to a colloidal solution of sulfonated PS beads of various sizes (100, 300, 500 and 1000 nm) and the mixture was then shaken for 24 hours at 4° C. PGA (1.7 equiv) in MES (0.05 m, pH 5.5) was mixed for 5 min with NHS (0.8 equiv) and EDC (0.8 equiv). This was then added to the polymer solution and the solution was stirred for 24 hours. Cross-linking reaction occurred over 24 hours. To obtain a surface negative charge on the native hollow spheres an additional 0.7 equiv PGA was added to the polymer solution during the fabrication process. Finally, to obtain hollow spheres, PS cores were dissolved with a 1% vol solution of acetic acid in a THF:water (60:40 by volume) solution and dried under vacuum to evaporate excessive solvent. The prepared nanospheres were cross-linked with various cross-linkers using EDC/NHS, 4 arm Star PEG and epichlorohydrin and optimized. Several coating steps can be carried out in a layer-by-layer process to obtain multi-layer spheres. Cross-linking can occur before, after or during layering.

Cross Linking Natural Polymer with Pre-Activated Dendrimer

The solution of natural polymer was treated with a solution of 2 mg/ml of activated functional dendrimer in DMF for 12-24 hours at 4-5 C. The cross-linked scaffold was then freeze dried and washed with 50:50 triethylamine:water or dilute ammonium hydroxide at 4-5 C for 12 hours and then water for 12 hours, finally with neutral buffer.

Dendrimeric System Development

Fluorescein (130 ml, 3 mg/ml in acetone) was added to PAMAM generation 1 (130 ml, 10.9 mg/ml in water) and mixed for 24 hours in the dark at room temperature. The reaction was monitored by thin layer chromatography. Then, the sample was extensively dialysed for 4 days, lyophilized and stored at −20° C. until use.

Surface Modification of Nanoshells

The surface functional groups of the polymer nanoshells were modified with labelling agent fluorescein isothiocyanate FITC by dispersing the nanoshells in a solution of FITC in 10 mM Tris-HCL for 24 hours at room temperature. The shells were centrifuged at 5000 rpm and 8° C. and washed 5 times with 10 mM Tris HCL solution for 10 min. The shells were then sterilized and stored.

Zeta Sizer Analysis

Zeta sizer (Malvern, Nano-ZS90) was used to characterize the polymeric coating over sulfonated PS beads. 500 nm beads were sulfonated and used for the coating experiment. of different amounts to that of a fixed quantity of PS beads was used. The ratios used were 50:1, 75:1 and 100:1 of PS to beads (µg/mg).

Alteration of Surface Charge and Function of Hollow Spheres

Spheres of all the four sizes were used for surface modifications. For neutralization, native spheres were covalently cross-linked with MEA. Briefly, 50 mg of polymer/PGA hollow spheres (0.086 mmol of carboxylic group) were dispersed in MES buffer (2-3 ml, pH 5.5) in a round bottom flask and 22.24 µl of MEA (0.258 mmol of amino group), EDC (0.172 mmol) and NHS (0.172 mmol) were then added. The mixture was stirred overnight at room temperature and dialyzed to remove the unreacted chemicals. Surface PEGylation of these hollow spheres was performed using propylamine-functionalized amino-terminated PEG. 0.043 mmol of PEG was mixed with 0.086 mmol hollow spheres with EDC (0.086 mmol) and NHS (0.086 mmol) in MES buffer (pH 5.5). The mixture was then stirred overnight and dialyzed to remove the chemicals that did not react. Surface charge was analyzed in mV using zeta sizer (NanoZS, Malvern) after surface modifications of all the spheres. Briefly, polymer was dissolved in 2% Tween 20 in PBS in the concentration of 10 mg/ml and 20% w/v sodium sulphate was added drop wise in a slight excess until it convert from a clear solution to turbid solution. The prepared nanospheres were hardened by further crosslinking with various crosslinkers including EDC/NHS-4 arm Star PEG and epichlorohydrin and optimized.

Fabrication of Different Sizes of Hollow Spheres and FITC Labelling

Spheres were observed under transmission electron microscopy (TEM) for analyzing their internal structure and size. FITC labeling was performed as described as follows: PGA was labeled with FITC prior to cross-linking step during the hollow sphere fabrication process. Briefly, a weight ratio of 1:40 of FITC to PGA was kept shaking at 4° C. for overnight. The unbound FITC molecules were removed by dialyzing. FITC labelled PGA was then used to fabricate the hollow spheres. FITC-dextran loaded nanospheres were also prepared following the same protocol.

Encapsulation of Therapeutics

The nanoshells were sterilized and dispersed in a solution of specific therapeutic agent in a small volume of 10 mL Tris-HCL and 1 mM EDTA buffer solution for 1-7 days. The therapeutic agent was entrapped inside the cavity of the shells by physical diffusion and functional interactions. The shells were centrifuged and separated. The nanoshells were finally washed with a mixture of 10 mM Tris-HCL and 1 mM EDTA buffer. The entrapment efficiency of the therapeutic agent was measured by dissolving the uncrosslinked nanoshells and measuring the released plasmid DNA against UV absorbance.

The molecule of interest may, alternatively, be encapsulated by emulsion technique. Briefly, nanoshells are solubilised in $CHCl_3$, pDNA and few millilitre of PVA solution (9%) are added and emulsified by sonication during 15 seconds and stirring for 3 hours to evaporate $CHCl_3$. The formulation mixture is then centrifuged and complexes are washed three times with ultra pure water.

Example of DNA Encapsulation

DNA encapsulation was accomplished using one of the two following protocols outlined below:

Protocol 1: An 8 mg sample of nanospheres was suspended in 1 mL of ultra-pure water. A 1-2 mL volume of THF or $CHCl_3$ and 40 µg pDNA were added, and the mixture was agitated for 3-4 hours at room temperature. The resulting sphere/pDNA complexes were centrifuged (13,000 G) and washed three times with absolute ethanol and twice with ultra-pure water.

Protocol 2: An 8 mg sample of nanospheres was suspended in 1 mL of ultra-pure water. A 1-2 mL volume of THF or $CHCl_3$ was added, and the suspension was centrifuged (13,000 G). The particles were washed three times with absolute ethanol and twice with ultra-pure water, followed by the addition of 40 µg of pDNA. The mixture was incubated over night at 4° C. and then washed three times with ultra-pure water. The sphere/pDNA complexes were diluted to the desired concentration using DMEM media.

To increase pDNA loading efficiency of hollow spheres and provide protection against endosomal degradation, polyplexes were prepared, mixing 10:1 weight ratio of a hyper branched block copolymer of poly (2-dimethyl-aminoethyl-methacrylate) (PDMAEMA)-block-poly ethylene glycol methyl ether methacrylate (PEGMEMA)/ethylene dimethacrylate (EDGMA) polymer and GLuc plasmid DNA in phosphate buffer solution pH 7.4.

Electrophoresis Gel

A 0.9% agarose gel (stained with SYBR safe) was prepared with TEA (1×) buffer and the migration was carried out under a voltage of 100 V.

Encapsulation Ratio

Following DNA encapsulation, the amount of pDNA remaining in the wash solutions was quantified using the PicoGreen® assay, which was performed according to the manufacturer's instructions.

pDNA Integrity

A 1 mg sample of sphere/pDNA complex (obtained using protocol 1) was suspended in reaction buffer (Sigma DNase1 kit). A 1 µL solution of DNase1 was added, and the mixture was incubated for 15 min. The reaction was halted by the addition of 1 µL of stop solution, and the mixture was heated to 70° C. for 10min. The integrity of the pDNA was verified using gel electrophoresis (0.7% agarose).

pDNA Release

A 1 mg sample of sphere/pDNA complex (obtained using protocol 1) was suspended in 10% FBS complemented DMEM and incubated under shaking at 37° C. At every time point, the suspension was centrifuged and a sample of the supernatant was taken. The amount of pDNA remaining in the sample solutions was quantified using the PicoGreen® assay (performed according to the manufacturer's instructions), and the percentage of release was determined by the quantity of encapsulated pDNA.

Enzymatic pDNA Release

The enzymatic release study was performed by incubating 1 mg of sphere/pDNA complex with protease (20 units per mg of complex) in 1.5 ml of buffer (10 mM sodium acetate buffer with 5 mM calcium acetate, pH 7.5) at 37° C. At every time point, the mixture was centrifuged (16,000 G) and 100 µl of sample was taken. The total volume was kept at 1.5 ml by adding 100 µl of fresh buffer. The amount of pDNA was quantified using the PicoGreen® assay.

Uptake of Nanoshells by Cells

Nanoshell uptake into cultured 3T3 cells was examined by tracing FITC fluorescence labeled nanoshells at various concentrations using confocal laser scanning microscopy (CLSM) and flow cytometry (FACS).

For CLSM, the cells were seeded on Lab-Tek chamered coverglasses and incubated with fluorescence-labelled chitosan and collagen nanoshells at a final concentration of µg/ml for 6 hours at 37° C. and 4° C. respectively. After washing the cells with PBS, the cell membrane was contrasted with 0.0005% (m/v) solution of tetramethyrhodamine (TRITC)-labelled lectin (concanavalin A-tetremethylrhodamine conjugate). The cells were fixed with a 4% solution of paraformaldehyde for 10 min and covered with 10% mowiol 488 (Clariant), 2.5% 1,4-diazabicyclo [2,2,2] octane and 25% glycerol in 0.2M Tris buffer. Confocal microscopy was performed with a Letiz microscope and a TCS True Confocal Scanner equipped with a krypton-argon laser. This can show if DNA has been encapsulated into the shell and if complexes are entering into the cell. The technique can also be used to determine the route that complexes are using and where in the cell the DNA is released.

For FACS, cultivated cells were incubated for 6 hrs with FITC fluorescence-labelled nanoshells in culture at 37° and 4° C. and were then trypsinised. Alternatively, the cells were trypsinised first followed by incubation at various nanoparticle concentrations in suspension at 37° and 4° C. for 6 hours. Nanoparticle concentrations of 5, 10 and 50 µg/ml were used. The cell membrane was stained with a TRITC-concanavalin A conjugate. The cells were analysed with a FACS calibur flowcytometer. Significance was calculated from raw data with the Wilcoxon-Mann-Whitney test. Internalisation of the nanoparticles was seen.

The morphology of the samples was studied using scanning electron microscopy (SEM) and transmission electron microscopy (TEM).

Cell Study

3T3 fibroblast cells were cultured in DMEM supplemented with 10% fetal bovine serum (FBS) and 1% penicillin-streptomycin and maintained in a humidified atmosphere containing 5% $CO_2$ and 95% air at 37° C. Cells were then seeded, 24 hours prior to the experiment, in a 96-well plate (10,000 per well) and incubated with the dendrimer-fluorescein sample (30 µmol per well) for 3 hours. Cells were washed (with PBS buffer), fixed with 4% paraformaldehyde/2% sucrose and then stained with rhodamine phalloidin. Confocal microscopy was used for this analysis.

Mass Spectral Characterisation

Sample characterisation was carried out using mass spectrometry. Mass spectral analysis involves the formation of gaseous ions from an analyte (M) and subsequent measurement of mass-to-charge ratio ($M^+$) of these ions. Mass spectrometry plays an increasingly important role in polymer analysis, because of its high sensitivity, broad dynamic range, specificity, and selectivity.

Scanning Electron Microscopy (SEM)

Scanning Electron Microscopy—Energy Dispersive X-ray Detection (SEM-EDX) images were obtained using a Hitachi S-4700 field emission microscope operating with a beam voltage of 15 kV and equipped with a backscattered electron detector. A drop of particles was placed on adhesive carbon tabs mounted on SEM specimen stubs and dried. The specimen stubs were then coated with 5 nm of gold by ion beam evaporation using an Emitech K550 coating system.

Transmission electron microscopy (TEM)

TEM measurements were performed using a Hitachi H-7500 microscope. The TEM samples were prepared by depositing a diluted particle suspension on a carbon-coated copper grid, followed by air-drying.

Figure 26:
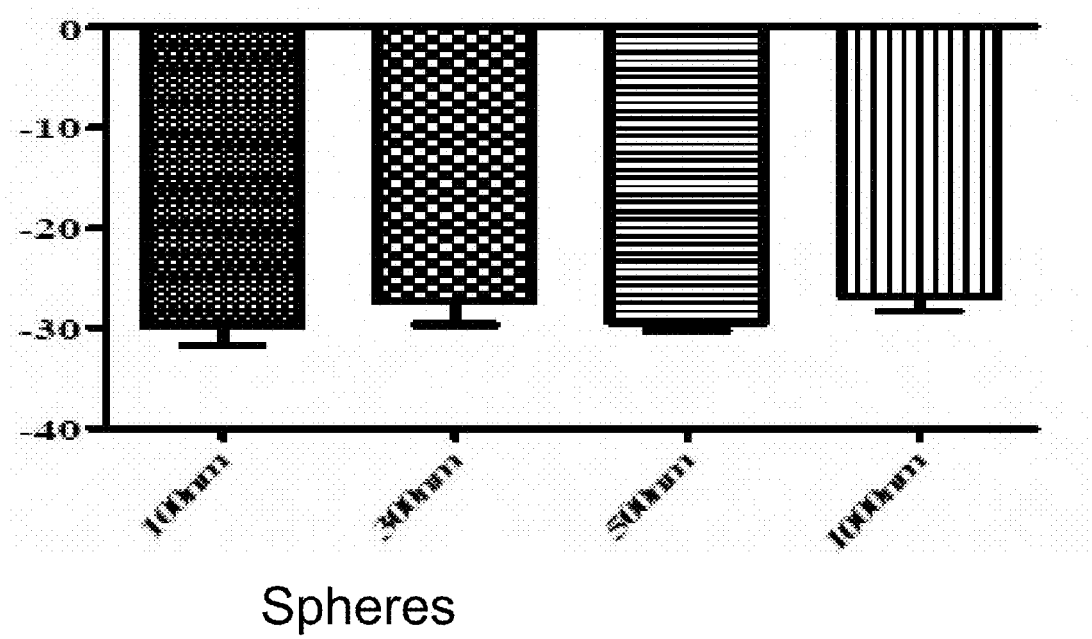
FIG. 26 shows Zeta potential analysis of 100, 300, 500 and 1000 nm hollow spheres in mV.

Hollow spheres of the four different sizes were observed under transmission electron microscopy (TEM) (Hitachi H7500) and scanning electron microscopy (SEM) (Hitachi S-4700). Additionally, ultrastructure of solid spheres of was observed under TEM. Further visualization of internalization was obtained by TEM. Cells were incubated with 50 µg of spheres for 24 hours. The TEM images showed transparent and squeezed hollow spheres (FIG. 26). The sizes of the hollow spheres as estimated from their TEM images are 100±13, 300±26, 500±34, 1000±90 nm. The surface charge of all the sizes of hollow spheres as measured using zeta sizer were in the range of −20 to −27 mV (FIG. 26). This demonstrates that these hollow spheres can be used as a potential reservoir system for various therapeutic molecules.

Fourier Transform Infrared (FTIR) Analyses

The infrared spectra were obtained using a Shimadzu FTIR-8200 Fourier Transform Infrared Spectrophotometer. The samples were analysed without any preparation.

Blood Compatibility

A major challenge for the systemic delivery of synthetic vehicles for gene delivery is their lack of stability in the blood stream, their degradation, and clearance by the reticuloendothelial system, which makes the elucidation of their interaction with blood components essential. Several interactions with the family of spheres were investigated to determine the potential systemic delivery in vivo of the hollow spheres.

Characterisation of Sulfonated Polystyrene Beads

Figure 10:
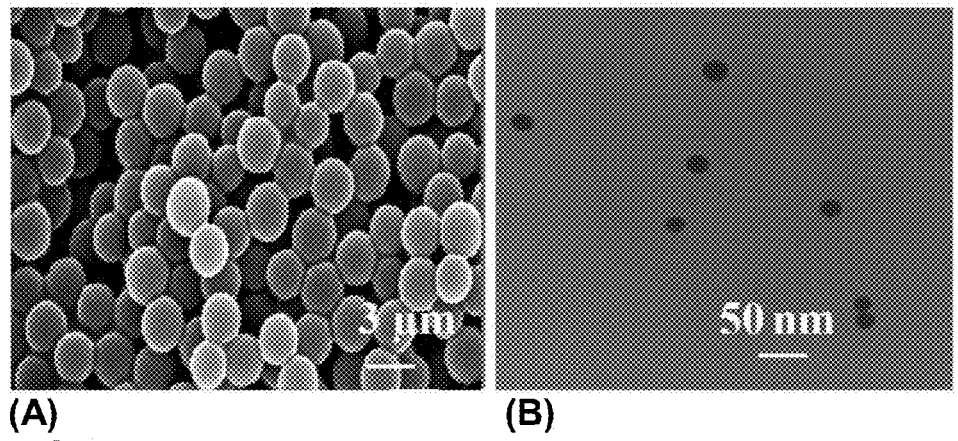
FIG. 10 shows SEM (A) and TEM (B) images of polystyrene beads. SEM (A) and TEM (B) images of polystyrene beads.
Figure 11:
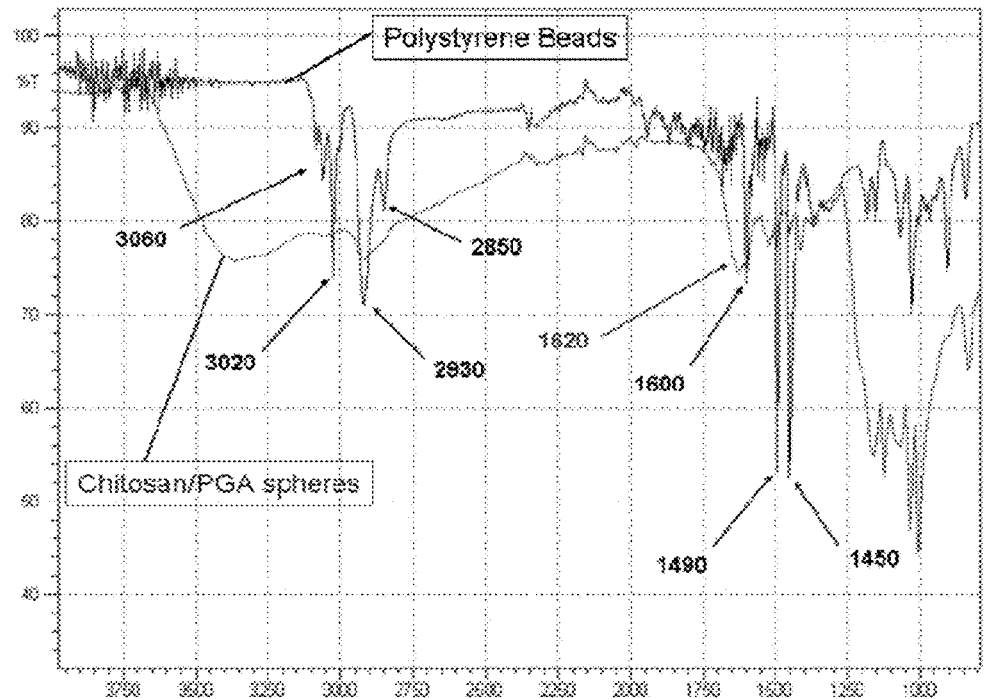
FIG. 11 shows FTIR spectra of polystyrene and sulfonated polystyrene beads. FTIR spectra of polystyrene and sulfonated polystyrene beads.

Each step of the hollow-sphere production process was characterised using one or more techniques such as SEM, TEM and FTIR. FIG. 10 is an electron micrograph depicting the structural morphology of the beads. The particles are consistent in shape and size with a mean diameter of 300 nm. The sulfonated beads were evaluated using FTIR. FIG. 11 contains infrared spectra of the polystyrene beads before and after sulfonation. The appearance of characteristic peaks at 3300 $cm^{-1}$ and 1200 $cm^{-1}$ indicates that the beads were significantly sulfonated.

Study of Effect of Ratios of Cross-Linker to Polymer

To illustrate the property differences induce by the particular crosslinker used, the effect of the ratio of cross-linker to polymer used for cross-linking the polymeric nanoshells on the physical properties of the nanoshells was investigated. Table 1 provides a summary of the cross-linker to polymer ratios investigated.

TABLE 1

A summary of the cross-linker to polymer ratios investigated

| Batch n° | $NH_2$ group (equivalent) | COOH group (equivalent) | EDC/NHS (equivalent) |
|---|---|---|---|
| 1 | 1 | 4 | 0.8 |
| 2 | 1 | 3 | 0.8 |
| 3 | 1 | 2 | 0.8 |

Figure 12:
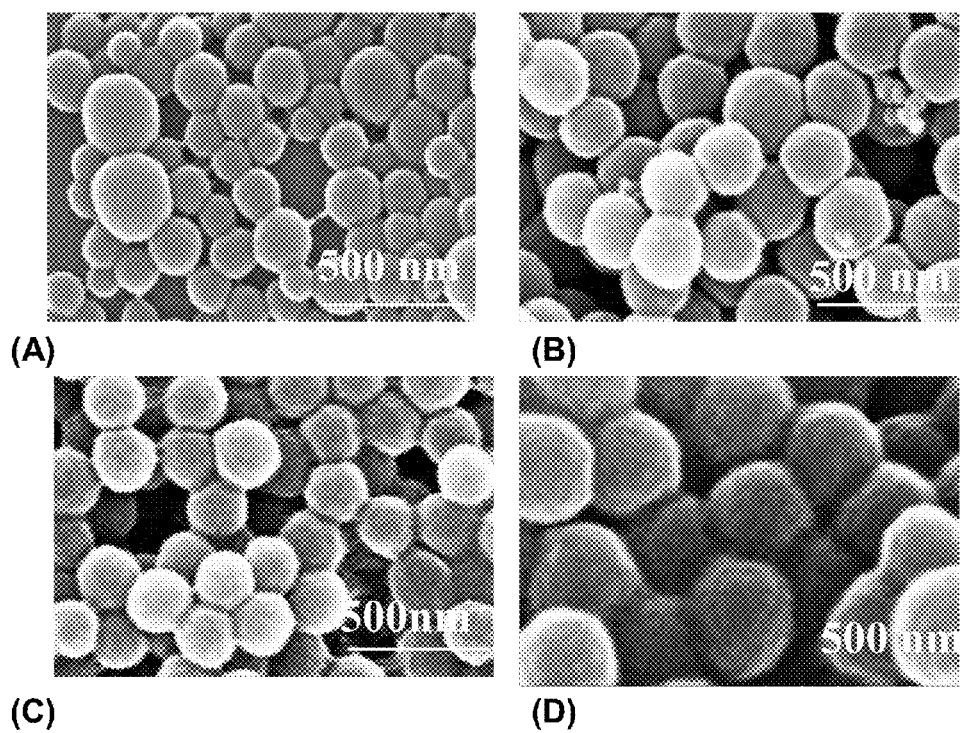
FIG. 12 shows SEM images of sulfonated polystyrene beads coated with varying concentrations of chitosan and sulfonated polystyrene beads coated by chitosan cross linked with PGA. SEM images of sulfonated polystyrene beads coated with 50 mg of chitosan (A), 125 mg (B), 250 mg (C) and 375 mg (D)

As discussed above, the sulfonated beads were coated with chitosan solution. At low concentrations, SEM micrographs revealed discrete chitosan-coated beads (FIG. 12A), but when the concentration was increased, the polymer covered the beads. Because of this high concentration of chitosan, the structure appears to look like aggregated beads resulting, after cross-linking, in a scaffold-like structure (FIG. 12C, 12D), which is undesirable in the present objective.

Figure 3:
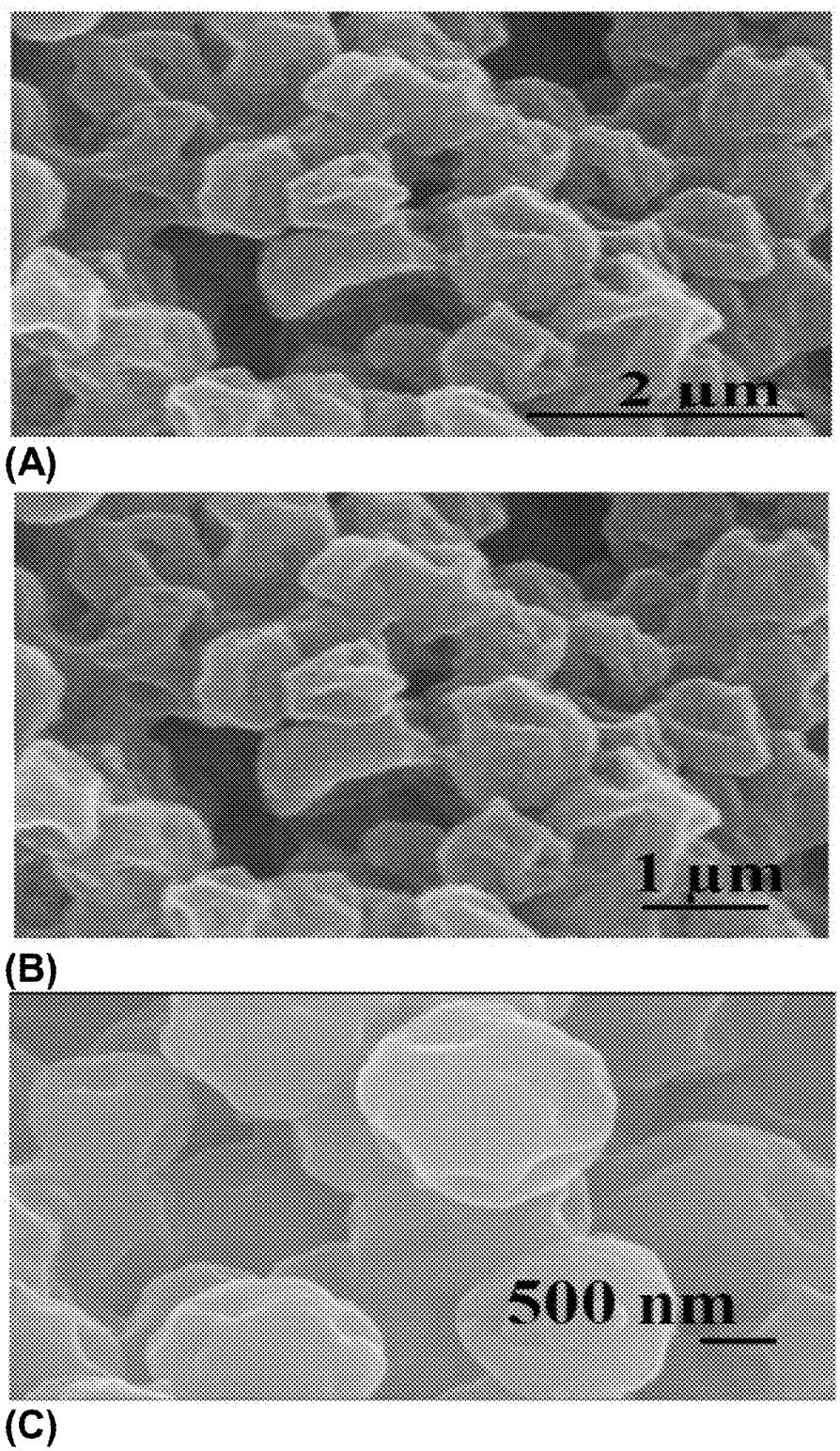
FIG. 3 shows SEM analysis of nanoshells from batches 1 to 3 from Table 1. SEM analysis (left hand side) of nanoshells from batch no 1 (A), batch no 2 (B) and batch no 3 (C)
Figure 4:
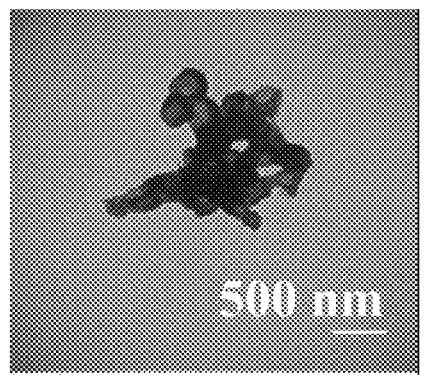
FIG. 4 shows TEM analysis of nanoshells from batches 1 to 3 from Table 1. TEM analysis of nanoshells from batch no 1 (A), batch no 2 (B) and batch no 3 (C) of Table 1.
Figure 4:
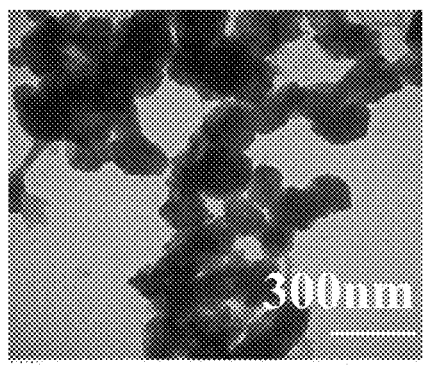
Figure 4:
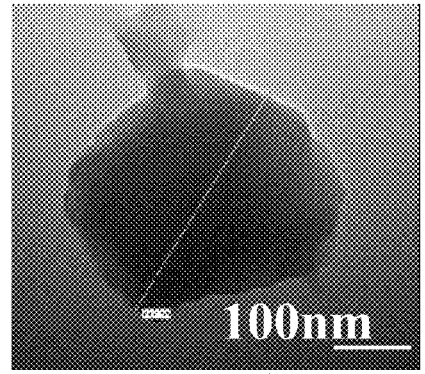
Figure 13:
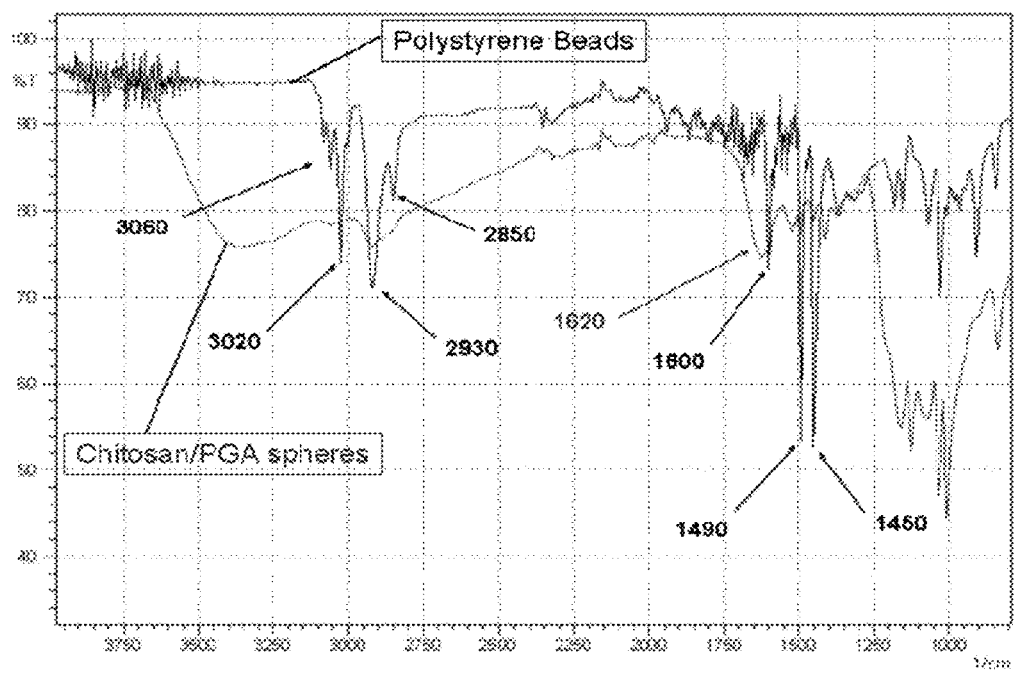
FIG. 13 shows FTIR spectra of polystyrene and shells. The tagged peaks are characteristic of polystyrene beads. FTIR spectra of polystyrene (blue) and shells (purple). The tagged peaks are characteristic of polystyrene beads.

After coating, the polymeric layer was cross-linked using EDC/NHS and the sulfonated beads were removed to obtain hollow spheres. The presence of the hollow core was confirmed by the disappearance of the characteristic peaks of polystyrene beads (FIG. 13) and by the flat shape of the sphere (FIG. 3A, 3B, 3C) due to the high vacuum in the SEM chamber. The results show that when the cross-linker to polymer ratio is increased (equivalent quantity of COOH group decreases) the rigidity of the membrane increases. In fact, nanoshells obtained with 1/4 ($NH_2$/COOH) ratio are totally crushed (FIGS. 3A, 4A). Nanoshells with 1/3 ratio are less crushed and look like "deflated balls" (FIGS. 3B, 4B). From these results it is concluded that the optimum ratio of cross-linker to polymer to produce well-defined nanoshells is 1/2 ($NH_2$/COOH) (FIGS. 3C, 4C) as shown by the electron microscopy images in FIG. 3.

TNBSA Assay and SDS-PAGE for Cross-Linking

Figure 27:
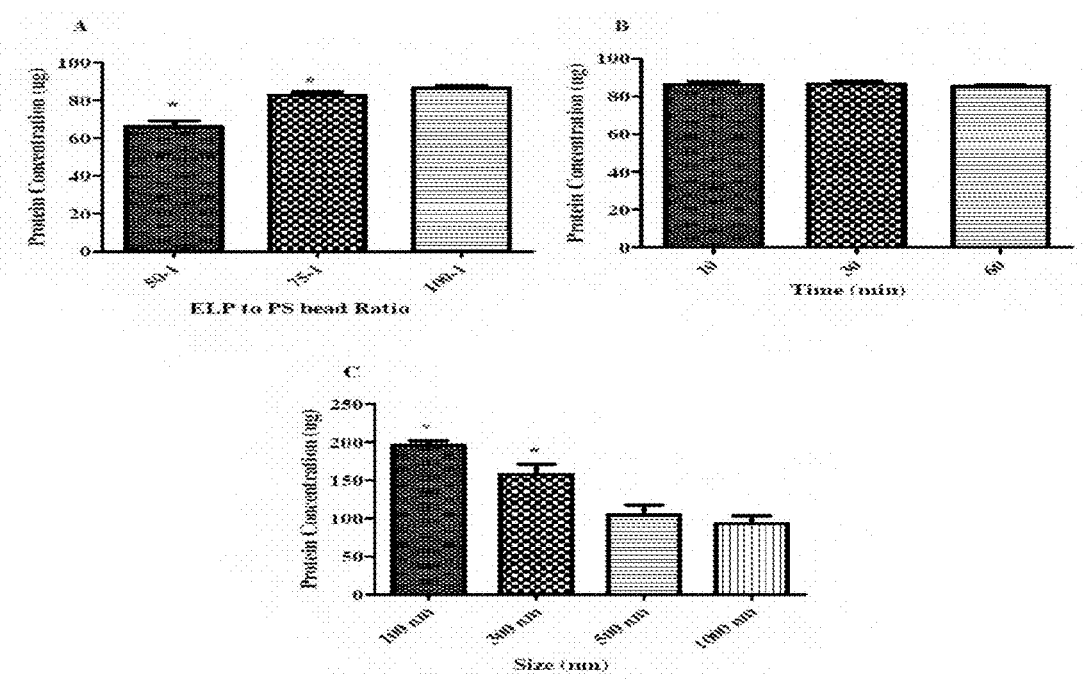
FIG. 27 shows TNBSA analysis of mTGase cross-linked hollow nanospheres relative to controls. TNBSA analysis of cross-linking of hollow nanospheres with various amounts of mTGase enzyme units having glutaraldehyde as a positive control. Statistical significance was determined by one way ANOVA (n=9, p<0.05)

The cross-linking of hollow spheres with mTGase was illustrated using TNBSA, a hydrophilic modifying reagent for the detection of primary amines in samples containing amino acids, peptides or proteins. TNBSA assay was performed to characterize the mTGase cross-linking of hollow spheres and also to quantify the amount of free amino groups available on the surface. The data indicate that mTGase cross-linking leaves a higher proportion of free amino groups than that of glutaraldehyde (FIG. 27).

Effect of Degree of Crosslinking on Physical Properties of the Nanosphere

Figure 5:
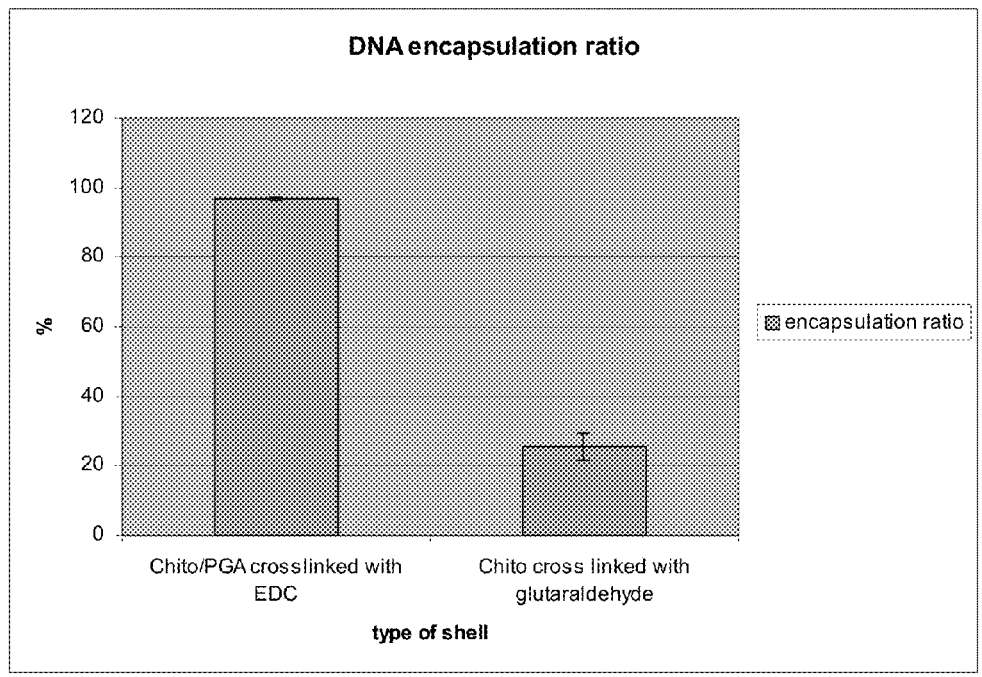
FIG. 5 shows the DNA encapsulation ratio comparison between chitosan nanoshells crosslinked with glutaraldehyde and chitosan/PGA nanoshells.

The nanospheres according to the invention illustrate that cross-linking of the polymers forming the nanosphere improves the stability and mechanical integrity of the nanosphere. The degree of crosslinking can affect various physical properties of the nanosphere such as the permeability of the sphere wall, the rate of degradation of the sphere, and the rate of release of agents encapsulated within the sphere for example. Thus, FIG. 5 shows the DNA encapsulation ratio comparison between chitosan nanospheres crosslinked with glutaraldehyde and chitosan/PGA nanospheres. Different cross-linkers and ratios of cross linker display difference release rates.

Dendrimeric System Development

Figure 6:
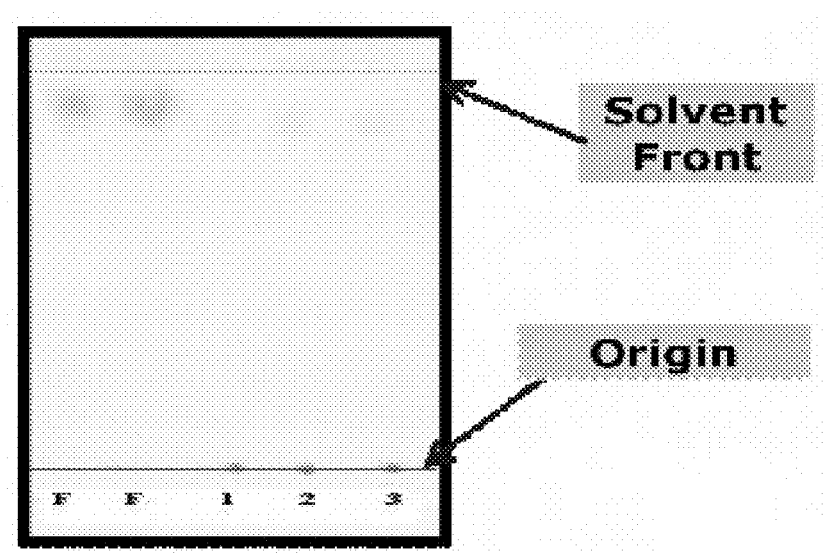
FIG. 6 shows that conjugated FITC-PAMAM G1 does not migrate from the origin using TLC.

The fluorescein-dendrimer reaction was monitored using thin layer chromatography. The TLC plate is shown in FIG. 6. The objective was to link one FITC probe onto the dendrimer in order to be able to track it without changing its properties. Due to the excess of free amine groups (7 per molecule), the conjugate (samples 1, 2 & 3) barely moved from the origin. The unbound FITC (F) probe migrates near to the solvent front.

Figure 7:
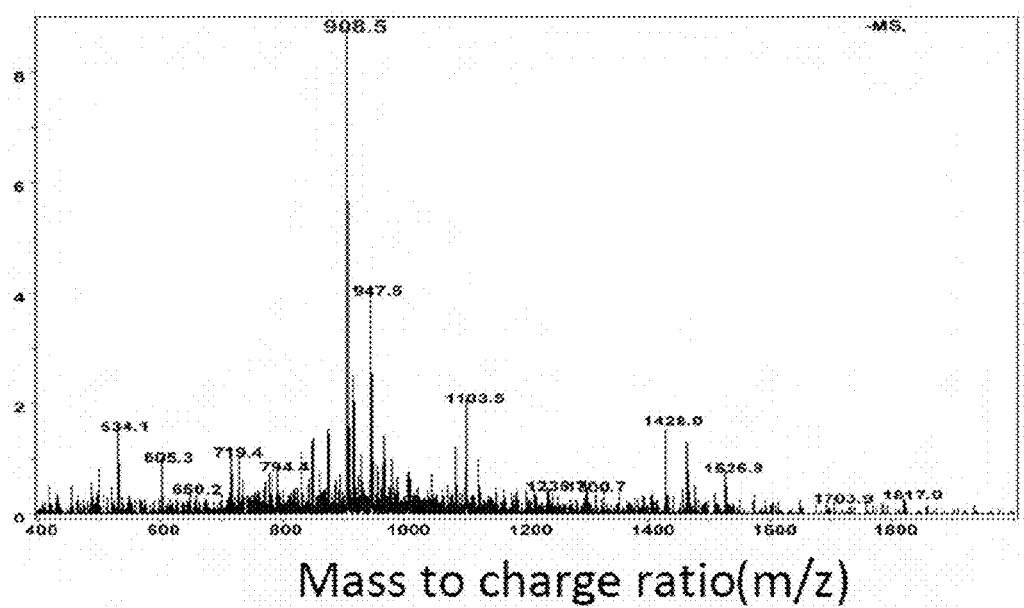
FIG. 7 shows mass spectra of FITC labelled PAMAM in negative ion mode by flow injection analysis. Mass spectra of FITC labelled PAMAM in negative ion mode. Analysis carried out by flow injection analysis with an Agilent ion trap (6330 model)

Mass spectrometry was used to characterise the conjugate. The mass spectra (FIG. 7) revealed the presence of a peak at 908.5. The 0.5 difference in mass to charge ratio (m/z) between the neighbouring peaks (isotopic difference) indicates that the sample is 'doubly charged' (z=2). The visible molecular weight of the complex is 908.5 doubled plus two protons or 1819 (908.5*2+2). This value matches the theoretical molecular weight of 1819.25 (the sum of the molecular weight's of PAMAM G1 and FITC) confirming that the fluorescein-dendrimer conjugate was formed correctly.

Figure 8:
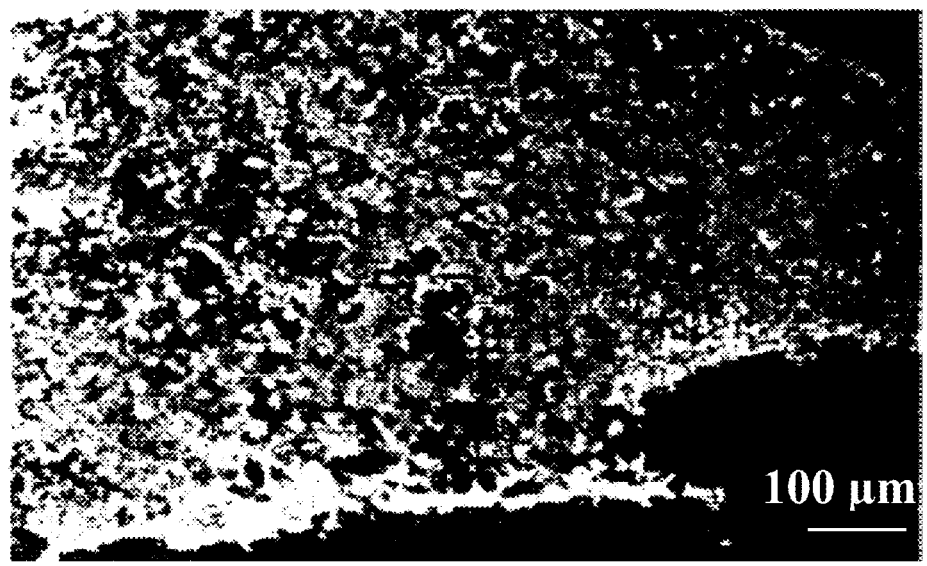
FIG. 8 shows confocal micrographs of 3T3 fibroblasts stained with RP (red) through RP filter (left hand side) and FITC filter (right hand side). Confocal micrographs of 3T3 fibroblasts stained with RP (red) through RP filter (left hand side)
Figure 9:
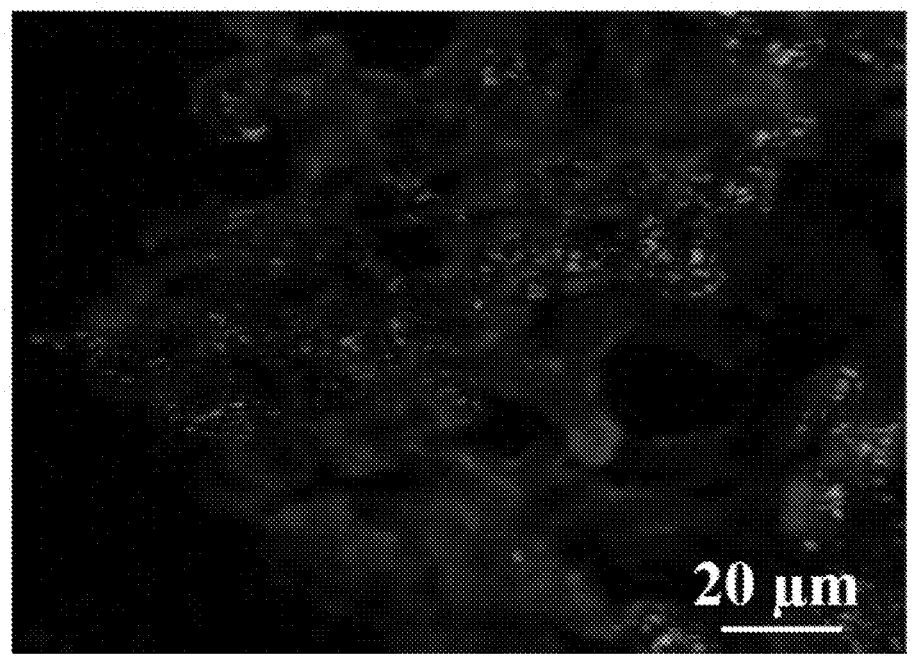
FIG. 9 shows confocal micrograph of 3T3 cells stained with RP and incubated with FITC-PAMAM complex. Confocal micrograph of 3T3 cells stained with RP and incubated with FITC-PAMAM complex.

Confocal microscope studies were carried out without (FIG. 8) and with (FIG. 9) FITC labelled PAMAM. Due to their positive charge ratios (FIG. 9) an efficient uptake of the complexes into the cells was seen. This result was confirmed by the absence of green fluorescence (FITC) as seen in the control micrographs (FIG. 8).

Zeta Size Analysis

Figure 28:
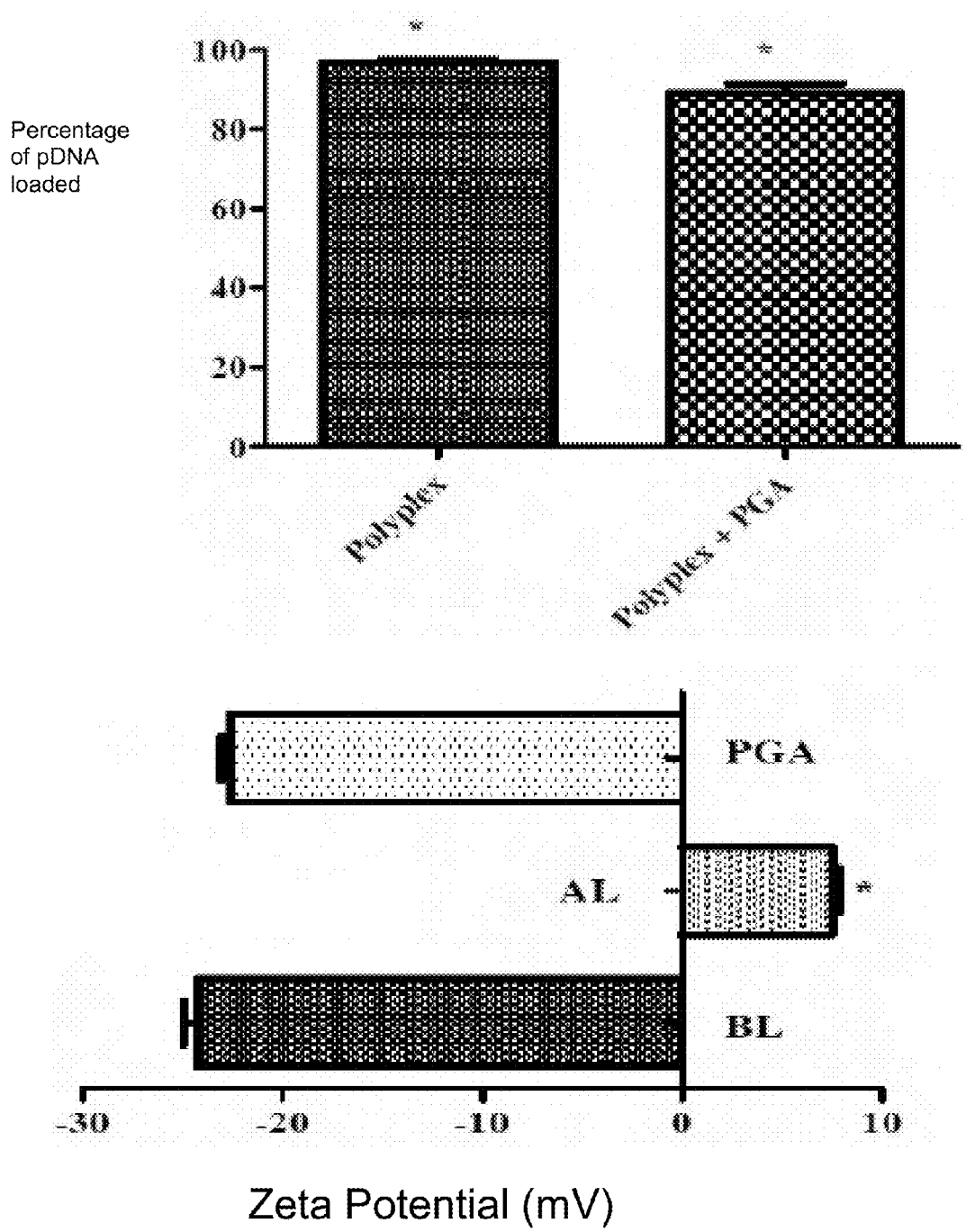
FIG. 28 shows PicoGreen® assay and zeta potential analysis of polyplex loading inside hollow sphere. PicoGreen® assay and zeta potential analysis of polyplex loading inside hollow sphere. (A) PicoGreen® assay showing difference of loading percentage by the direct quantification of polyplex and treating the polyplex with PGA for quantification (B) zeta potential analysis of hollow spheres before loading (BL), after loading (AL) and after treatment with PGA to validate PGA method for quantification. Statistical significance was determined by one way ANOVA and student's t-test (n=3, p<0.05)
Figure 29:
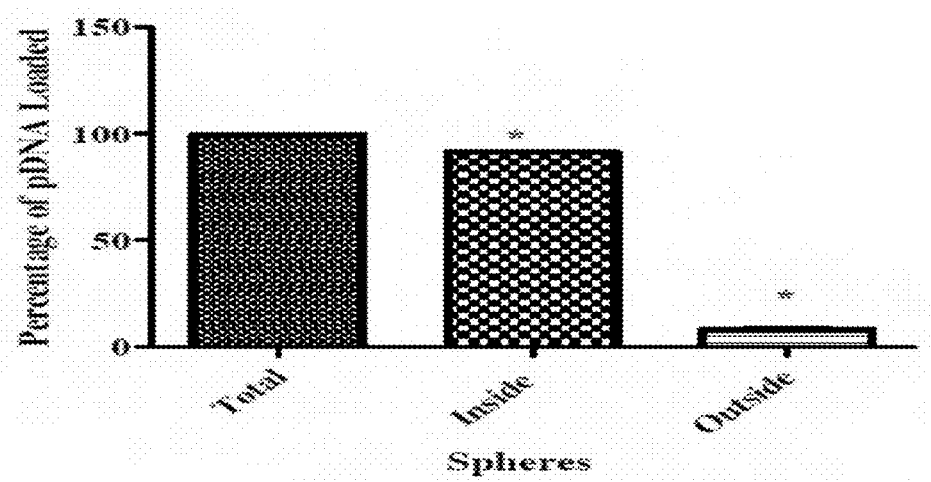
FIG. 29 shows PicoGreen® assay showing amount of polyplex loading outside spheres and inside the hollow spheres after treating the spheres with PGA. PicoGreen® assay showing amount of polyplex loading outside hollow spheres and inside the hollow spheres after treating the spheres with PGA. Statistical significance was determined by one way ANOVA (n=3, p<0.05)

Zeta potential analysis of 1000 nm hollow spheres after loading showed an increase in surface charge from negative to a value near to +7 mV, indicating the presence of polyplexes on their outer surface (FIG. 28). The amount of pDNA on the outer surface was found to be 8-10% of the total amount loaded as assayed by Picogreen® (FIG. 29). A similar trend was found in all other spheres. The polyplex loaded hollow spheres were then analyzed under TEM, where they appeared to be more compact and dark than that of unloaded hollow spheres (FIG. 30E).

Zeta sizer (Malvern, Nano-ZS90) was used to characterize the polymeric coating over sulfonated PS beads. 500 nm beads were sulfonated and used for the coating experiment. of different amounts to that of a fixed quantity of PS beads was used. The ratios used were 50:1, 75:1 and 100:1 of PS to beads (µg/mg). Size and zeta potential of the coated and PS beads were analyzed to prove the coating. In addition, surface charge of hollow spheres was determined. The surface charge of all the sizes of hollow spheres as measured using zeta sizer were in the range of −20 to −27 mV (FIG. 26).

Encapsulation of Therapeutics
pDNA Encapsulation Efficiency and Release

Figure 14:
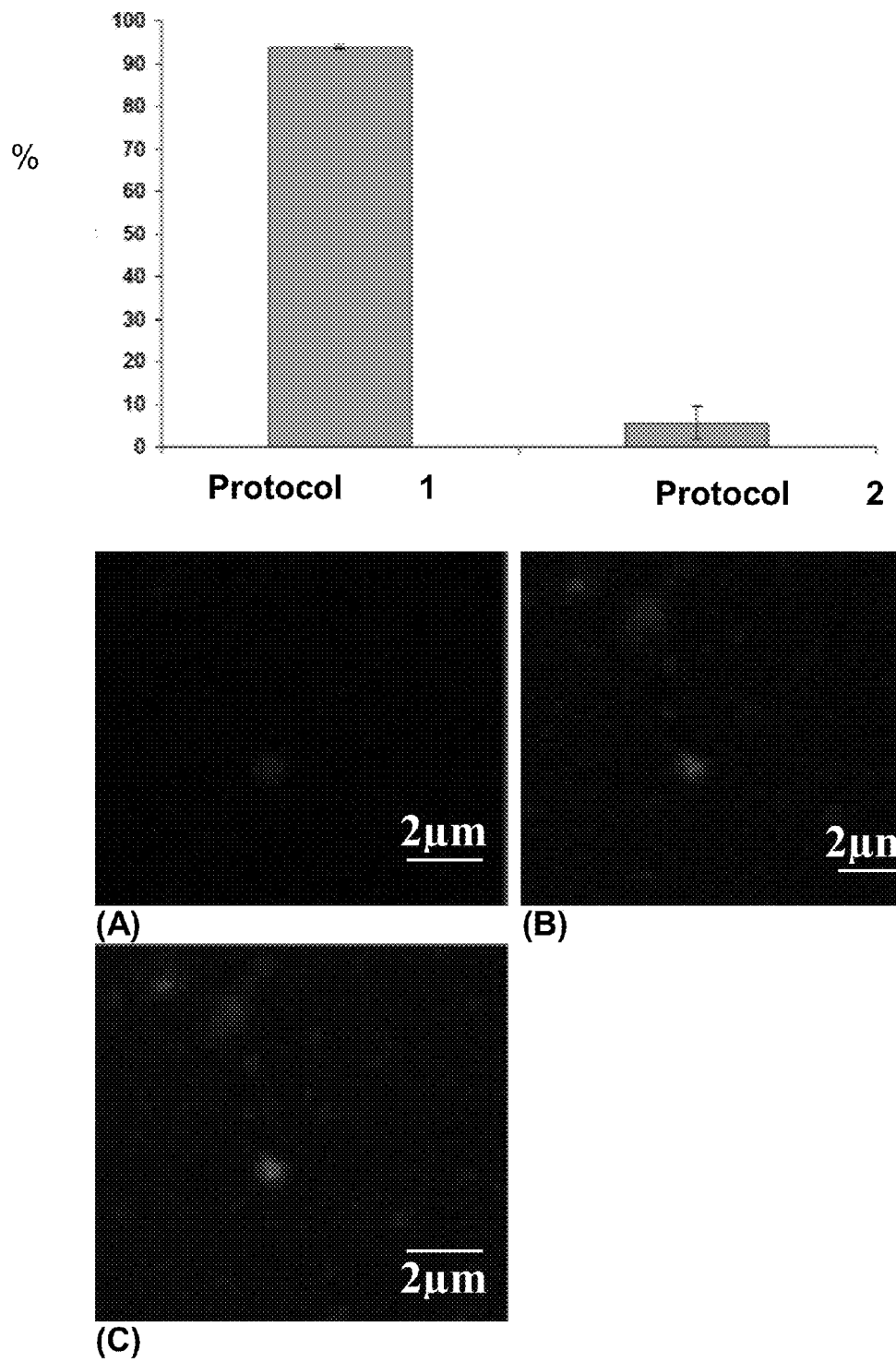
FIG. 14 shows effect of the protocol (1 or 2) on the encapsulation ratio and confocal micrograph of ethidium bromide labeled pDNA. Effect of the protocol (1 or 2) on the encapsulation ratio and confocal micrograph of Ethidium bromide labeled pDNA (red A) encapsulated into FITC labeled shells (green B). The resulting complexes appear yellow (C)
Figure 15:
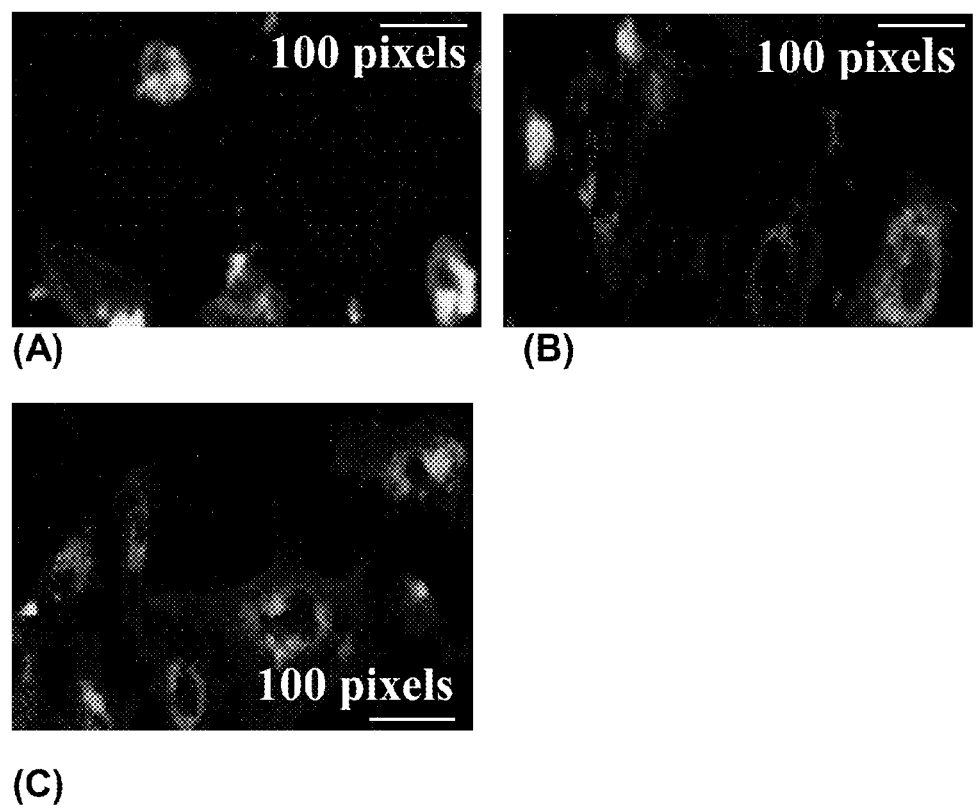
FIG. 15 shows fluorescence microscopic images of HUVEC with different sizes of negatively charged hollow spheres at 12 hours. Fluorescence microscopic images of HUVEC with different sizes of negatively charged hollow spheres at 12 hr (A) 200 nm (B) 400 nm (C) 600 nm hollow spheres with HUVEC.

Two encapsulation protocols were attempted. The second method described above (protocol 2) involved the addition of the pDNA at the end of the process in an attempt to encapsulate the pDNA by diffusion. This method was unsuccessful due to the low permeability of the membrane. However, when the pDNA was added during the emulsion step according to the initial process (protocol 1), the encapsulation was more efficient. The results showed that the polymeric shell was capable of encapsulating approximately 92% of the pDNA (FIG. 14). The polymeric shell pDNA complex was also confirmed by confocal microscopy which showed collocation of FITC-labelled polymeric shell (indicated by green areas on the micrograph) and ethidium bromide labelled pDNA (indicated by red areas on the micrograph) as shown in FIG. 14 B. The fluorescence microscopy along with FACS study demonstrated the uptake behavior of HUVEC and HVSMC. The uptake of spheres was seen within 6-12 hrs of incubation period (FIG. 15). A yellow color (mix of green and red) represented the colocalisation of spheres inside the cell. The brightness of this yellow color showed the level of internalization.

Figure 16:
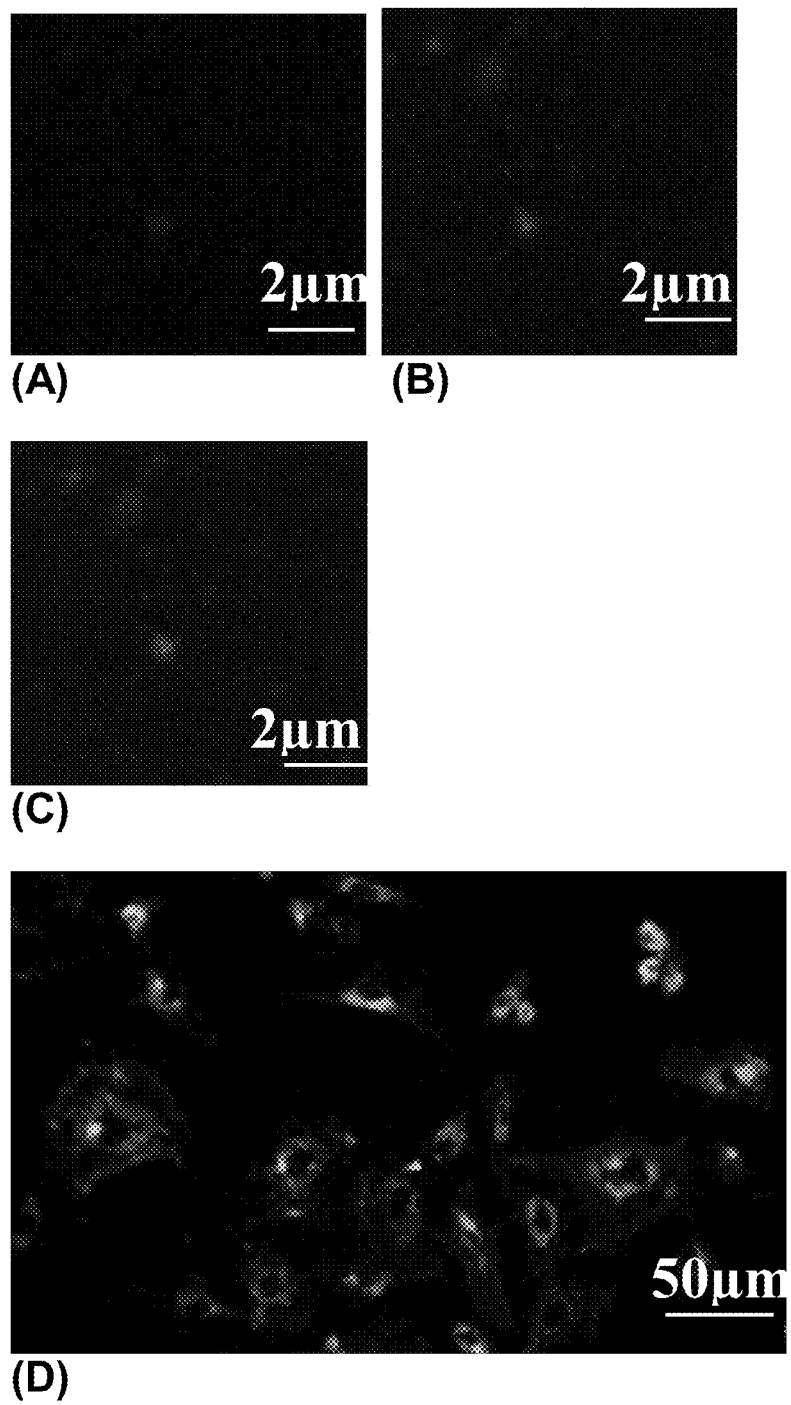
FIG. 16 shows confocal micrographs of Ethidium bromide labeled encapsulated pDNA. (A) confocal micrograph of Ethidium bromide labeled pDNA (red A) encapsulated into FITC labeled spheres (green B). The resulting complexes appear yellow (C) (scale bar: 2 μm), (B) confocal micrograph of rhodamine (red) stained endothelial cells (HUVEC) incubated 12H with 500 nm FITC labelled spheres (green) (scale bar: 50 μm)
Figure 17:
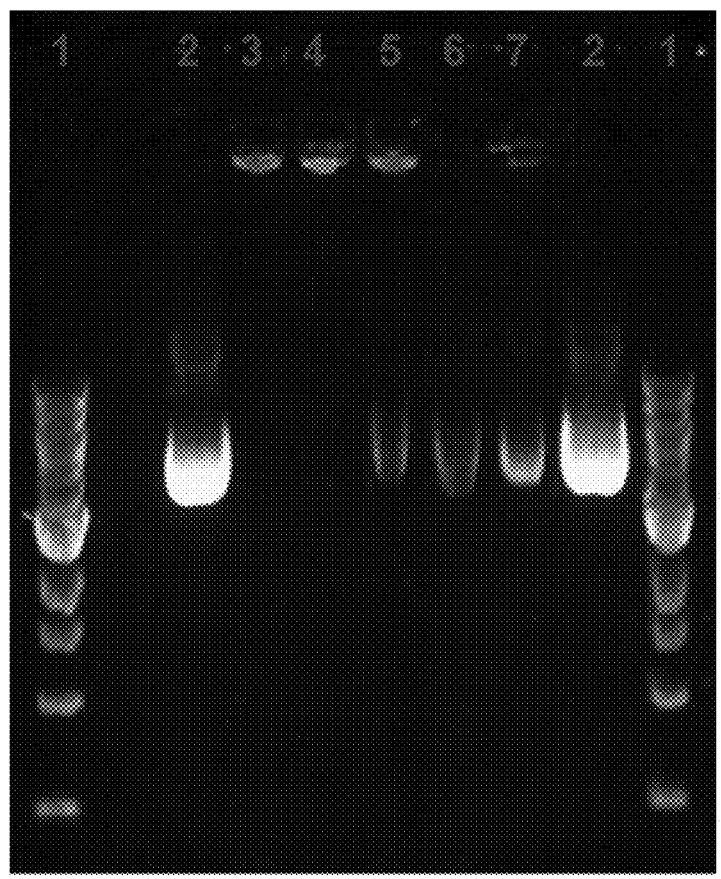
FIG. 17 shows electrophoresis gel with ladder (1 kb) of encapsulated pDNA using protocol 1 and protocol 2. Electrophoresis gel (0.9% agarose) with ladder (1 kb) (1), pDNA (2), Shells (3), pDNA encapsulated into shell by using protocol 1 and after wash (4), pDNA encapsulated into shell by using protocol 1 and before wash (5), protocol 1 washed phase (6) and protocol 2 (7)
Figure 18:
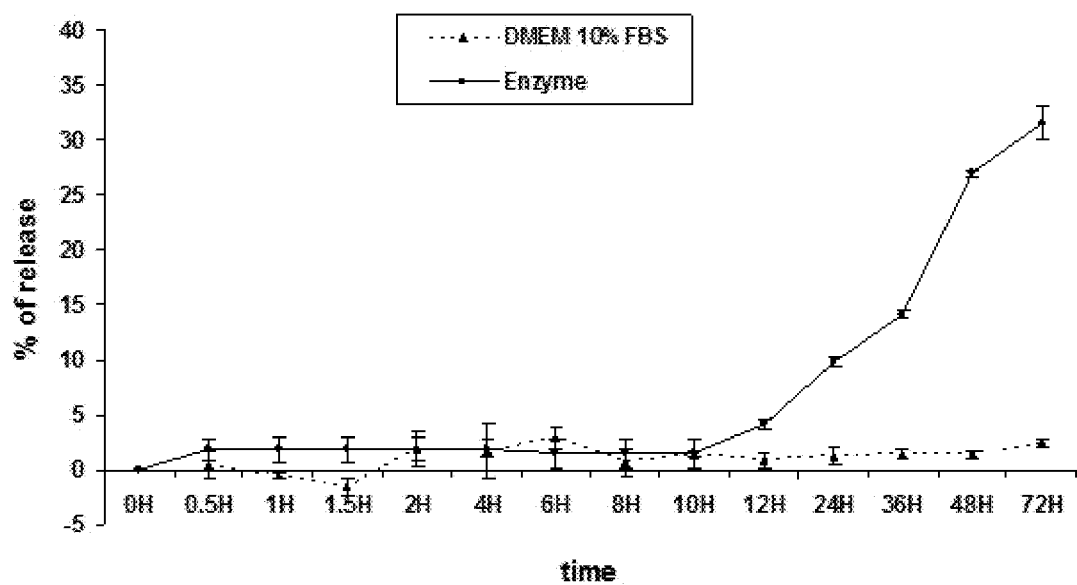
FIG. 18 shows release of protocol 1 encapsulated pDNA in FBS complemented media and in presence of protease (enzyme) over a 72-hour time period. Release of protocol 1 encapsulated pDNA in FBS complemented media (DMEM 10% FBS) and in presence of protease (enzyme) over a 72-hour time period.
Figure 19:
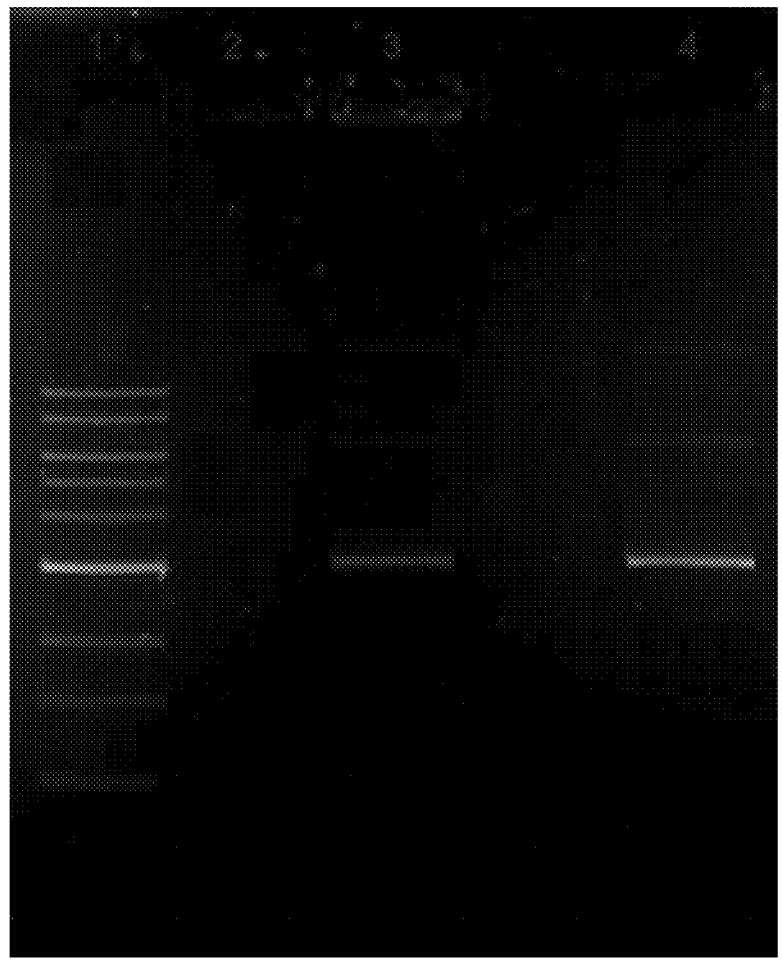
FIG. 19 shows electrophoresis gel after enzymatic release with Ladder (1 kb) up to 72 hours. Electrophoresis gel (0.9% agarose) after enzymatic release with Ladder (1 kb) (1), 6 H incubation time (2), 72 H incubation time (3), native pDNA (4)
Figure 30:
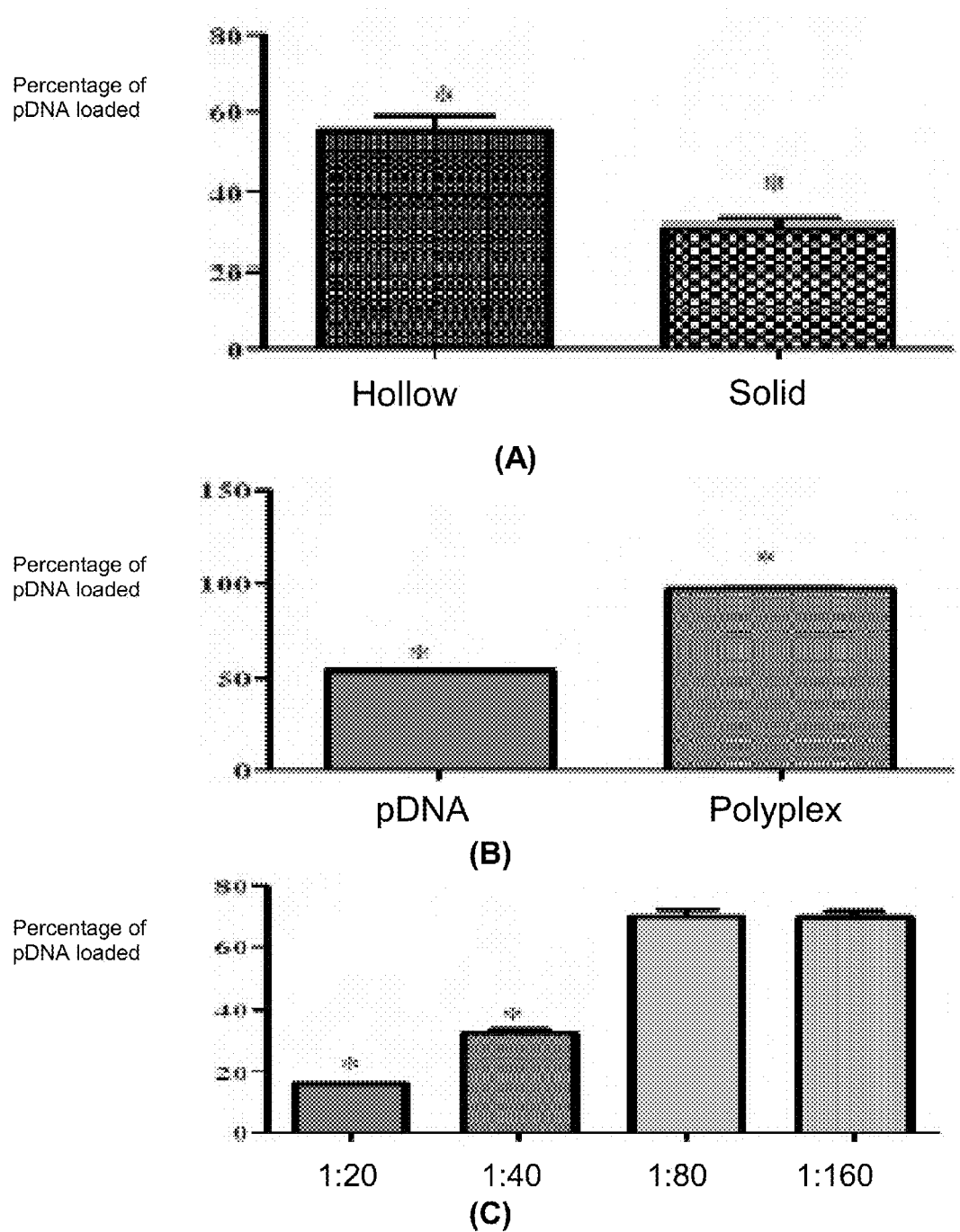
FIG. 30 shows a comparison of pDNA and polyplex loading behavior of hollow spheres and solid spheres. pDNA and polyplex loading behavior of hollow spheres (A) comparison of pDNA loading efficiency of hollow spheres and solid sphere, (B) pDNA loading efficiency of hollow spheres using pDNA alone and polyplex, (C) loading efficiency of 1000 nm hollow spheres with varying ratios of polyplex to sphere, (D) loading efficiency of all four different sizes of hollow spheres and (E) TEM image of 1000 nm hollow sphere loaded with polyplex. All the data are represented as the mean±standard deviation (n=3). Statistical significance difference was determined using one-way ANOVA and student's t-test. * indicates a statistically significant difference between samples with p<0.05.
Figure 30:
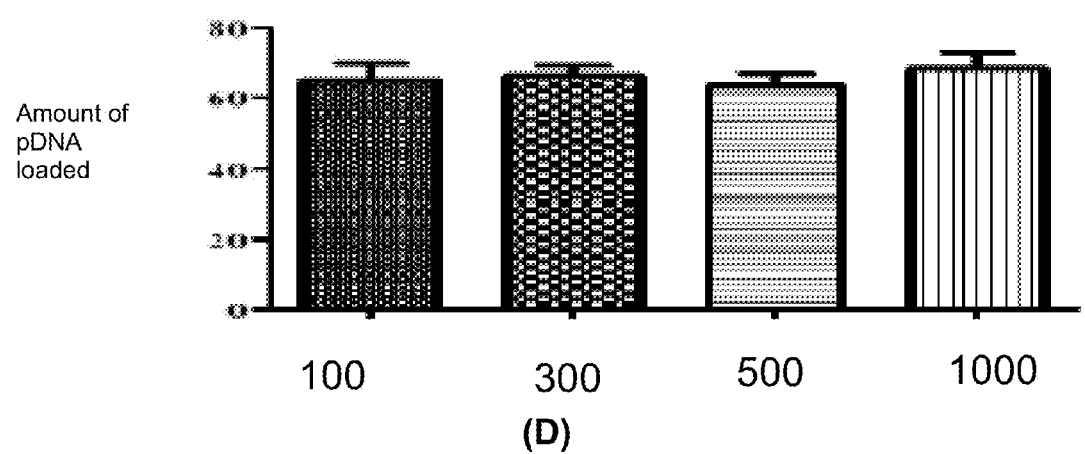
Figure 30:
Figure 31:
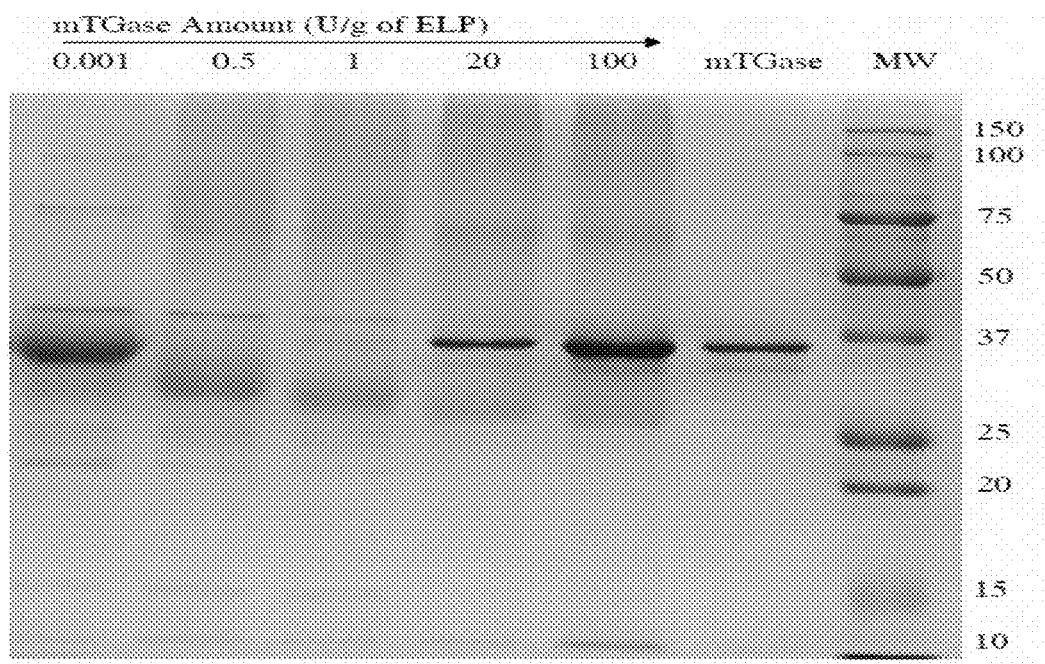
FIG. 31 shows SDS-PAGE showing the gradual cross-linking of hollow sphere with increase in mTGase amounts. The gel was stained using coomassie blue.
Figure 32:
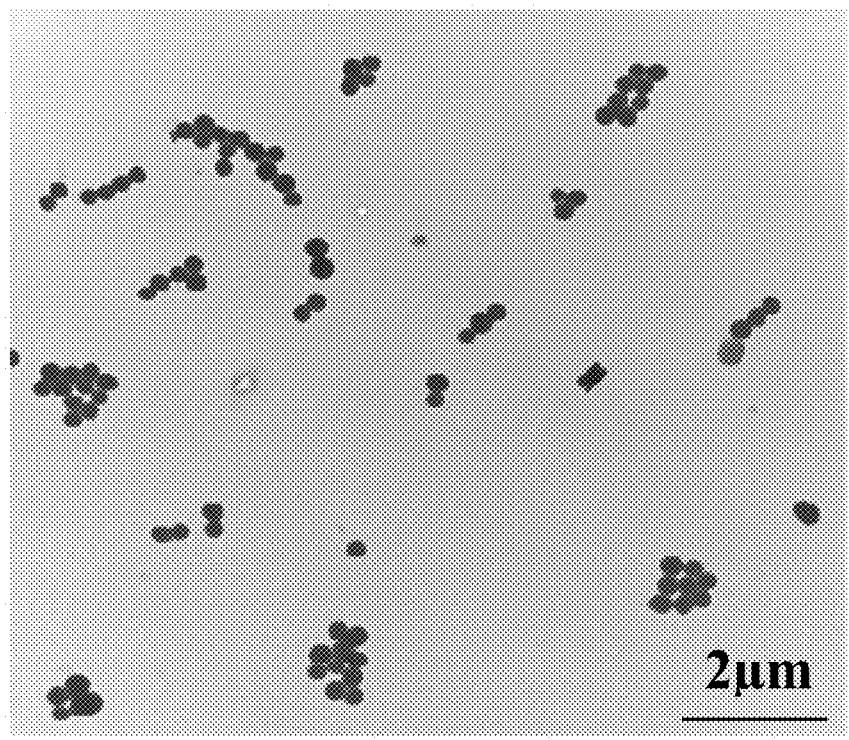
FIG. 32 shows TEM micrograph of self assembled solid spheres cross-linked with mTGase and 20% THF.
Figure 33:
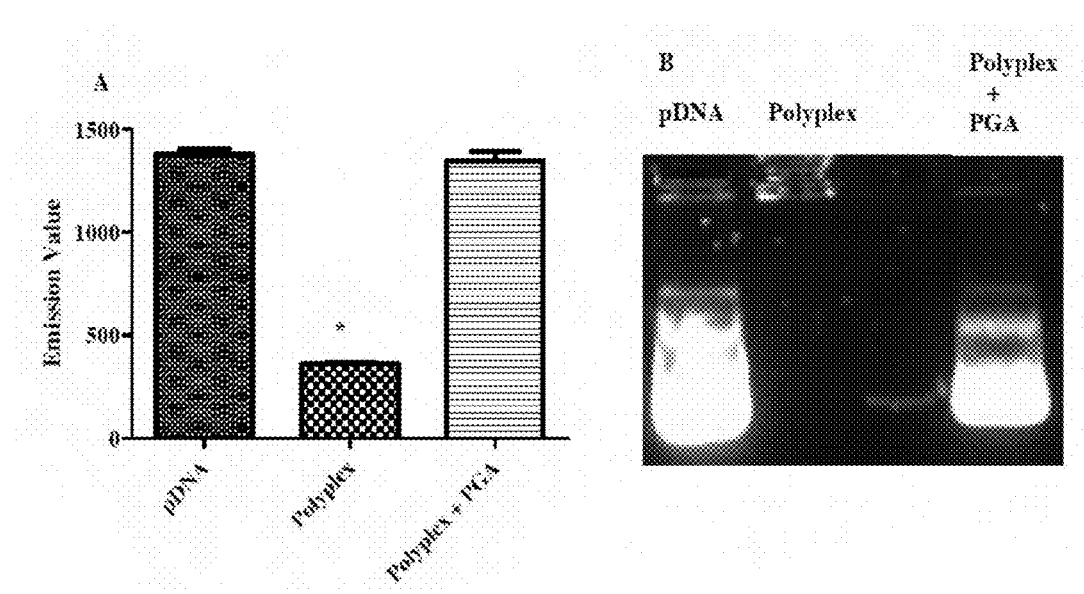
FIG. 33 shows PicoGreen® assay and agarose gel electrophoresis showing release of pDNA from the polyplex using polyglutamic acid. PicoGreen® assay and agarose gel electrophoresis showing release of pDNA from the polyplex using polyglutamic acid. (A) PicoGreen® assay showing emission values and (B) agarose gel of pDNA, polyplex and polyplex treated with PGA. Statistical significance was determined by one way ANOVA (n=3, p<0.05)

In vitro studies demonstrated the spheres significant capacity to encapsulate pDNA with efficiency of up to 95% (FIG. 16A). The potential of these shells for gene transfection was investigated by studying cellular uptake. It was observed that for the uptake by cells, the spheres need a longer incubation time (6-12 hours) than cationic polyplexes (FIG. 16B). This is because of their negative/neutral surface charge ratios, which allow them to stay in presence of serum without aggregation or precipitation. Following encapsulation, the integrity of the pDNA was checked using gel electrophoresis (FIG. 17). After washing, no free pDNA was left in solution and no degradation band appeared on the gel. The degree of protection afforded by the complexes and their ability to release the pDNA were also examined. In order to mimic the in vivo conditions (presence of proteins), the release was performed in FBS-containing medium. No release of pDNA was observed, even after three days of incubation (FIG. 18). The integrity of the complexes was checked by SEM, and TEM and no degradation or modification of the shape was observed. On the other hand, in presence of enzyme, Picogreen® assay showed a release of 30% of the encapsulated pDNA after 72 hours without any damage FIG. 19. To quantify the polyplex, it was treated with PGA of 10 mg/ml concentration. Results from agarose gel electrophoresis were consistent with that of PicoGreen® where a similar band pattern was observed between pDNA and PGA treated polyplex. (FIG. 31). To characterize loading, 1000 nm hollow spheres were incubated with an initial 20 µg of pDNA alone and polyplex containing the similar amount of pDNA. The loading efficacy of the NUI Galway hollow nanosphere technology was compared to that of solid spheres of similar size. Solid spheres of around 300 nm were fabricated by incubating 1 mg/ml of polymeric solution with 20 µg of pDNA at 37° C. The solid spheres were stable after cross-linking with mTGase and adding 20% of THF (FIG. 32). pDNA of the same amount was incubated with 300 nm hollow spheres for 12 hours. The loading efficiency was analyzed by quantification of pDNA in the supernatant using PicoGreen® assay (FIG. 30A). Irrespective of a negative surface charge, the hollow spheres showed around 25% higher pDNA loading than the solid spheres. In the case of polyplex, free pDNA was quantified for the loading efficiency. The pDNA was released from the polyplex by treating with 10 wt % of polyglutamic acid (PGA) (FIG. 33). The method was used to allow accurate quantification of pDNA loading. The result showed that almost 98% of pDNA was loaded within the hollow spheres in the form of polyplex as compared to 54% of pDNA alone (FIG. 30 B). The maximum loading was seen in the case of 1:80 which did not show any significant difference when increased to 1:160. Thus the result showed an approximate 69 µg of pDNA/mg of hollow sphere as the maximum loading efficiency. In addition, the loading was found to be similar in all the four sizes of hollow spheres tested (FIG. 30 D).

Figure 34:
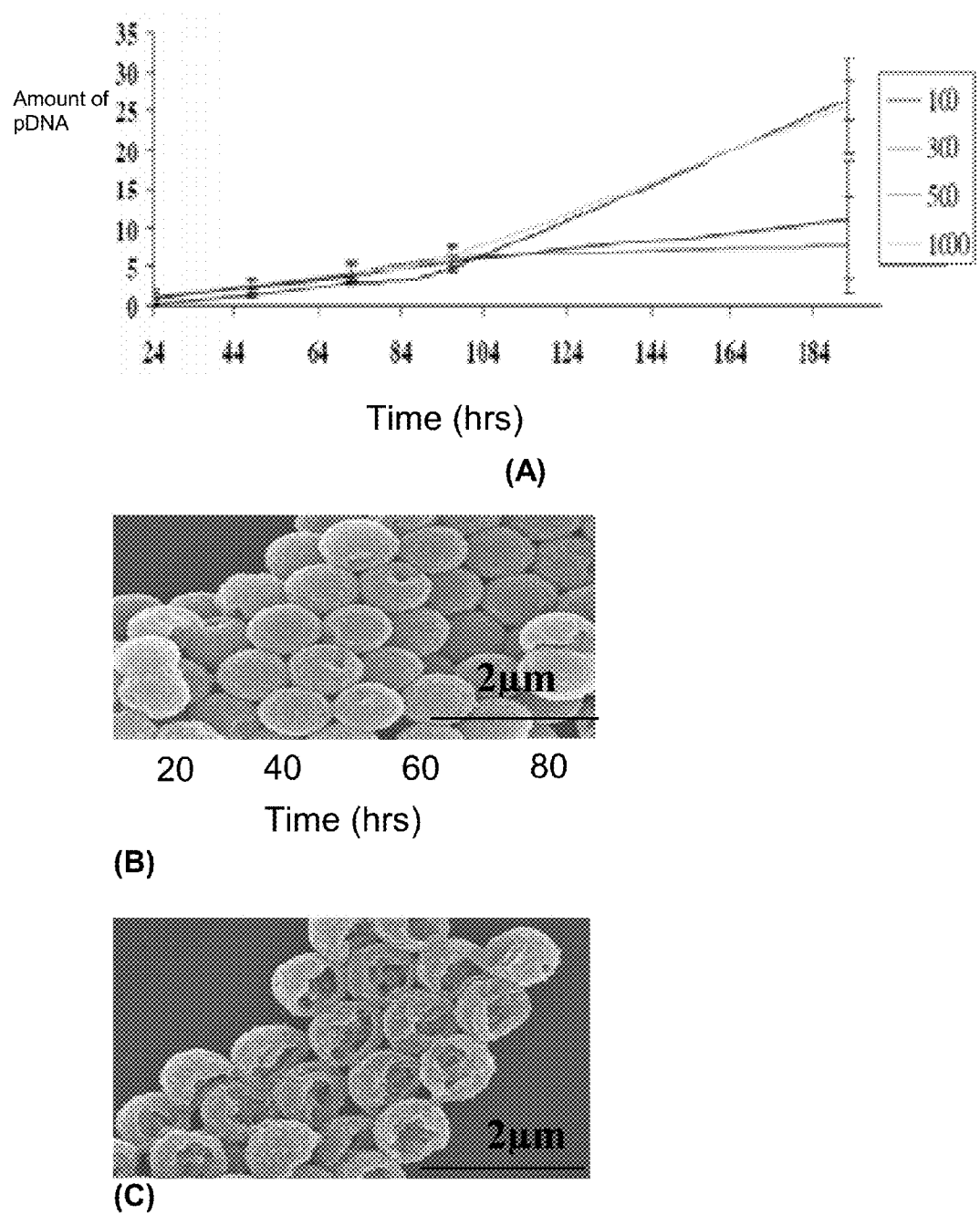
FIG. 34 shows release profile of hollow spheres. Release profile of hollow spheres (A) cumulative release profile of pDNA/polyplex from all four different sizes of hollow spheres at 37° C., (B) in vitro release study of hollow spheres in the presence of 10 U/g of protease (pH 7.5), (C1) SEM image of untreated 1000 nm hollow spheres, (C2) degrading hollow spheres in the presence of protease after 72 hours.

Release studies were performed in the presence of enzymes at 37° C. The release pattern was observed up to 192 hours for all sphere sizes. Spheres of 1 mg dry weight containing 60-70 µg of pDNA were used for this study. No significant difference in the release pattern was observed for differences in sphere sizes up to 96 hours. And a total of 6-7 µg of pDNA was released. However, the release profile was found to be different at 192 hours, where the 100 nm and 300 nm hollow spheres showed less release than 500 and 1000 nm hollow spheres (FIG. 34 A). The hollow spheres were then treated with appropriate enzymes which are abundantly found inside the human body in diseased conditions. The enzymatic treatment released polyplexes much faster than untreated spheres (FIGS. 134 B and E). The control hollow spheres without any treatment of enzymes had a release of 20% of pDNA at 72 hours, whereas the release for enzyme treated spheres were found to be 85, 71% and 70% respectively. Degradation of the hollow spheres was observed under SEM (FIG. 34 C2).

DNA Protection

Figure 20:
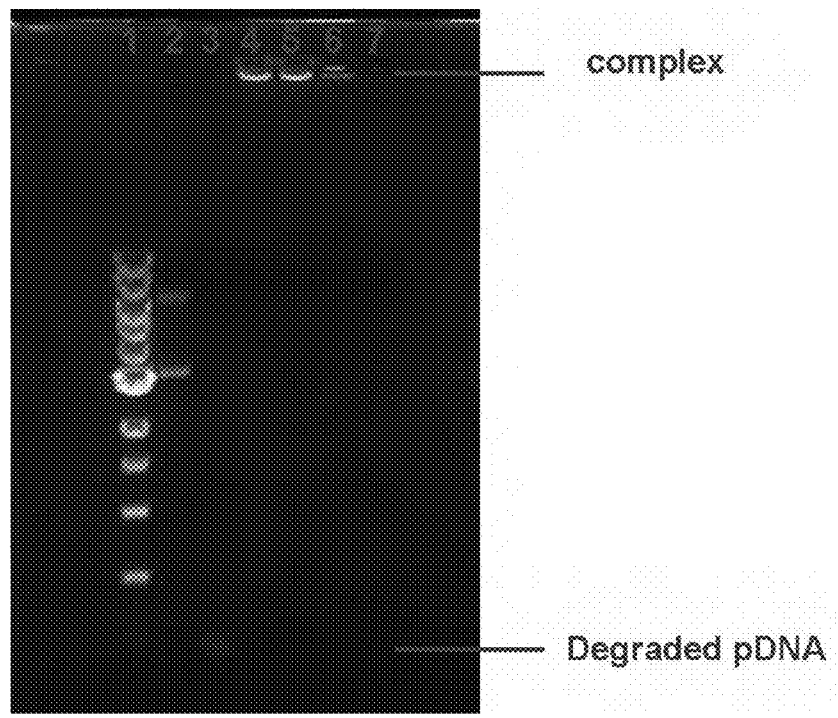
FIG. 20 shows electrophoresis gel (0.9% agarose) after DNase1 exposure with Ladder (1 kb) of native pDNA, and Shell/pDNA complex with and without exposure to DNase1. Electrophoresis gel (0.9% agarose) after DNase1 exposure with Ladder (1 kb) (1), native pDNA (2), pDNA exposed to DNase1 (3), Shell/pDNA complex (4), Shell/pDNA complex exposed to DNase1 (5), extracted Shell/pDNA complex (6) and extracted Shell/pDNA complex exposed to DNase1 (7)

The ability of the spheres to protect the pDNA was studied using DNase1 enzyme. After 15 minutes of incubation with DNase1, no apparent degradation of pDNA was seen using gel electrophoresis (FIG. 20). Moreover, no free or degraded DNA was observed after complex extraction (FIG. 20), implying that no pDNA was extracted or released from the shell.

Cell Uptake

Figure 21:
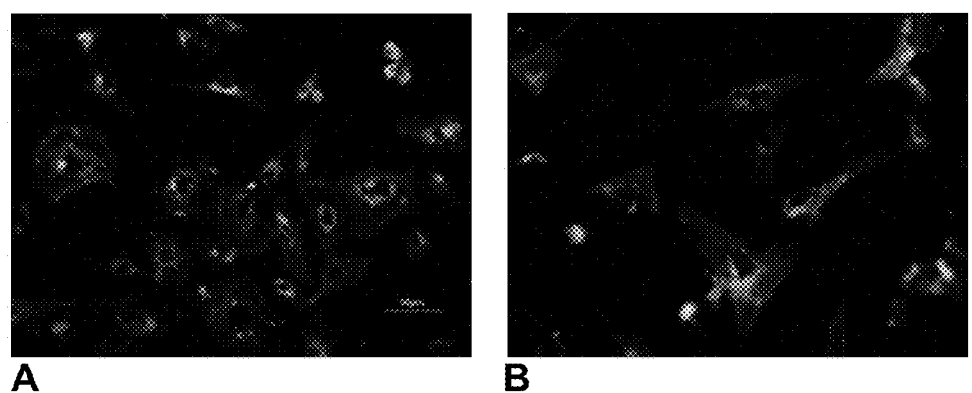
FIG. 21 shows fluorescent microscope micrographs of HUVEC cell stained with rhodamine phalloidin incubated up to 48 hours. Fluorescent microscope micrographs of HUVEC cell stained with rhodamine phalloidin (red) incubated 6 H(A) and 48 H (B) with FITC labelled spheres (green), scale bare (50 μm)
Figure 22:
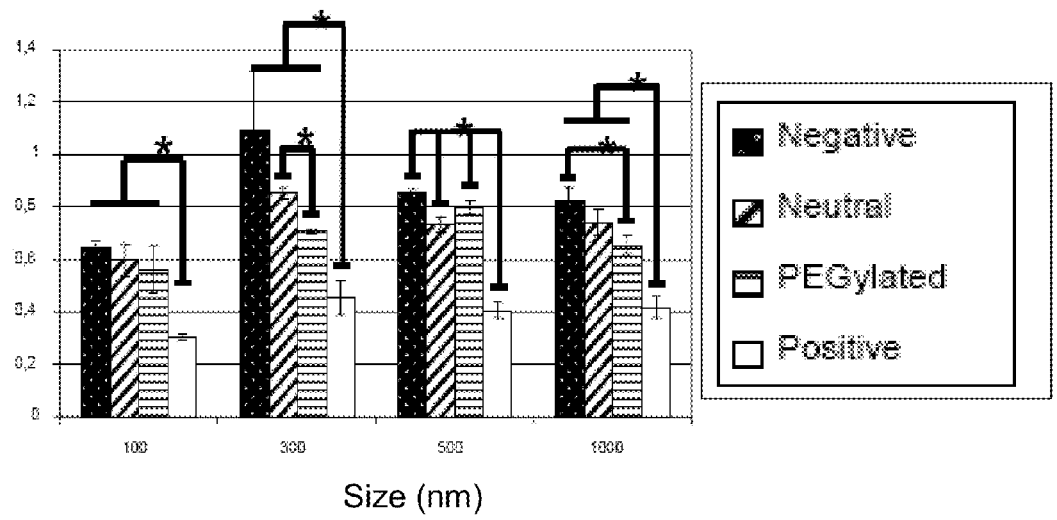
FIG. 22 shows the charge effect of the nanospheres (nanoshells) on haemolysis.
Figure 23:
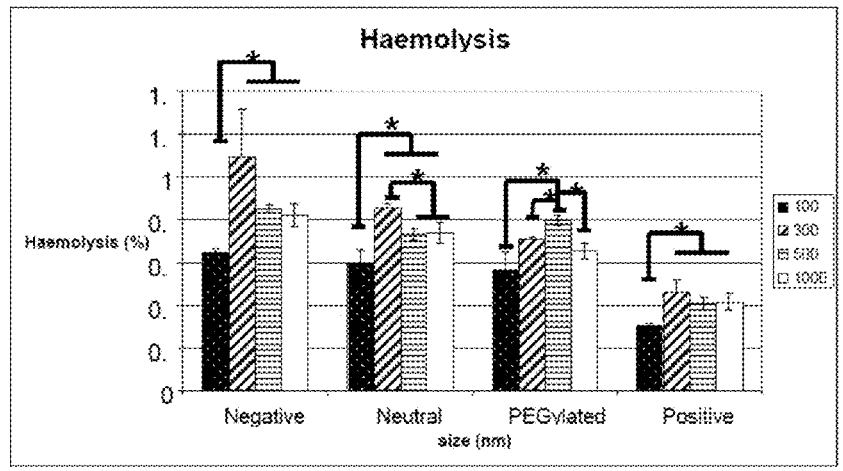
FIG. 23 shows the effect of size of the nanospheres (nanoshells) on haemolysis.
Figure 24:
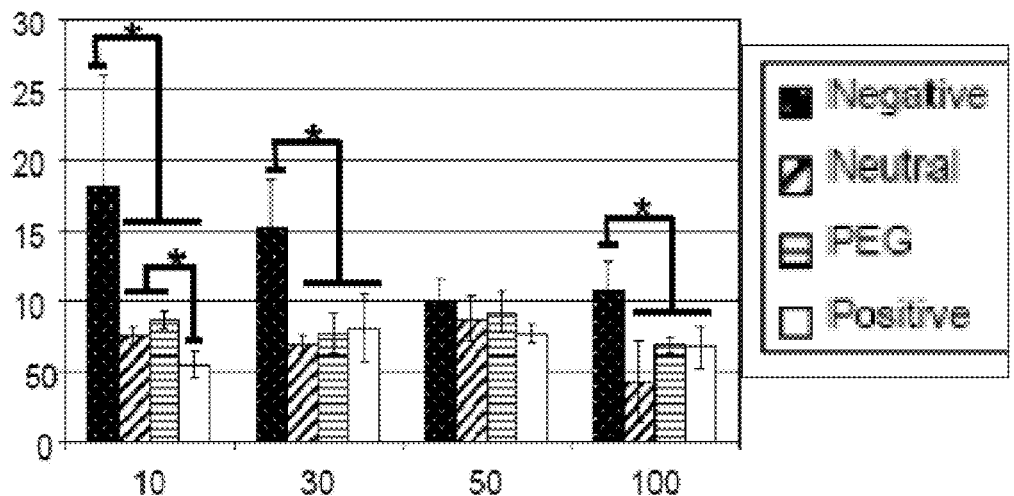
FIG. 24 shows the charge effect of the nanospheres (nanoshells) on platelet activation determined by the amount of sP-selectin in solution.
Figure 25:
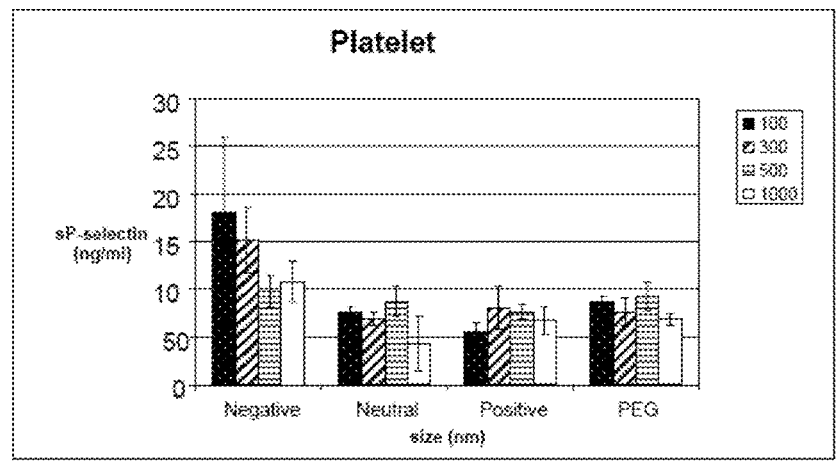
FIG. 25 shows the size effect of the nanospheres (nanoshells) on platelet activation determined by the amount of Sp-selection in solution.

The kinetic uptake of FITC labelled spheres (100 to 600 nm) by Human Umbilical Vein Endothelial Cells (HUVEC) and Human Vascular Smooth Muscle Cells (HVSMC) was studied. Confocal micrographs shows that both cell lines which were stained in red) are uptaking FITC labelled Spheres (which were stained in green) from 6 to 12 hours (FIG. 21). Moreover when the incubation time is increased, results show an increase in uptake. These results have been confirmed by flow cytometry which shows a significant increase in the fluorescence.

Blood Compatibility

A major challenge for the systemic delivery of synthetic vehicles for gene delivery is their lack of stability in the blood stream, their degradation, and clearance by the reticuloendothelial system, which makes the elucidation of their interaction with blood components essential. Several interactions with the family of spheres were investigated to determine the potential systemic delivery in vivo of the hollow spheres. The nanoshells according to the invention were tested for biocompatibility. The results are shown in FIGS. 22 to 25. The effect of various parameters such as the charge on the spheres and size of the spheres, on haemolysis and platelet activation was studied.

All the experiments for haemocompatibility were performed using human venous blood from healthy volunteer donors. Haemolysis was evaluated on venous blood anticoagulated with EDTA. Within 2 h, the erythrocytes were washed and resuspended in PBS at a ratio of 1:10. Functionalised spheres were added in triplicate to the erythrocyte suspension to a final concentration of 50 µg/ml. TritonX was tested as the positive control. After incubation at 37° C. for 2 h, the samples were centrifuged at 1000 rpm for 15 min to remove the non-lysed erythrocytes. The supernatants were collected and analyzed for the released haemoglobin by spectrophotometric determination at 540 nm. To obtain 0 and 100% haemolysis, the erythrocyte suspension was added to PBS and to TritonX, respectively. The degree of haemolysis was determined by the following equation:

$$\text{haemolysis }(\%)=(Abs-Abs_0)/(Abs_{100}-Abs_0)\times 100,$$

where Abs, $Abs_0$ and $Abs_{100}$ are the absorbance of the test samples, a solution of 0% haemolysis and a solution of 100% haemolysis, respectively.

Supernatants obtained by centrifugation at 85 G (10 min) followed by one at 140 G (10 min) were reunited to compose the Platelet Rich Plasma (PRP). The number of platelets was determined under microscope with a haemocytometer after 1/100 PRP dilution with ammonium oxalate. Functionalised spheres were added to PRP to a final concentration of 100 µg/ml. PBS was tested as the negative control. The samples were rotated for 1 H at 37° C., then immediately centrifuged and the supernatant was analysed by Elisa test (#KHS2021, invitrogen) according to the manufacturer protocol.

The spheres according to the present invention are very suitable for in vivo use due to their haemocompatibility. In fact, haemolysis graphs (FIGS. 22 and 23) demonstrate that chitosan/PGA spheres don't lyse haemoglobin (<1%). Moreover, this rate decreases for the smallest sizes and when the surface of the sphere is functionalised. Furthermore, the elisa detection experiment shows that the platelet activation decreases after functionalisation.

Platelet Activation

Platelet activation was measured by the concentration of sP-selectin levels in the plasma and was determined using ELISA kit according to the manufacturer's protocol. Platelet-poor plasma (PPP) and Platelet-rich Plasma (PRP) were used as control.

Complement System

To assess complement activation, the cleavage of complement component C3 was monitored by measuring the formation of its activation peptide; C3a desArg, using a commercial C3a enzyme immunoassay kit.

Plasma Clotting Time 0.1 ml of the PPP and 40 µg of samples suspended in PBS were incubated at 37° C. for 5 min in a 96 well plate. 0.1 ml of 0.025 m $CaCl_2$ solution was then added and the plasma solution was monitored for clotting by manually dipping a stainless-steel wire hook coated with silicone into the solution, to detect fibrin threads. Clotting times were recorded as the time at which first fibrin strand formed on the hook. Plasma recalcification profiles are used to mimic the intrinsic coagulation system in vitro. PBS was used as a negative control in this study.

Cell Viability Study

Figure 35:
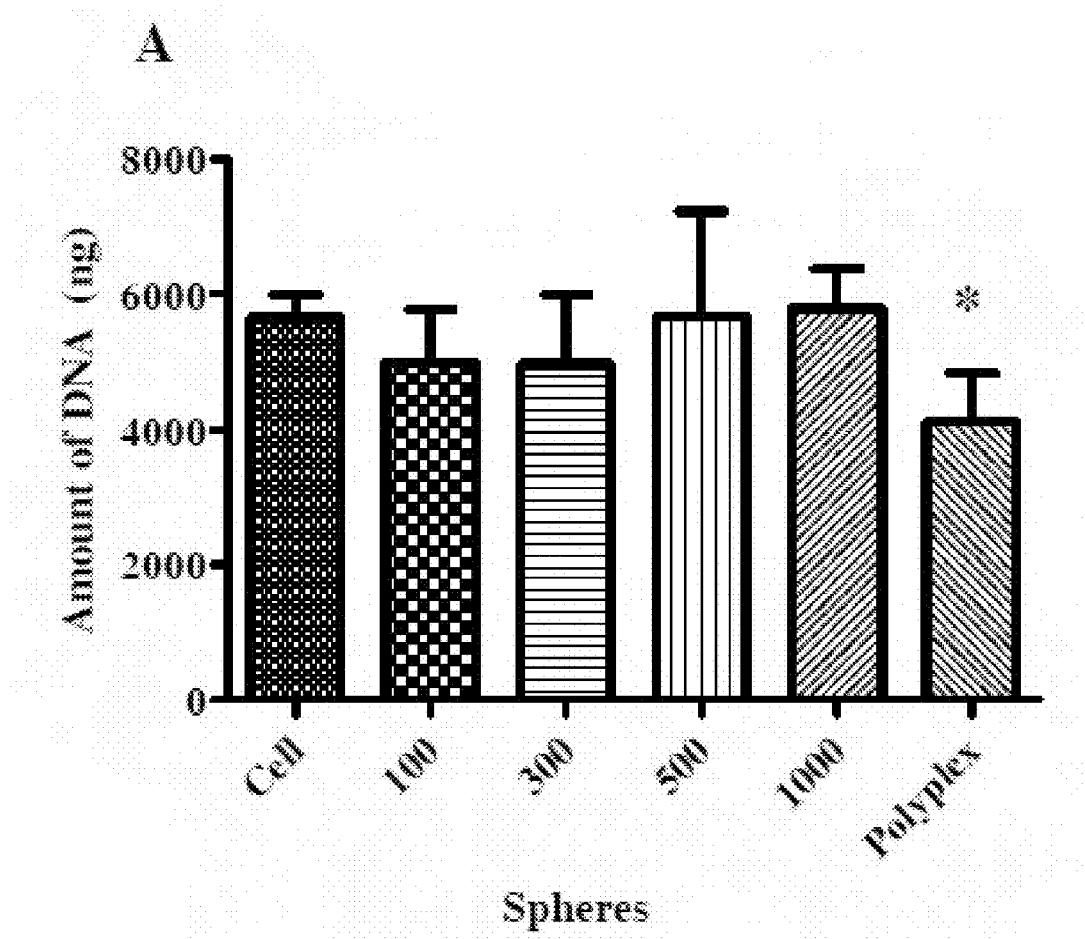
FIG. 35 shows cell viability and transfection efficiency of GLP loaded hollow spheres. Cell viability and transfection efficiency of GLP loaded hollow spheres. PicoGreen® assays showing the cell viability of loaded hollow spheres of all four different sizes in (A) ADSCs and (B) HUVECS after 48 hours. Gaussia luciferase assay for investigation of transfection efficiency of all four different sizes polyplex loaded hollow spheres (C). All the data are represented as the mean±standard deviation (n=3). Statistical difference was determined using one-way ANOVA. * indicates a statistically significant difference between samples with p<0.05.
Figure 35:
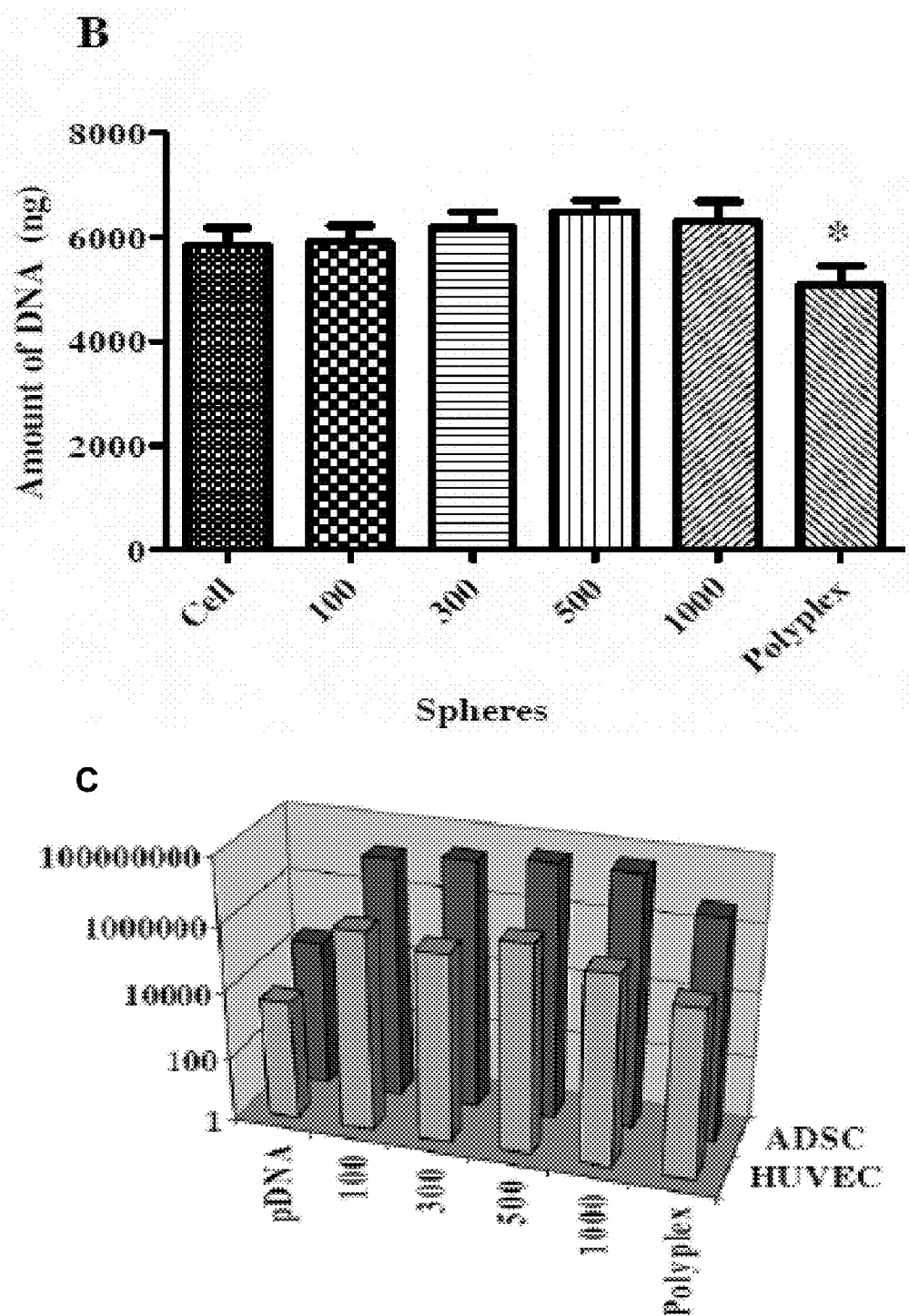
Figure 36:
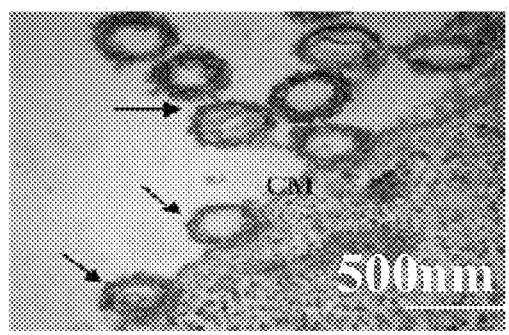
FIG. 36 shows TEM images showing the internalization pathway of 500 nm hollow sphere loaded with polyplexes within ADSCs. TEM images showing the internalization pathway of 500 nm hollow spheres loaded with polyplexes within ADSCs. Hollow spheres were observed at different locations in the cell (A) attached to cell membrane, (B) cell membrane engulfing a sphere, (C) in early endosomes close to the cell membrane, (D) in late endosome or lysosome near to nucleus, (E) rupturing the lysosomal membrane and also spheres are degrading and (F) coming out of the lysosome by completely disrupting the lysosomal membrane. Cell membrane, endosomes and lysosome have been represented as CM, E and L respectively in the figures.
Figure 36:
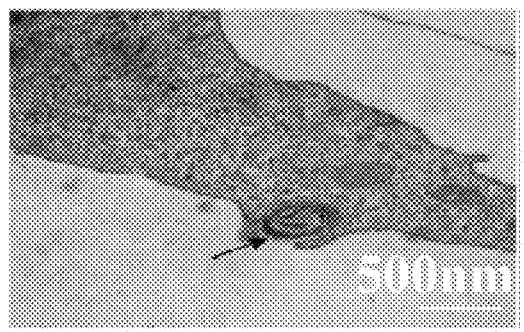
Figure 36:
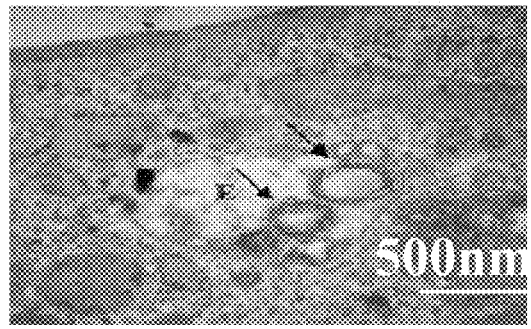
Figure 36:
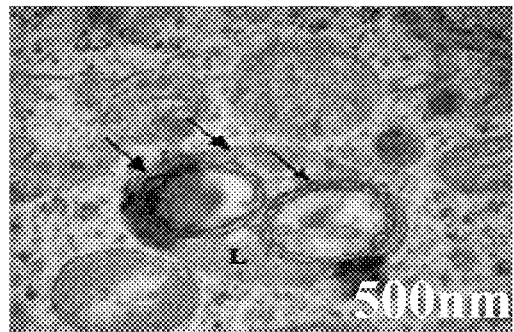
Figure 36:
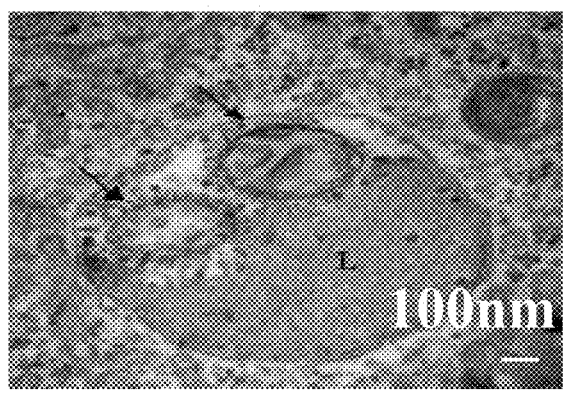
Figure 36:
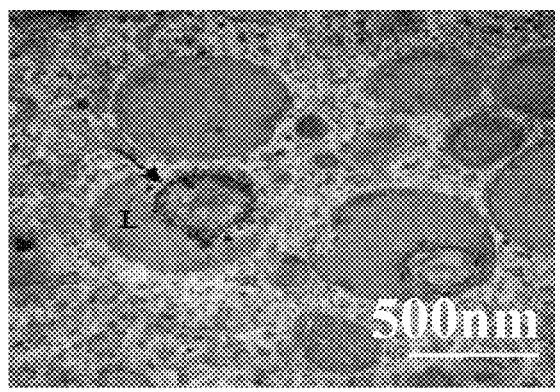

Spheres of all four different sizes were loaded with *gaussia* luciferase plasmid (GLP). The GLP/polyplex loaded spheres of all the sizes showed a similar cell viability to the control (untreated cell) in both ADSCs and human umbilical vein endothelial cells (HUVECs) after 48 hours, whereas the cells treated with polyplex alone showed less cell viability as evident from the PicoGreen® assay (FIGS. 35 A and B). Polyplex loaded hollow spheres of all the sizes showed better expression than pDNA and polyplex alone in both ADSCs and HUVECs (FIG. 35 B). In addition, similar luciferase expression was found for all the sizes without any significant difference in either ADSCs or HUVECs. FIG. 35 C showed an almost 10 times higher transfection level of polyplex loaded spheres than the pDNA demonstrating the endosomal protection ability of polyplex loaded hollow spheres in ADSCs. The cellular internalization pathway of the polyplex loaded sphere was tracked inside ADSCs to assess the mechanism of endosomal protection. ADSCs treated with 500 nm spheres were fixed and embedded in resin after 6, 12 and 24 hour time points. The negatively charged spheres point was observed attaching on the cell membrane (CM) after 6 hour time (FIG. 36 A) and were gradually engulfed by the CM (FIG. 36 B). FIG. 36 C shows the hollow spheres in an early endosome after 12 hours. The spheres were then observed in late endosome or lysosome adjacent to the nucleus (FIG. 36 D). After 24 hours, the lysosome starts to degrade as a consequence of its internalized sphere, and the sphere also loses its shape and starts to degrade (FIG. 36 E). The hollow sphere eventually exits the degrading lysosome (FIG. 36 F). The hollow spheres can be used as a gene delivery depot system for spatial and temporal controlled pDNA release leading to a sustained, local delivery of therapeutic factors and also as a transfection agent. The polyplex used can protect pDNA from degradation, promote interaction with cell membranes, and facilitate endosomal release via the proton sponge effect. Moreover, significantly higher amounts of gene can be loaded in hollow spheres. In addition, hollow spheres can be used for the loading of both hydrophobic and hydrophilic drug molecules as the loading will be through a diffusion related process. The free —$NH_2$ and —COOH groups can be readily conjugated to targeting moieties for specific applications.

Figure 37:
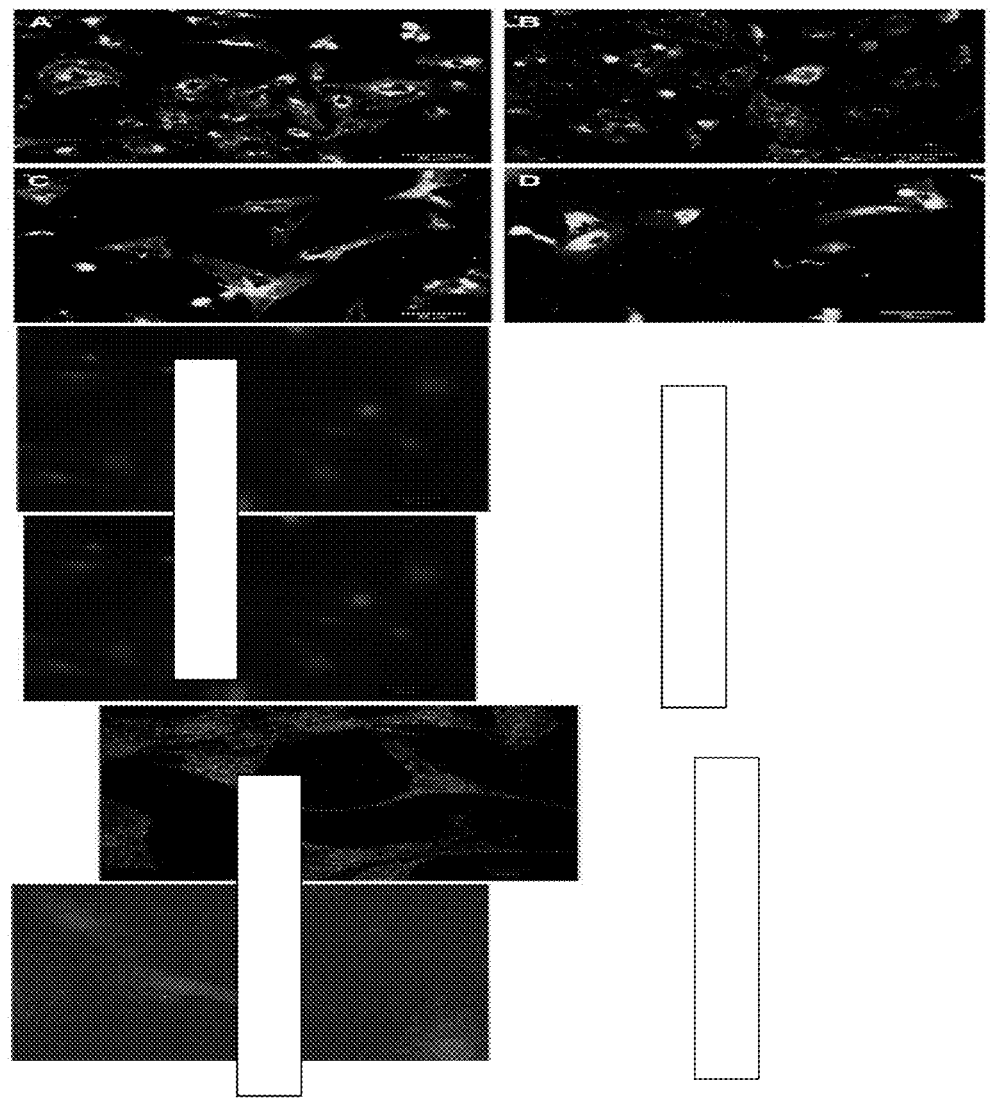
FIG. 37 shows confocal micrographs of FITC labelled hollow spheres. Confocal micrographs of FITC labelled hollow spheres (A) 100 nm and (B) 300 nm internalized into HUVECs and (C) 100 nm and (D) 300 nm internalized into HUASMCs. All images were taken after 24 hours incubation with cells. Confocal microscopy of adipose derived stem cells after (D) 30 min (E) 2 h (F) 4 h (G) 24 h, incubation with nanospheres.
Figure 38:
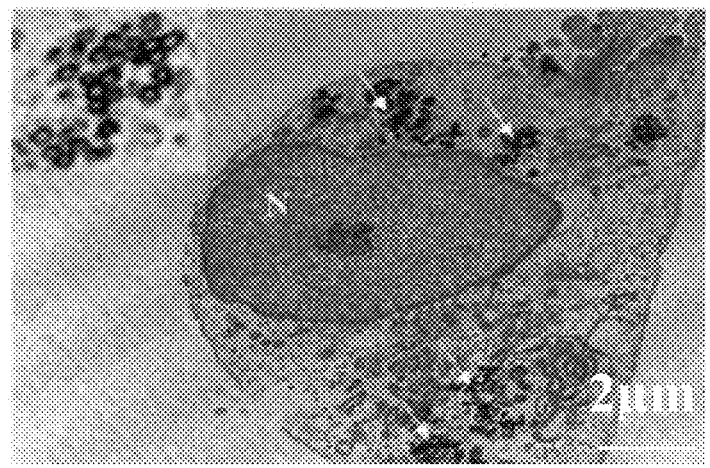
FIG. 38 shows TEM images illustrating 100 nm neutrally charged hollow spheres internalized into HUVECs and HUASMCs cells. TEM images illustrating 100 nm neutrally charged spheres internalized into (A) HUVECs inset shows the hollow spheres inside lysosome), (B) HUASMCs (inset shows hollow spheres inside lysosome) (C) Higher Magnification image of (A) showing endocytic internalization of hollow spheres from endosome (E) to lysosomes (L) near nucleus (N)
Figure 38:
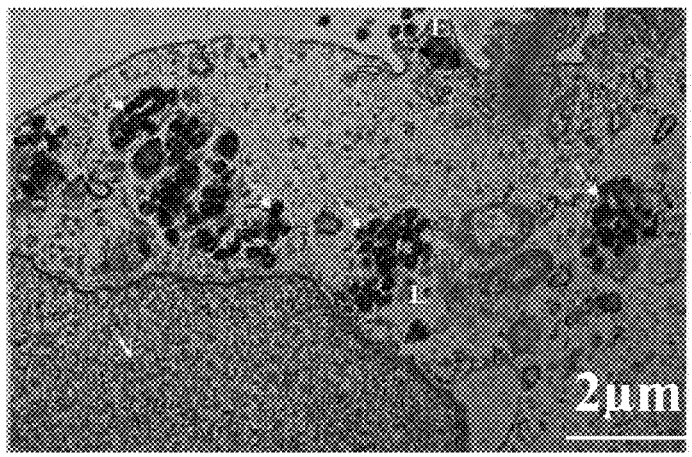
Figure 38:
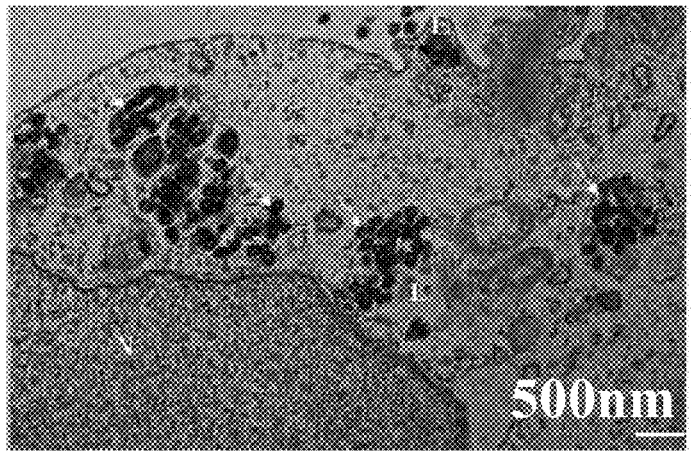

Cellular Internalization Behaviour of Spheres
Characterization by Confocal Imaging HUVECs and HUASMCs cells were incubated with FITC labelled hollow spheres. Confocal micrographs show co-localization of the negatively charged FITC labeled spheres (green) within HUVECs and HUASMCs after 24 hour incubation (FIG. 37). 100 nm and 300 nm spheres can be seen in the perinuclear region of the cells. The cell uptake of hollow spheres was investigated by TEM. During time depended cellular tracking of the fluorescent nanospheres, fluorescence appeared to be distributed throughout the cytoplasm inside the cells post 4 hours incubation with nanospheres in the presence of serum containing media (FIG. 37(D-G)). Cells incubated with 100 nm neutral hollow spheres for 24 hours were observed under TEM (FIG. 38). TEM micrographs show hollow spheres within lysosomes of both the cell types (FIGS. 38 A and B). FIG. 38 C illustrates the endocytic pathway of hollow spheres from early endosome to lysosome inside HUVEC.

Quantification by Flow Cytometry

Figure 39:
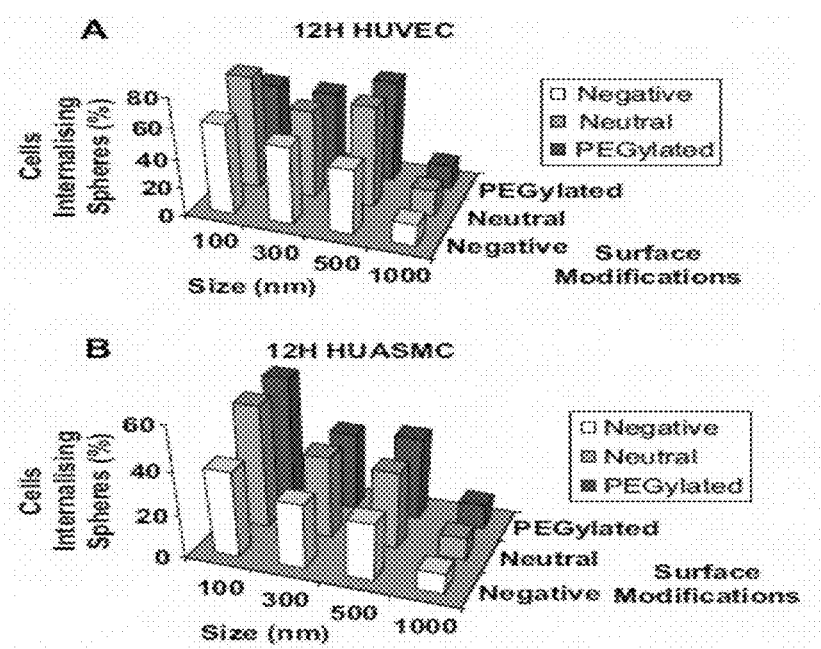
FIG. 39 shows flow cytometry data, elucidating the effect of size and surface modifications on the internalization efficiency of hollow spheres into HUVECs and HUASMCs cells. Flow cytometry data, elucidating the effect of size and surface modifications on the internalization efficiency of spheres into (A) HUVECs and (B) HUASMCs at 12 hours incubation.

Cells were then analyzed using flow cytometry for internalization efficiency. The impact of size and surface charge on cellular internalization was quantified at 12 hours following incubation using flow cytometry. FIG. 39 shows internalization efficiency of spheres within HUVECs (FIG. 39 A) and HUASMCs (FIG. 39 B). 100 nm neutral spheres showed increased internalization in both cell types with 76% in HUVECs and 56% in HUASMCs. HUASMCs had reduced sphere uptake than HUVECs in all the sizes and surface modifications investigated. 300 and 500 nm spheres show similar internalization efficiency in both HUVECs and HUASMCs. 1000 nm spheres, regardless of surface charge had low internalization with 9-13% internalization in both cell types investigated. Among all the sizes, negatively charged spheres presented the lowest uptake profile.

Quantification by High Content Analysis

Figure 40:
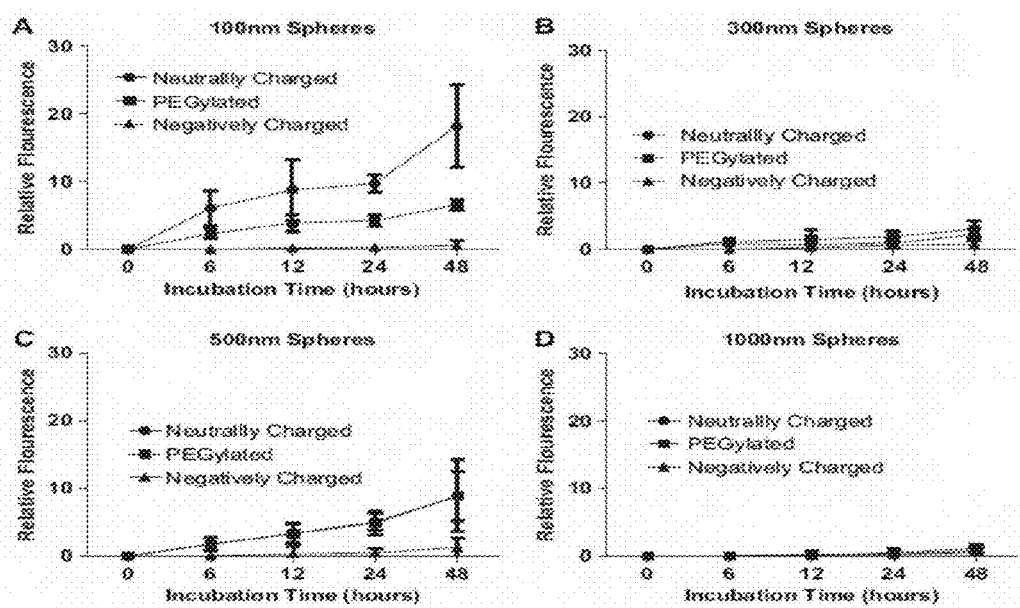
FIG. 40 shows high content analysis showing internalization of PEGylated, neutral and negatively charged hollow spheres with HUVECs over time. High content analysis showing internalization of PEGylated, neutral and negatively charged spheres with HUVECs over a time course period of 6, 12, 24 and 48 hours. Data is represented as the mean +/− standard deviation (n=3, p<0.05)
Figure 41:
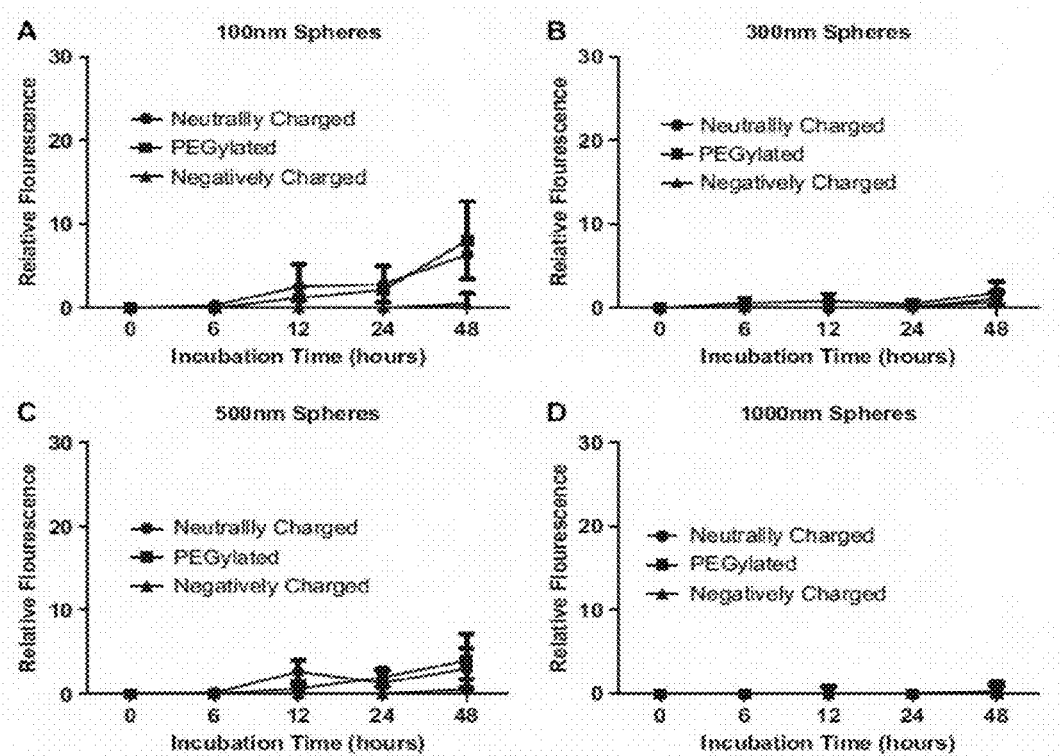
FIG. 41 shows high content analysis showing internalization of PEGylated, neutral and negatively charged hollow spheres with HUASMCs over time. High content analysis showing internalization of PEGylated, neutral and negatively charged spheres with HUASMCs over a time course period of 6, 12, 24 and 48 hours. Data is represented as the mean +/− standard deviation (n=3, p<0.05)

HUVECs and HUASMCs were seeded on 96-well plates for high content analysis (HCA). FITC-hollow spheres were seeded and incubated for different time points 6, 12, 24 and 48 hours. After the desired incubation times cells were fixed and stained for nucleus using TO-PRO-3 iodide. Finally, the sample wells were quantified using In Cell Analyzer 1000 GE Healthcare for 420 nm (FITC) and 620 nm (TO-PRO-3 iodide). HCA enabled quantitative estimation of the internalization of FITC labelled nanospheres of different parameters, including size, surface charges and time points within HUVECs and HUASMCs. Cellular internalization was estimated in terms of relative fluorescence. The results found that 100 nm neutral spheres were significantly more internalized ($p<0.05$) when compared with other sizes, for PEGylated and neutrally charged spheres in both cell types, which is consistent with flow cytometric data, and showed a constant increase of internalization over time from a relative fluorescence value of 6e18 in HUVECs (FIG. 40). Internalization is reduced in HUASMCs for all sizes and surface charges (FIG. 41). PEGylated 100 nm nanospheres show the same level of internalization with HUVECs and HUASMCs with an approximate relative fluorescence value of 8. Negatively charged spheres for all sizes resulted in less internalization in both type of cells. Also, neutral, PEGylated and negatively charged spheres of 1000 nm size had much less uptake for all the time points. Overall, the interaction of 100 nm nanospheres with both cell types result in a higher degree of internalization compared to the 300, 500 and 1000 nm size nanospheres. Neutrally charged sphere seems to be more relevant than PEGylated and negatively charged spheres for internalization. HUASMCs seem more resistant to internalization of hollow spheres rather than HUVECs.

Blood Compatibility

A major challenge for the systemic delivery of synthetic vehicles for gene delivery is their lack of stability in the blood stream, their degradation, and clearance by the reticuloendothelial system, which makes the elucidation of their interaction with blood components essential. Several interactions with the family of spheres were investigated to determine the potential systemic delivery in vivo of the hollow spheres. The nanoshells according to the invention were tested for biocompatibility. The results are shown in FIGS. 22 to 25. The effect of various parameters such as the charge on the spheres and size of the spheres, on haemolysis and platelet activation was studied. All the experiments for haemocompatibility were performed using human venous blood from healthy volunteer donors.

The spheres according to the present invention are very suitable for in vivo use due to their haemocompatibility. In fact, haemolysis graphs (FIGS. 22 and 23) demonstrate that chitosan/PGA spheres don't lyse haemoglobin (<1%). Moreover, this rate decreases for the smallest sizes and when the surface of the sphere is functionalised. Furthermore, the elisa detection experiment shows that the platelet activation decreases after functionalisation.

Haemolysis

Figure 42:
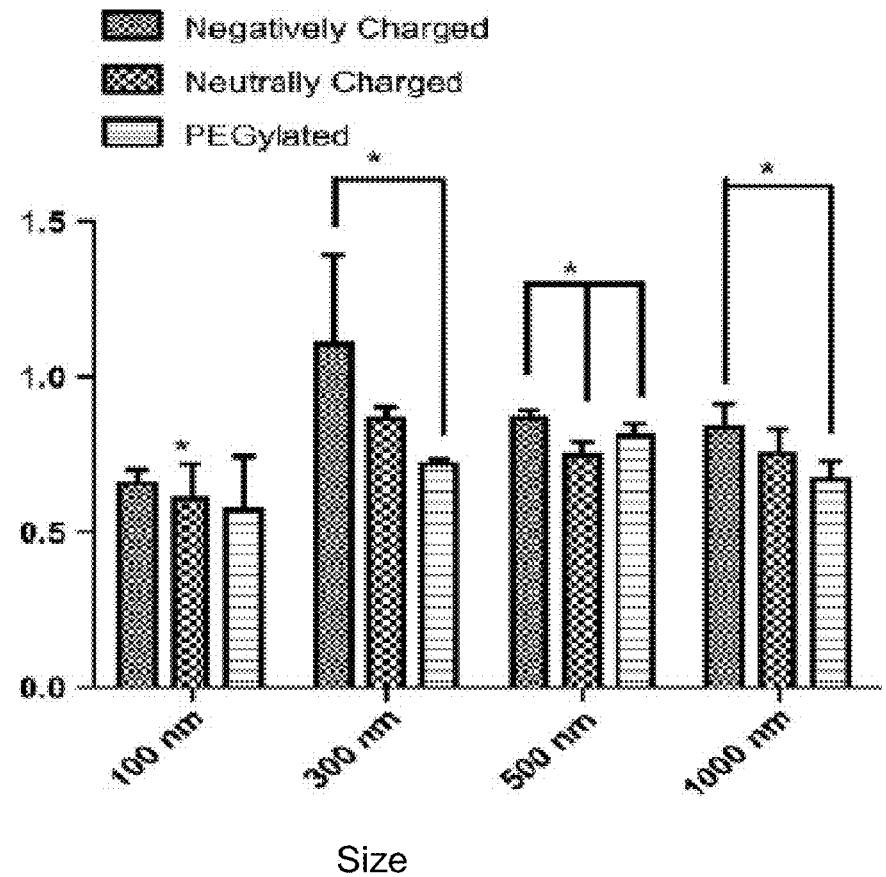
FIG. 42 shows the effect of hollow sphere size and surface charge on % haemolysis after incubation with human erythrocytes. % Haemolysis after incubation with human erythrocytes with (A) effect of size and (B) effect of surface charge. Data is represented as the mean +/− standard deviation (n=4). * indicates a statistically significant different between samples with p<0.05.
Figure 42:
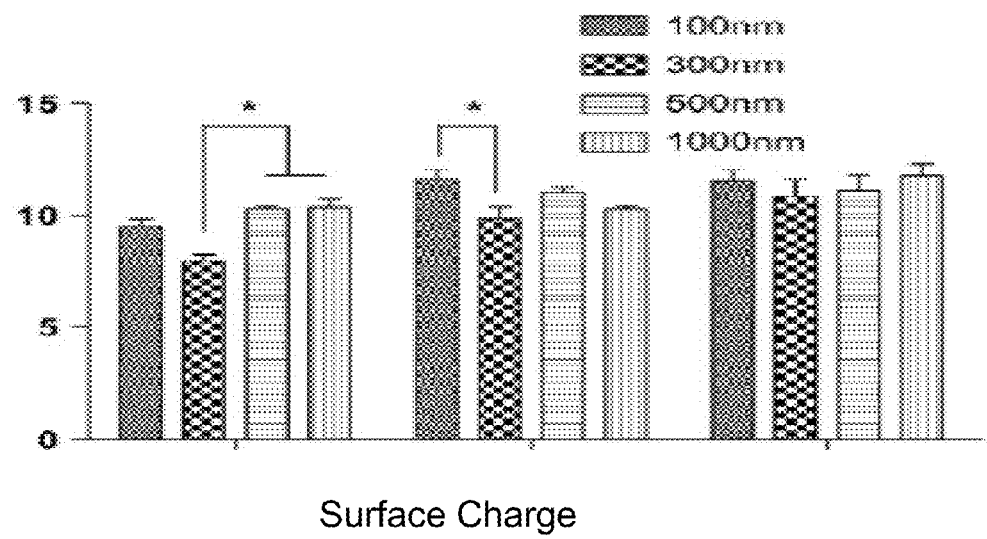

Negatively charged spheres have a significantly higher % haemolysis at sizes 300, 500 and 1000 nm whereas PEGylated spheres have a significantly reduced % haemolysis at these sizes. 100 nm spheres have a significantly reduced % haemolysis for all surface charges (FIG. 42). Irrespective of size or surface charge, all spheres have a negligible effect on haemolysis (1%).

Platelet Activation

Figure 43:
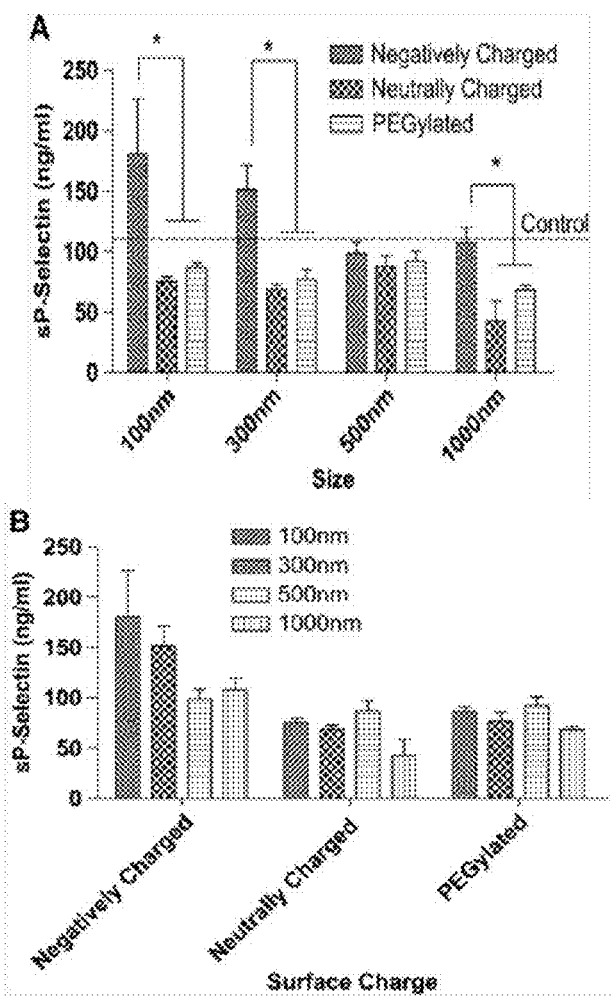
FIG. 43 shows the effect of hollow sphere size and surface charge on platelet activation as indicated by sP-Selectin release. Platelet activation as indicated by sP-Selectin release (A) effect of size and (B) effect of surface charge. Data is represented as the mean +/− standard deviation (n=4). * indicates a statistically significant difference between samples with p<0.05.

In this study, platelet activation was quantified by the release of soluble P-selectin (sP-Selectin) after incubation with all spheres. PBS was used as a negative control. The results found that size does not have a significant influence on the platelet activation. Negatively charged spheres however, induce a significantly higher level of sP-Selectin (p<0.05) when compared to other neutral and PEGylated spheres for all sizes (FIG. 43).

Complement System

Figure 44:
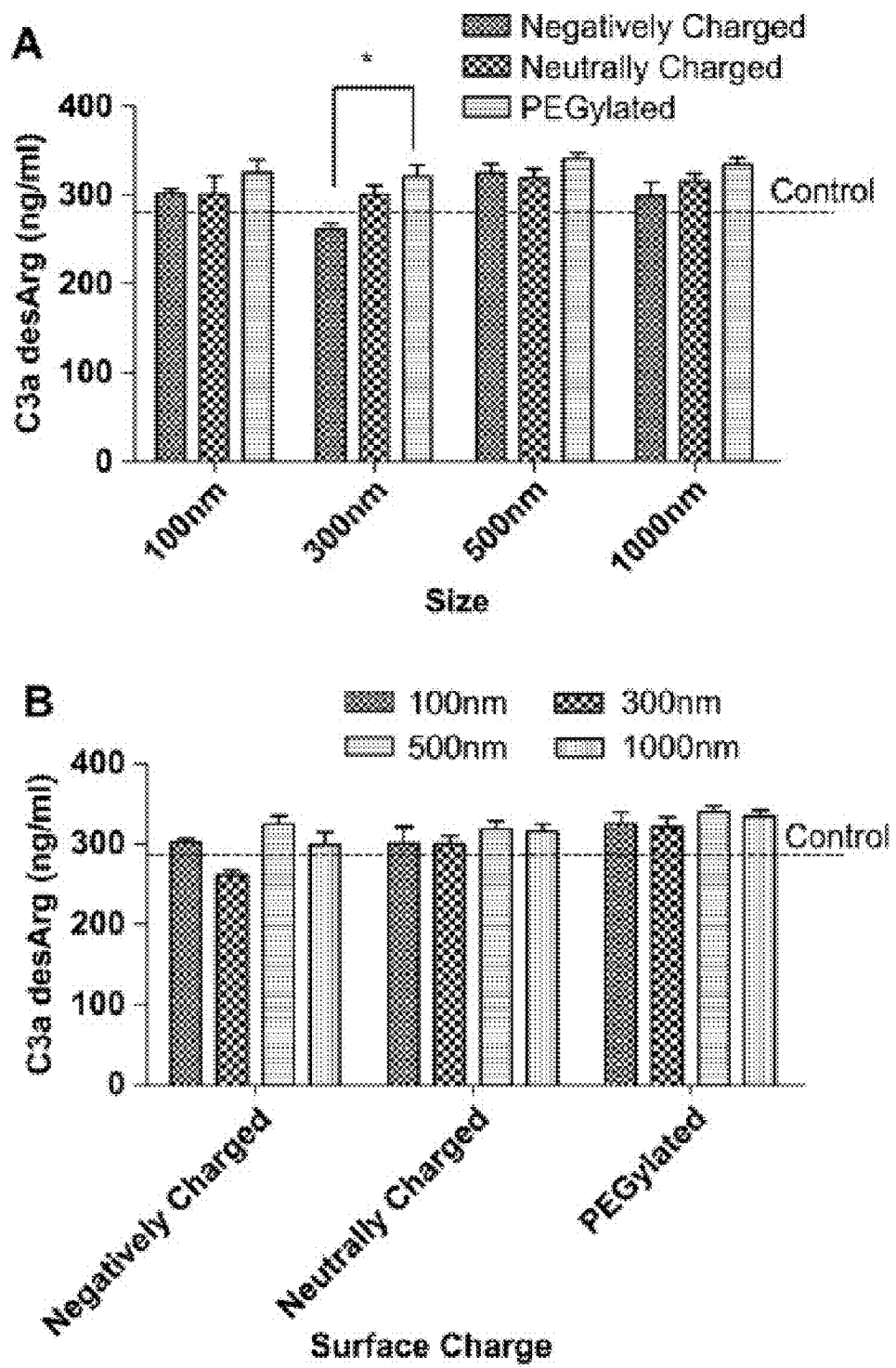
FIG. 44 shows the effect of hollow sphere size and charge on complement activation as indicated by C3a release. Complement activation as indicated by C3a release (A) effect of size and (B) effect of surface charge. Data is represented as the mean +/− standard deviation (n=4). * indicates a statistically significant difference between samples with p<0.05.

In this study complement activation was investigated by quantifying the release of C3a after incubation with spheres. PBS was used as a negative control and no significant difference was observed between samples and the control (FIG. 44).

Plasma Clotting Time

Figure 45:
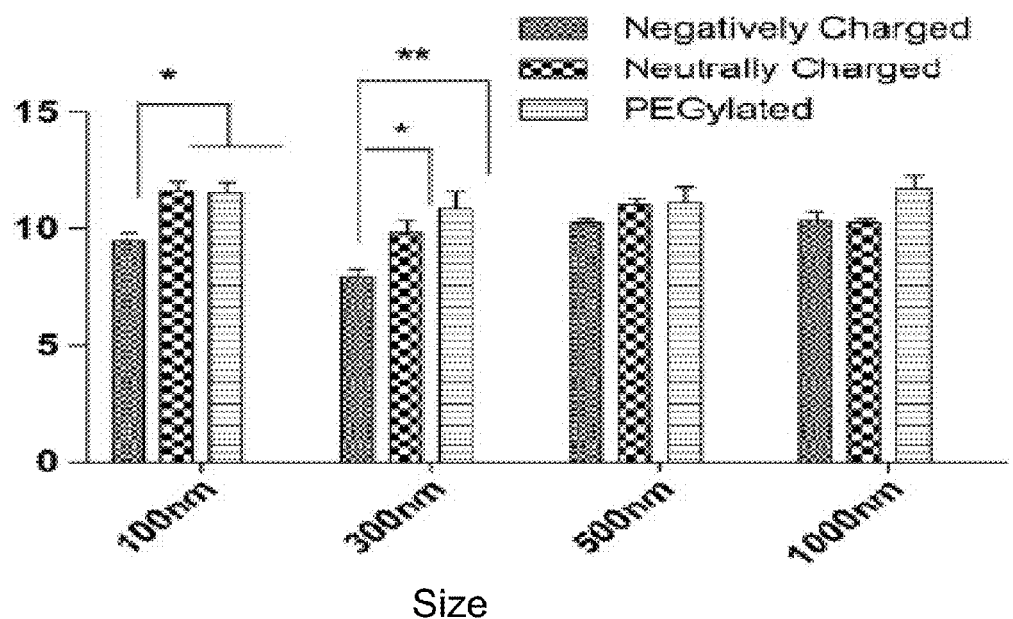
FIG. 45 shows the effect of hollow sphere size and charge on plasma recalcification time, quantified using calculation of the point at which the recalcification profile reaches half of the maximum absorbance value. Plasma recalcification time, quantified using calculation of the point at which the recalcification profile reaches half of the maximum absorbance value with (A) showing effect of size (B) showing effect of surface charge. Data is represented as the mean +/− standard deviation (n=4). * indicates a statistically significant difference (p<0.05), ** indicates a statistically significant difference (p<0.01).
Figure 45:
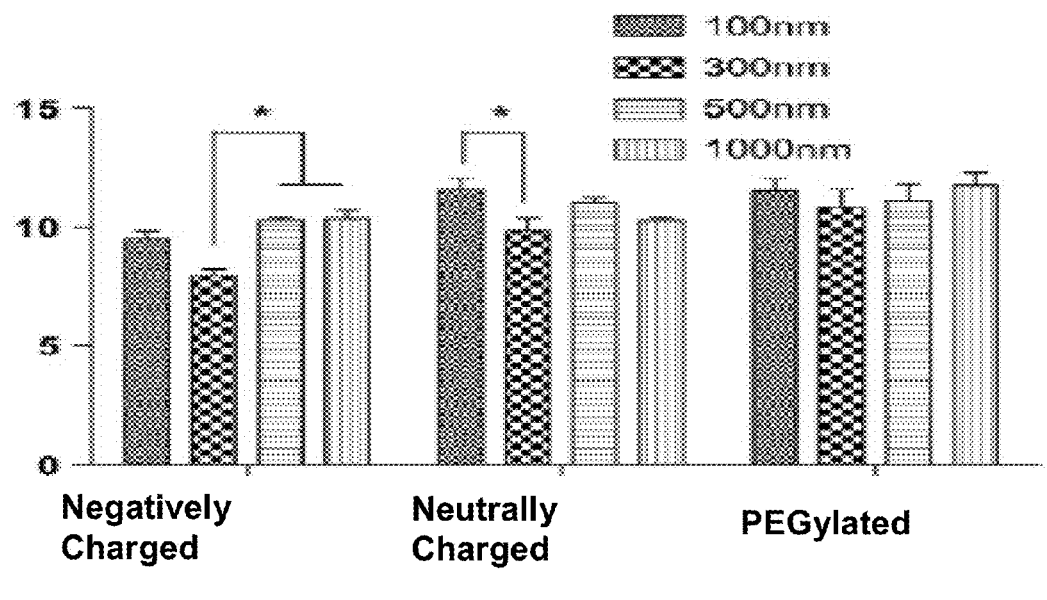

Plasma recalcification profiles are used to mimic the intrinsic coagulation system in vitro. PBS was used as a negative control in this study. To quantify plasma recalcification profiles, T1/2 max was calculated as the time at which half the saturate absorbance was reached. Clotting times are significantly shorter (p<0.05) for all samples when compared to the control (12.3+/−0.3 min). Negatively charged spheres had a significantly decreased clotting time when compared to other surface charges at 100 and 300 nm spheres. The absence of a significant effect at larger sphere size indicates that there is a size at which surface charge does not have an effect. The effect of size did not have a significant effect on the clotting time of PEGylated spheres whereas 300 nm spheres had a reduced clotting time when surface charge was negative and neutral when compared to 500 and 1000 nm spheres (FIG. 45).

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A process for the preparation of a natural or synthetic biodegradable polymeric hollow nanosphere comprising the steps of:
   (i) providing a template comprising polymeric polystyrene beads, mesoporous silica or diatomaceous silica;
   (ii) treating said template with a functionalising group to produce a functionalised template,
   (iii) treating said functionalised template with a solution of one or more natural or synthetic biodegradable polymers selected from the group consisting of: collagen, elastin, chitosan, hyaluronan, alginate, polyesters, PEG-based polymers, dendritic or hyperbranched polymers, and combinations thereof, and agitating to form a polymeric coating on said template;
   (iv) cross-linking said coating on the template with a cross-linking agent selected from the group comprising a dendrimer, a hyper-branched dendritic polymer and linear polymeric system, and combinations thereof, wherein the reactive groups in the cross-linking agent are —COOH or $NH_2$, groups and the reactive groups in the polymer are —COOH or $NH_2$, the molar ratio of reactive —COOH or —$NH_2$ groups in said dendrimer cross-linker to reactive groups —COOH or —$NH_2$ in said polymer is in the range 50:1 to 1:50; and
   (v) removing the template by treating said template with a solvent.

2. A process according to claim 1, wherein the molar ratio of reactive —COOH or —$NH_2$ groups in said dendrimer cross-linker to reactive groups —COOH or —$NH_2$, in said polymer is in the range 5:1 to 1:5.

3. A process according to claim 2, wherein the polymer and crosslinker are crosslinking using a promoter selected from the group comprising carbodiimide. transglutaminase, genepin, sulfonates, methyl sulfonate and trifluoromethyl sulfonate, malernide, and EDC/NHS coupling.

4. A process according to claim 1, wherein said functionalising group is selected from the group consisting of sulphate, a carboxyl or amine group.

5. A process according to claim 4, wherein said fiinctionalising group comprises sulphate.

6. A process according claim 1, wherein said template comprises sulfonated polystyrene beads.

7. A process according to claim 1, wherein said dendrimer or said hyper-branched dendritic polymer is selected from the group consisting of: peptide based dendrimers, polyamidoamine (PAMAM), poly (2-dimethyl-aminoethylmethacrylate) (PDMAEMA), poly ethylene glycol methyl ether methacrylate (PEGMEMA), ethylene dimethacrylate (EDGMA), polypropyleneimine, polyarylether, polyethyleneimine (PEI), poly-l-lysine (PLL), poly (ethylene glycol) methacrylate (PEGMA), poly (propylene glycol) methacrylate (PPGMA) polyacrylic acid and a polycarboxylic acid-polyethylene glycol-polycarboxylic acid (PPEGP) based dendrimer such as aconitic acid-polyethylene glycol-aconitic acid based dendrimer (APEGA) and combinations thereof.

8. A process according to claim 1, wherein the template is removed by treating the functionalised beads with acid solution in tetrahydrofuran (THF) prior to centrifugation to produce a nanosphere.

9. A process according to claim 1, further comprising encapsulating a biomolecule, therapeutic or imaging agent in said nanospheres.

10. A process according to claim 9, wherein encapsulation is carried out by means of physical diffusion.

11. A process according to claim 10, wherein encapsulation is carried out by means of emulsification.

12. A process according to claim 9, wherein said biomolecule, therapeutic or imaging agent is selected from the group consisting of pDNA, polyplexes, growth factors, peptides, viral and non-viral vectors (pDNA), doxorubicin, FITC, tryptophan, rhodamine, 4',6-diamidino-2-phenylindole (DAPI), TOPRO3, flourescein and derivatives thereof, red dyes, green dyes, AlexaFlor; a fluorescent protein, as GFP/eGFP, YFP, and chemicals, APIs, drugs and pro-drugs.

13. A process according to claim 1, wherein the polymeric solution comprises a polymer selected from the group consisting of collagen, elastin, chitosan, hyaluronan, alginate, PEG-based polymer and wherein the crosslinker is a dendrimer selected from the group consisting of: peptide based dendrimers, polyamidoamine (PAMAM), poly (2-dimethyl-aminoethylmethacrylate) (PDMAEMA), polyethyleneglycolmethylether methacrylate (PEGMEMA), ethylene dimethacrylate (EDGMA), poly-l-lysine (PLL), polyethyleneimine (PEI), polyglutamic acid (PGA), poly (ethylene glycol) methacrylate (PEGMA) and poly (propylene glycol) methacrylate (PPGMA), (meth)acrylic acid monomers or NHS monomers with multi-functional vinyl monomers, a polycarboxylic acid-polyethylene glycol-polycarboxylic acid (PPEGP) based dendrimer such as aconitic acid-polyethylene glycol-aconitic acid based dendrimer (APEGA) and combinations thereof.

14. A process according to claim 1, further comprising the step of treating said polymer coated template with a second polymeric solution comprising a polymer selected from the group consisting of polyglutamic acid, hyaluronic acid, alginate, PLGA, poly(caprolactone), and poly(d,l-lactide) to produce multilayer polymeric nanospheres.

* * * * *